(12) United States Patent
Oi et al.

(10) Patent No.: US 10,729,418 B2
(45) Date of Patent: Aug. 4, 2020

(54) ARTIFICIAL TENDON-FORMING AUXILIARY INSTRUMENT, SOMATOMETRY INSTRUMENT, AND AUXILIARY INSTRUMENT SET

(71) Applicant: SUMITOMO BAKELITE CO., LTD., Shinagawa-ku (JP)

(72) Inventors: Keiji Oi, Tokyo (JP); Kei Hyugaji, Akita (JP); Keitaro Sugita, Akita (JP); Akira Kawamata, Akita (JP); Takashi Sato, Akita (JP)

(73) Assignee: SUMITOMO BAKELITE CO., LTD., Shinagawa-ku (JP)

( * ) Notice: Subject to any disclaimer, the term of this patent is extended or adjusted under 35 U.S.C. 154(b) by 415 days.

(21) Appl. No.: 15/525,220

(22) PCT Filed: Oct. 30, 2015

(86) PCT No.: PCT/JP2015/080719
§ 371 (c)(1),
(2) Date: May 8, 2017

(87) PCT Pub. No.: WO2016/080175
PCT Pub. Date: May 26, 2016

(65) Prior Publication Data
US 2017/0333025 A1   Nov. 23, 2017

(30) Foreign Application Priority Data

Nov. 20, 2014  (JP) ................................ 2014-235743
Mar. 10, 2015  (JP) ................................ 2015-046933
Aug. 28, 2015  (JP) ................................ 2015-169610

(51) Int. Cl.
A61B 17/04       (2006.01)
A61F 2/24        (2006.01)
(Continued)

(52) U.S. Cl.
CPC ................ *A61B 17/04* (2013.01); *A61F 2/08* (2013.01); *A61F 2/24* (2013.01); *A61F 2/2457* (2013.01);
(Continued)

(58) Field of Classification Search
CPC .......... A61B 2017/00243; A61B 17/04; A61B 17/0482; A61B 17/0469; A61B 17/0483;
(Continued)

(56) References Cited

U.S. PATENT DOCUMENTS

| | | | | |
|---|---|---|---|---|
| 5,141,497 A | * | 8/1992 | Erskine | A61M 25/0606 604/160 |
| 2003/0105519 A1 | * | 6/2003 | Fasol | A61F 2/2457 623/2.1 |
| 2011/0190792 A1 | * | 8/2011 | Chu | A61B 17/04 606/144 |

FOREIGN PATENT DOCUMENTS

| | | |
|---|---|---|
| JP | 2009-268632 A | 11/2009 |
| WO | WO 99/11201 A2 | 3/1999 |
| WO | WO 2012/040865 A1 | 4/2012 |

OTHER PUBLICATIONS

International Search Report dated Dec. 22, 2015 in PCT/JP2015/080719 Filed Oct. 30, 2015.

* cited by examiner

*Primary Examiner* — Tan-Uyen T Ho
*Assistant Examiner* — Chima U Igboko
(74) *Attorney, Agent, or Firm* — Oblon, McClelland, Maier & Neustadt, L.L.P.

(57) ABSTRACT

According to the present invention, there is provided an artificial tendon-forming auxiliary instrument in which a valve cusp of a cardiac valve and a papillary muscle can be joined together with an artificial tendon through an easy procedure and the artificial tendon can be finished so as to (Continued)

have a desired length. According to an aspect of the present invention, an auxiliary instrument (100) is used for joining a valve cusp (210) of the cardiac valve and a papillary muscle (212) with an artificial tendon (200). A pair of end-portion support portions (20) and (21) respectively supporting the valve cusp (210) and the papillary muscle (212) is provided at both ends in a longitudinal direction. The auxiliary instrument (100) includes first and second tendon insertion ports through which the artificial tendon (200) is inserted, a tendon guide portion (30), and an instrument holding portion (40). The first and second tendon insertion ports are respectively formed in the pair of end-portion support portions (20) and (21) and have diameters greater than a diameter of the artificial tendon (200). The tendon guide portion (30) is formed so as to extend in the longitudinal direction across the first and second tendon insertion ports. The instrument holding portion (40) is formed in an intermediate portion of the tendon guide portion (30) in the longitudinal direction.

33 Claims, 21 Drawing Sheets

(51) Int. Cl.
*A61F 2/08* (2006.01)
*A61F 2/76* (2006.01)
*A61B 17/00* (2006.01)

(52) U.S. Cl.
CPC .............. *A61F 2/2466* (2013.01); *A61F 2/76* (2013.01); *A61B 2017/00243* (2013.01); *A61F 2/2496* (2013.01)

(58) Field of Classification Search
CPC ... A61B 17/0487; A61B 17/68; A61B 17/685; A61B 17/686; A61B 17/7047; A61B 17/7049; A61B 17/705; A61B 17/7052; A61B 17/1146; A61B 2017/1132; A61B 2017/1135; A61B 2017/1139; A61B 2017/1142; A61F 2/2457; A61F 2/08; A61F 2/24; A61F 2/76; A61F 2/2496; A61F 2/2466; A61F 2/2442; A61F 2/2445; A61F 2/2448; A61F 2/2451; A61F 2/2454; A61F 2/246; A61F 2/2463; A61F 2/2469; A61F 2/0805; A61F 2/0811; A61F 2002/0817; A61F 2002/0823; A61F 2002/0829; A61F 2002/0835; A61F 2002/0841; A61F 2002/0847; A61F 2002/0852; A61F 2002/0858; A61F 2002/0864; A61F 2002/087; A61F 2002/0876; A61F 2002/0882; A61F 2002/0888; A61F 2002/0894; A61M 25/0668
See application file for complete search history.

ARTIFICIAL TENDON-FORMING AUXILIARY INSTRUMENT, SOMATOMETRY INSTRUMENT, AND AUXILIARY INSTRUMENT SET

TECHNICAL FIELD

The present invention relates to an artificial tendon-forming auxiliary instrument for forming an artificial tendon in a valve in the heart, and an auxiliary instrument set; and a somatometry instrument for measuring a distance between spots physically separated from each other inside a living body, and an auxiliary instrument set.

Priority is claimed on Japanese Patent Application No. 2014-235743, filed on Nov. 20, 2014, Japanese Patent Application No. 2015-046933, filed on Mar. 10, 2015, and Japanese Patent Application No. 2015-169610, filed on Aug. 28, 2015, the contents of which are incorporated herein by reference.

BACKGROUND ART

In accordance with progress in the medical technology, surgical treatment has been available for diverse spots inside a living body. For example, there is a known symptom such as mitral valve insufficiency caused due to a rheumatic disease or the like disrupting opening and closing of a valve cusp in the heart. As surgical treatment for treating such a symptom, there is a known technique called mitral valve plasty (MVP).

The structure of the heart and the MVP will be described below in detail.

The heart has the atriums and the ventricles on the right and left, in which the mitral valve, the tricuspid valve, the aortic valve, and the pulmonary arterial valve cause blood to flow in a predetermined direction and prevent the blood from flowing backward.

FIGS. 1A and 1B are schematic views of a heart 300 of a human being. For example, a mitral valve 310 is formed between a left atrium 302 and a left ventricle 304, and two valve cusps 210 protrude from the left atrium 302 toward the left ventricle 304. When the left atrium 302 contracts, the valve cusps 210 are open and a blood flow heads for the left ventricle 304. In addition, when the left ventricle 304 contracts, the valve cusps 210 are closed and the blood flow is prevented from flowing backward to the left atrium 302. Accordingly, the blood flow unilaterally heads for an aorta 320 from the left ventricle 304. A tricuspid valve 312, an aortic valve 314, and a pulmonary arterial valve 316 are respectively configured with three sets of valve cusps 210, thereby causing blood flows to respectively and unilaterally head for a right ventricle 308 from a right atrium 306, for the aorta 320 from the left ventricle 304, and for a pulmonary vein 322 from the right ventricle 308.

A normal valve cusp 210 is joined to a papillary muscle 212 positioned in front (on downstream side) of the valve cusp 210 in a blood flow direction, by tendons 214. In FIGS. 1A and 1B, in regard to the mitral valve 310 and the tricuspid valve 312, the papillary muscles 212 and the tendons 214 are illustrated. In regard to the aortic valve 314 and the pulmonary arterial valve 316, illustration thereof is omitted. The valve cusps 210 are joined to the papillary muscles 212 by the tendons 214, thereby being able to maintain a state of protruding forward (to downstream side) in the blood flow direction. When being closed, while maintaining a state where the valve cusps 210 protrude forward (to downstream side), the valve cusps 210 adhere to each other, thereby closing a cardiac valve. When the cardiac valve is closed, the papillary muscles 212 contract and tensile forces of the tendons 214 increase. Accordingly, against the pressure of the blood flow flowing backward, the protruding state of the valve cusps 210 is maintained and the valve cusps 210 have no chance to be inverted in a backward direction.

However, for example, regarding a case of the mitral valve 310, there is a symptom such as mitral valve insufficiency caused due to a rheumatic disease, tendon rupture, or the like disrupting opening and closing of the valve cusps 210. In a case of such a symptom, the tendons 214 joining the valve cusps 210 of the mitral valve 310 and the papillary muscles 212 are stretched or broken. Accordingly, even if the papillary muscles 212 contract, the valve cusps 210 are not sufficiently closed, or the valve cusps 210 are inverted toward the left atrium 302. Similarly, in regard to the aortic valve 314, the tricuspid valve 312, and the pulmonary arterial valve 316 as well, valvular insufficiency disrupting opening and closing of the valve cusps 210 has been reported.

In surgical treatment for such valvular insufficiency of the cardiac valve, a procedure (valvoplasty) of joining the valve cusps 210 and the papillary muscles 212 together is performed by using string-like artificial tendons which are artificially produced so as to copy the tendons 214. As described above, the procedure related to the mitral valve 310 is called the mitral valve plasty (MVP). The MVP is surgical treatment performed with respect to such a symptom while aiming at normalizing the operation of the valve cusps 210 by joining the valve cusps 210 and the papillary muscles 212 with the artificial tendons.

PTL 1 discloses an auxiliary device that is an instrument used in the mitral valve plasty and includes a papillary muscle contact portion which is brought into contact with a portion of a papillary muscle stitched with an artificial tendon, and a hook portion which hooks a side of the artificial tendon stitching a valve cusp. The hook portion is formed on a tip side of a rod-shaped holding portion. The papillary muscle contact portion at a distal tip of the auxiliary device, and the hook portion are provided so as to be separated from each other by a predetermined size. While the artificial tendon stitching the papillary muscle is pressed by the papillary muscle contact portion, when both ends of the artificial tendon are tied together on the hook portion, the artificial tendon can have a length matching the predetermined size. Accordingly, the papillary muscle and the valve cusp can be joined together with the artificial tendon having a desired length. In addition, PTL 1 discloses that in order to join the artificial tendon with a desired length, the auxiliary device corresponding to the length of the artificial tendon to be reconstructed is selected, and a trial corresponding to the desired length is attempted.

CITATION LIST

Patent Literature

[PTL 1] Japanese Unexamined Patent Application, First Publication No. 2009-268632

SUMMARY OF INVENTION

Technical Problem

Both ends of an artificial tendon stitching a papillary muscle and a valve cusp are fixed by being tied together. When the artificial tendon is tied, a predetermined tensile force is generated. Accordingly, in a state where the valve cusp and the papillary muscle pull each other and the distance therebetween is narrowed, the length of the artificial tendon is fixed and the distance between the valve cusp and the papillary muscle is determined. In valvoplasty using the artificial tendon, without depending on the skill of a technician such as a physician as much as possible, the valvoplasty is required to be finished such that the distance between the valve cusp and the papillary muscle stitched with the artificial tendon meets a predetermined length. However, an auxiliary device in PTL 1 has a problem in that it is not easy to perform work of tying the artificial tendon on a hook portion formed in a rod-shaped holding portion so that the technician is required to be highly skilled. That is, the rod-shaped holding portion extends to a proximal side of the technician beyond the hook portion. Therefore, when both ends of the artificial tendon are tied together in a state where the valve cusp is mounted on the hook portion, the holding portion unavoidably interferes with the valve cusp. In a case where the valvoplasty is performed by using the auxiliary device in PTL 1, there is a need to tie the artificial tendon in a state where the valve cusp is turned up along the rod-shaped holding portion, thereby leading to a problem in that it is troublesome to conduct a procedure of forming a knot on the obliquely tilted valve cusp and it is difficult to finish the artificial tendon with a desired length. In addition, when the auxiliary device is detached after the artificial tendon is fixed, the holding portion interferes with the valve cusp or the knot, thereby disrupting the detaching work.

The present invention has been made in consideration of the foregoing problems, and there are provided an artificial tendon-forming auxiliary instrument in which a valve cusp of a cardiac valve and a papillary muscle can be joined together with an artificial tendon through an easy procedure and the artificial tendon can be finished so as to have a desired length, and an auxiliary instrument set.

Incidentally, when the auxiliary device disclosed in PTL 1 is used, the following problem is entailed. That is, PTL 1 discloses that the length of the artificial tendon is to be determined through a prudent review while referring to a preoperative echocardiogram and the like. However, in the preoperative echocardiogram and the like, there is a limit to appropriately determining the length of the artificial tendon ranging approximately from ten-odd millimeters to tens of millimeters by measuring the distance between a valve cusp 210 and a papillary muscle 212. Therefore, even if an auxiliary device suitable for the length of the artificial tendon determined through the preoperative echocardiogram and the like is selected, there are cases where the length does not actually correspond to the distance between the valve cusp 210 and the papillary muscle 212, thereby causing incompatibility of the length of the artificial tendon.

The problem regarding the incompatibility of the length of the artificial tendon during execution of the MVP described above is a problem caused due to difficulties of directly measuring the distance between the valve cusp and the papillary muscle. The MVP is an example of a surgical operation performed inside a living body. However, in various other types of surgical operations and the like as well, there is a demand for an instrument which can accurately measure the distance between a first site inside a living body, and a second site physically separated from the first site.

The present invention has also been made in consideration of the foregoing problems, and there are provided a somatometry instrument which can accurately measure a distance between a first site inside a living body, and a second site physically separated from the first site; and an auxiliary instrument set.

Solution to Problem

According to the present invention, there is provided an artificial tendon-forming auxiliary instrument used for joining a valve cusp of a cardiac valve and a papillary muscle with an artificial tendon. The artificial tendon-forming auxiliary instrument includes a pair of end-portion support portions which respectively support the valve cusp and the papillary muscle and are provided at both ends of the instrument in a longitudinal direction, first and second tendon insertion ports which are respectively formed in the pair of end-portion support portions and have diameters greater than a diameter of the artificial tendon so that the artificial tendon is inserted, a tendon guide portion which is formed so as to extend in the longitudinal direction across the first and second tendon insertion ports, and an instrument holding portion which is formed in an intermediate portion of the tendon guide portion in the longitudinal direction.

According to the invention, a technician holding the instrument holding portion can install the tendon guide portion in the artificial tendon by causing the artificial tendon stitching at least one side of the papillary muscle and the valve cusp to be inserted through the first and second tendon insertion ports. Accordingly, in a state where a gap between the valve cusp and the papillary muscle supported by the end-portion support portions at both ends maintains a predetermined length, that is, a length of the artificial tendon-forming auxiliary instrument of the present invention in the longitudinal direction, the artificial tendon can be fixed to the valve cusp or the papillary muscle. Since the instrument holding portion is formed in the intermediate portion in the longitudinal direction, the instrument holding portion does not interfere with the valve cusp when the artificial tendon is fixed, and the valve cusp is not turned up as the instrument in PTL 1.

In addition, according to an aspect of the present invention, there is provided an auxiliary instrument set including a plurality of the artificial tendon-forming auxiliary instruments.

According to the present invention, there is provided a somatometry instrument for measuring a distance between a first site inside a living body and a second site physically separated from the first site. The somatometry instrument includes an end-portion abutment portion which is able to abut on the first site and is provided at one end of the somatometry instrument in a longitudinal direction; a first insertion port which is provided in the end-portion abutment portion and through which an artificial thread stitching the first site is inserted; a draw-out portion which is provided at an opposite end facing the end-portion abutment portion in the longitudinal direction or at an intermediate portion that is an intermediate region between the end-portion abutment portion and the opposite end, and through which the artificial thread inserted through the first insertion port is drawn out in an outward direction of the somatometry instrument; and a measurement portion which is provided in the intermediate portion and measures the distance between the first site and the second site.

In addition, according to another aspect of the present invention, there is provided an auxiliary instrument set including the somatometry instrument according to the present invention, and an artificial tendon-forming auxiliary instrument used for joining a valve cusp of a cardiac valve and a papillary muscle positioned on a downstream side in a normal blood flow direction with respect to the valve cusp, with an artificial tendon.

Advantageous Effects of Invention

According to the artificial tendon-forming auxiliary instrument and the auxiliary instrument set of the present invention, the valve cusp of the cardiac valve and the papillary muscle can be joined together with the artificial tendon through an easy procedure and the artificial tendon can be finished so as to have a desired length.

According to the artificial tendon-forming auxiliary instrument of the present invention, a distance between predetermined spots inside a living body, such as the distance between the valve cusp (that is, first site) of the cardiac valve and the papillary muscle (that is, second site) physically separated from the valve cusp can be easily and accurately measured.

In addition, according to the auxiliary instrument set of the aspect of the present invention, the distance between the valve cusp of the cardiac valve and the papillary muscle can be measured through the somatometry instrument of the present invention, and the artificial tendon can be finished so as to have a desired length by using the artificial tendon-forming auxiliary instrument having a length corresponding to the distance.

DESCRIPTION OF EMBODIMENTS

Hereinafter, embodiments of the present invention will be described based on the drawings. In each of the drawings, common reference signs are applied to corresponding configuration elements and overlapping description will be suitably omitted.

Figure 2:
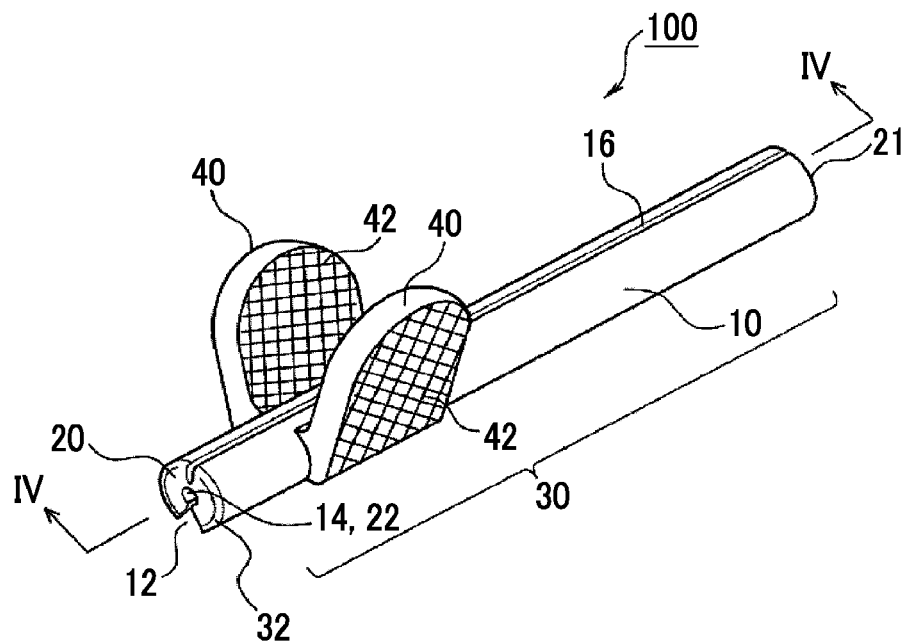
FIG. 2 is a perspective view of an artificial tendon-forming auxiliary instrument of a first embodiment of the present invention.
Figure 3:
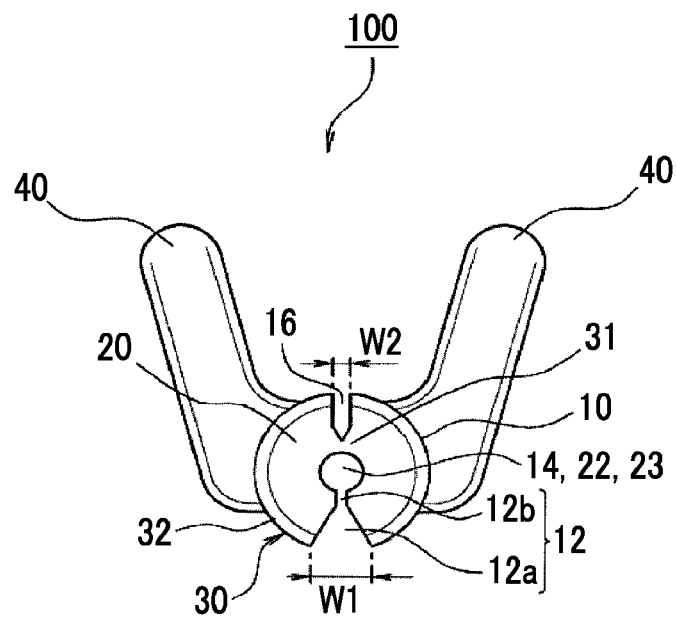
FIG. 3 is a front view of the artificial tendon-forming auxiliary instrument.
Figure 4:
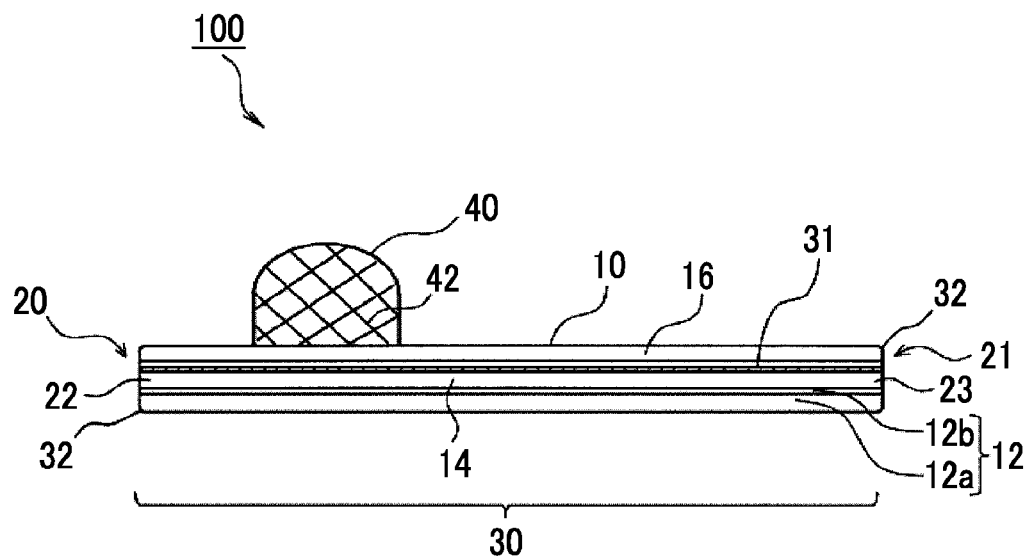
FIG. 4 is a sectional view taken along line IV-IV in FIG. 2.
Figure 5A:
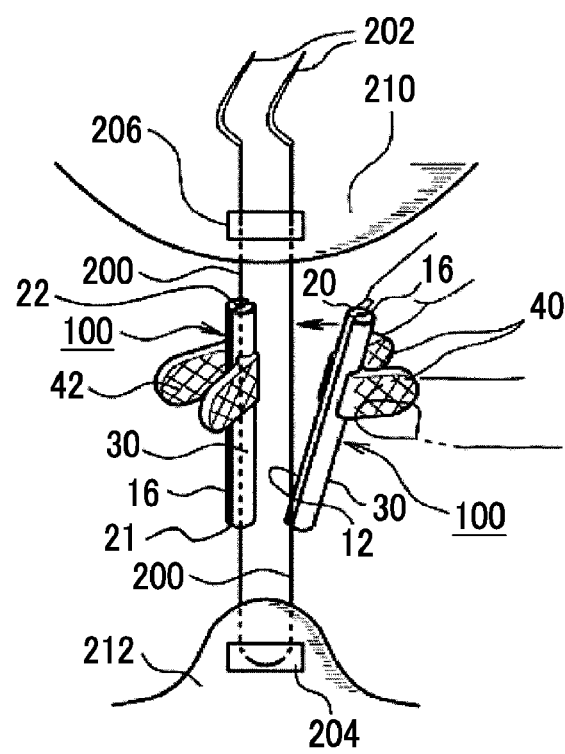
FIG. 5A is a schematic view illustrating a state where the artificial tendon-forming auxiliary instruments are individually installed in an artificial tendon.
Figure 5B:
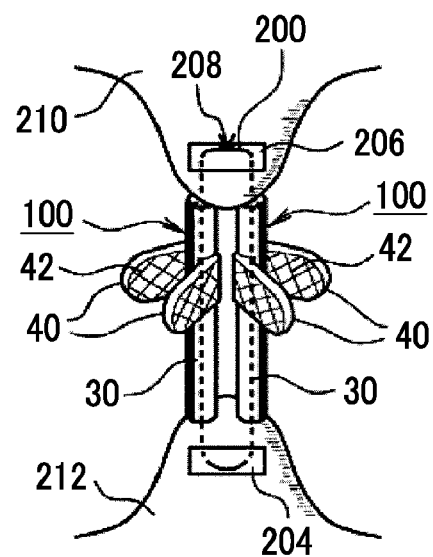
FIG. 5B is a schematic view illustrating a state of a pair of the artificial tendons in which the artificial tendon-forming auxiliary instruments are installed and which are tied together.
Figure 5C:
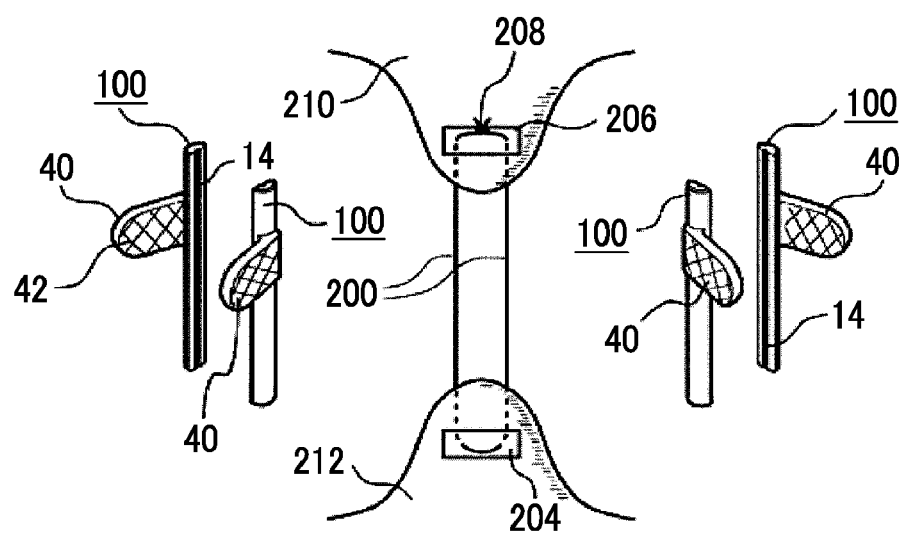
FIG. 5C is a schematic view illustrating a state where the artificial tendon-forming auxiliary instruments are detached from the artificial tendons.

FIG. 2 is a perspective view of an artificial tendon-forming auxiliary instrument (hereinafter, will also be simply abbreviated to "auxiliary instrument") 100 of a first embodiment of the present invention. FIG. 3 is a front view of the auxiliary instrument 100. A state where the auxiliary instrument 100 is viewed in a longitudinal direction will be called the front view. FIG. 4 is a sectional view taken along line IV-IV in FIG. 2. FIG. 5A is a schematic view illustrating a state where the auxiliary instruments 100 are individually installed in an artificial tendon 200. FIG. 5B is a schematic view illustrating a state of a pair of the artificial tendons 200 in which the auxiliary instruments 100 are installed and which are tied together. FIG. 5C is a schematic view illustrating a state where the auxiliary instruments 100 are detached from the artificial tendons 200.

First, the outline of the auxiliary instrument 100 of the present embodiment will be described.

The auxiliary instrument 100 is used for joining a valve cusp 210 of a cardiac valve and a papillary muscle 212 with the artificial tendon 200 (refer to each diagram of FIG. 5) and is provided with a pair of end-portion support portions 20 and 21 which respectively support the valve cusp 210 and the papillary muscle 212 and are provided at both ends of the auxiliary instrument 100 in the longitudinal direction (refer to FIG. 2). The auxiliary instrument 100 of the present embodiment includes a first tendon insertion port 22 and a second tendon insertion port 23 through which the artificial tendon 200 is inserted, a tendon guide portion 30, and instrument holding portions 40 (refer to FIG. 4). The first tendon insertion port 22 and the second tendon insertion port 23 are respectively formed in the pair of end-portion support portions 20 and 21 and have diameters greater than the diameter of the artificial tendon 200. The tendon guide portion 30 is formed so as to extend in the longitudinal direction across the first tendon insertion port 22 and the second tendon insertion port 23. The instrument holding portions 40 are formed in an intermediate portion of the tendon guide portion 30 in the longitudinal direction.

Next, the present embodiment will be described in detail.

Figure 1A:
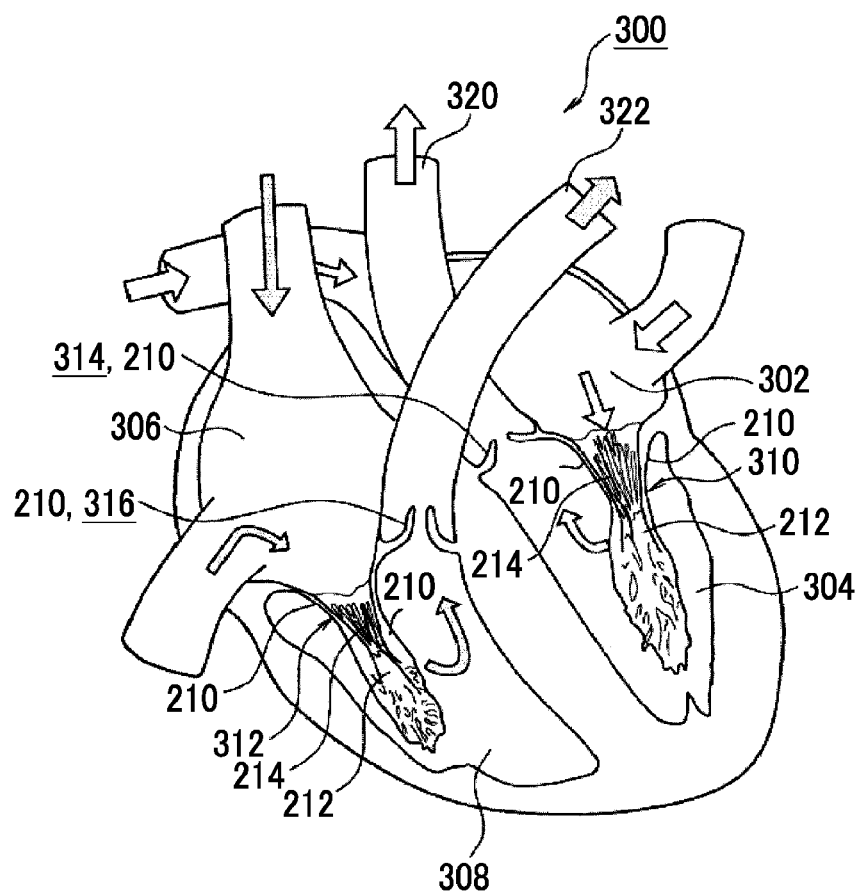
FIG. 1A is a schematic view of the heart of a human being.

The cardiac valve in which the valve cusp 210 and the papillary muscle 212 are joined together with the artificial tendons 200 by using the auxiliary instrument 100 includes a mitral valve 310; and a tricuspid valve 312, an aortic valve 314, and a pulmonary arterial valve 316 as well (refer to FIG. 1A). Among these, the present embodiment exemplifies a case where the auxiliary instrument 100 is used in mitral valve plasty in which tendons 214 in one or both of two valve cusps 210 of the mitral valve 310 are reconstructed with the artificial tendons 200. In a normal mitral valve 310, the valve cusps 210 are respectively joined to the papillary muscles 212 via a plurality of tendons 214. The present embodiment exemplifies a case where all of the tendons 214 are broken, and the valve cusp 210 and the papillary muscle 212 separated from each other are joined together with the artificial tendon 200. However, the embodiment is not limited thereto. The auxiliary instrument 100 may be used in a case where the valve cusp 210 and the papillary muscle 212 which have been joined together through one or the plurality of tendons 214 are additionally joined together with the artificial tendon 200. In addition, the description below exemplifies an aspect in which one artificial tendon 200 is caused to be in a loop state, and the valve cusp 210 and the papillary muscle 212 are stitched with the artificial tendon 200 two spots each. However, the aspect is not limited thereto. The valve cusp 210 and the papillary muscle 212 may be joined together with one or a plurality of the artificial tendons 200 in a non-loop state.

The auxiliary instrument 100 of the present embodiment is broadly configured with the tendon guide portion 30 configuring a main body portion, the first tendon insertion port 22 and the second tendon insertion port 23 which are respectively formed at both ends of the tendon guide portion 30 in the longitudinal direction, and a pair of the instrument holding portions 40 which a technician grips with fingers or an instrument such as tweezers (hereinafter, there may be cases of being referred to as "fingers or the like") when holding the tendon guide portion 30.

As illustrated in FIG. 5B, the tendon guide portion 30 is a portion which is interposed between the valve cusp 210 and the papillary muscle 212 and guides the artificial tendon 200 to a space between the valve cusp 210 and the papillary muscle 212 in a state of being lengthened practically straight. The tendon guide portion 30 of the present embodiment is in a hollow tubular shape including a central lumen 14. However, the present invention is not limited thereto. It is possible to adopt various shapes such as a half-split tubular shape exemplified as a seventh embodiment (refer to FIG. 11A).

As illustrated in FIG. 2, the tendon guide portion 30 of the present embodiment has the hollow tubular shape including a slit portion 12 which is open with an opening width W1 (refer to FIG. 3) capable of receiving the artificial tendon 200 (refer to FIG. 5A), and the central lumen 14 which penetrates the tendon guide portion 30 in the longitudinal direction. The slit portion 12 is formed on a side of the tendon guide portion 30 across the overall length in the longitudinal direction and communicates with the central lumen 14 through the side.

The tendon guide portion 30 of the present embodiment has a substantially cylindrical shape in which the central lumen 14 is formed so as to penetrate the tendon guide portion 30. A circumferential surface 10 of the tendon guide portion 30 is a substantially cylindrical surface, and the slit portion 12 is formed along the central axis (axis in the longitudinal direction) thereof so as to be cut in a radial direction of the tendon guide portion 30 at a depth from the circumferential surface 10 to the central lumen 14. As illustrated in FIG. 3, the slit portion 12 is configured with a narrow-width portion 12b and a wide-width portion 12a. The narrow-width portion 12b is a portion having a diameter smaller than the diameter of the central lumen 14 and is connected to the central lumen 14. The wide-width portion 12a is a portion which is smoothly and continuously provided radially outward beyond the narrow-width portion 12b and of which the width size is gradually widened toward the circumferential surface 10. The maximum width size of the wide-width portion 12a is the opening width W1, and the minimum width size of the wide-width portion 12a is substantially equal to the width size of the narrow-width portion 12b. The opening width W1 of the slit portion 12 is sufficiently greater than the diameter (wire diameter) of the artificial tendon 200.

The slit portion 12 is not limited to the above form and can employ various forms. Various embodiments in which the forms of the slit portion 12 are varied will be described later with reference to FIGS. 8A to 11B.

The central lumen 14 is a penetration hole which is formed substantially at the center of the tendon guide portion 30. The central lumen 14 of the present embodiment is formed so as to have a substantially circular shape in a front view as illustrated in FIG. 3. The present embodiment exemplifies a case where one artificial tendon 200 corresponding to one side of the artificial tendon 200 in a loop state is inserted through the central lumen 14. However, the present invention is not limited thereto. The central lumen 14 may accommodate two straight portions of the artificial tendon 200 in a loop state. In this case, it is preferable that the diameter (inner diameter) of the central lumen 14 is equal to or greater than twice the diameter (wire diameter) of the artificial tendon 200. In addition, in place of the present embodiment, in a case where the valve cusp 210 and the papillary muscle 212 are stitched with the artificial tendon 200 in a non-loop state, the plurality (for example, three or more) of artificial tendon 200 may be accommodated in the central lumen 14.

The instrument holding portions 40 are portions for holding the auxiliary instrument 100 with fingers or the like of a technician. The instrument holding portions 40 of the present embodiment form a pair and have one-plate shapes protruding radially outward from the circumferential surface 10 of the tendon guide portion 30. Accordingly, as illustrated in FIG. 5A, for example, a technician can hold the auxiliary instrument 100 such that the pair of instrument holding portions 40 is interposed with a thumb and an index finger. Forming regions of the instrument holding portions 40 are on an inner side of both ends of the tendon guide portion 30 in the longitudinal direction. Accordingly, as illustrated in FIG. 5B, when the auxiliary instrument 100 is interposed between the valve cusp 210 and the papillary muscle 212, the instrument holding portions 40 do not interfere with any of the valve cusp 210 and the papillary muscle 212. Accordingly, when work of tying both ends of the artificial tendon 200 together is performed, the instrument holding portions 40 are not disrupted.

The instrument holding portions 40 are formed at positions biased to the end-portion support portion on one side (in the present embodiment, the end-portion support portion 20) in the intermediate portion of the tendon guide portion 30. Accordingly, as illustrated in FIG. 5A, it is possible to acquire excellent workability when the artificial tendon 200 is inserted through the tendon guide portion 30 through the slit portion 12, in other words, when the tendon guide portion 30 is installed with respect to the artificial tendon 200. That is, the instrument holding portions 40 approach one (in present embodiment, the first tendon insertion port 22) of the first tendon insertion port 22 and the second tendon insertion port 23 (refer to FIG. 4) respectively formed at both ends of the tendon guide portion 30. Therefore, in a state where the instrument holding portions 40 are held with fingers, a technician can operate the first tendon insertion port 22 close at hand, with high accuracy.

The end-portion support portions 20 and 21 are portions which are respectively supporting the valve cusp 210 and the papillary muscle 212 and are provided at both ends of the tendon guide portion 30 of the auxiliary instrument 100 in the longitudinal direction. The end-portion support portions 20 and 21 are formed so as to have plane shapes. The end-portion support portions 20 and 21 may have flat plane shapes or curved plane shapes. If the end-portion support portion 20 and the end-portion support portion 21 are formed so as to have the plane shapes, as illustrated in FIG. 5B, when the artificial tendon 200 is tied with a predetermined tensile force, the end-portion support portion 20 and the end-portion support portion 21 do not excessively intrude on the valve cusp 210 or the papillary muscle 212. Accordingly, the tendon guide portion 30 of the auxiliary instrument 100 serves as a spacer, and the longitudinal size thereof becomes the separation distance between the valve cusp 210 and the papillary muscle 212. When the artificial tendon 200 is fixed to the valve cusp 210 in such a state, after the mitral valve plasty, the valve cusp 210 and the papillary muscle 212 are thereby joined together with the artificial tendon 200 having a desired length.

The tendon guide portion 30 can be produced by using a soft resin material such as a soft vinyl chloride resin, a polyurethane resin, and a silicone resin. Accordingly, when the artificial tendon 200 is tied while having the tendon guide portion 30 as the spacer, even if the valve cusp 210 or the papillary muscle 212 is pressed with respect to the tendon guide portion 30 with a predetermined force, the valve cusp 210 or the papillary muscle 212 is not damaged by the tendon guide portion 30.

The instrument holding portions 40 may be integrally molded with the tendon guide portion 30 by using one material. Otherwise, after the instrument holding portions 40 are produced as different members, the instrument holding portions 40 may be integrated with the tendon guide portion 30 by being bonded to the circumferential surface 10. The present embodiment exemplifies a case where the instrument holding portions 40 are integrally molded with the tendon guide portion 30 by using one material. Accordingly, the tendon guide portion 30 and the instrument holding portions 40 are not unexpectedly separated from each other, and the manufacturing process and the number of components can be reduced. Specifically, the auxiliary instrument 100 can be produced through injection molding of a thermoplastic soft resin material.

As illustrated in FIG. 2, a rough surface portion 42 is provided in at least a part on the surface of the instrument holding portion 40. The rough surface portion 42 of the present embodiment has a ridged pattern configured with a plurality of recessed grooves intersecting each other. The rough surface portion 42 can be formed by transcribing projections which are formed on the inner surface of a mold (not illustrated) used in injection molding of the instrument holding portions 40. Moreover, the rough surface portion 42 may be an uneven portion in which many points are randomly formed or arranged in an array or may be the projections. In addition, the rough surface portion 42 may be formed by performing roughening treatment of the surface of the instrument holding portions 40 after injection molding.

In the auxiliary instrument 100 of the present embodiment, the rough surface portion 42 is formed in both front and rear surfaces of the pair of instrument holding portions 40 substantially in its entirety. The gap between the recessed grooves forming the ridged pattern configuring the rough surface portion 42 is not particularly limited. However, it is preferable that the plurality of recessed grooves are formed in each instrument holding portion 40 in the width direction and the length direction. When the rough surface portion 42 is formed in the instrument holding portion 40, a frictional force of the instrument holding portion 40 increases. Therefore, a technician can reliably pinch the instrument holding portions 40 with fingers or an instrument such as tweezers.

The first tendon insertion port 22 is formed in the end-portion support portion 20, and the second tendon insertion port 23 is formed in the end-portion support portion 21. The first tendon insertion port 22 of the present embodiment is an open end of the central lumen 14 on one side, and the second tendon insertion port 23 is an open end of the central lumen 14 on the other side. First, the artificial tendon 200 which stitches the papillary muscle 212 and protrudes is introduced to the first tendon insertion port 22 or the second tendon insertion port 23 (in the present embodiment, the first tendon insertion port 22). The artificial tendon 200 is guided inside the central lumen 14 and is driven out through the second tendon insertion port 23 or the first tendon insertion port 22 (in the present embodiment, the second tendon insertion port 23). When the valve cusp 210 is stitched with the driven out artificial tendon 200, the valve cusp 210 and the papillary muscle 212 are joined together by the artificial tendon 200 matching the length of the central lumen 14 (longitudinal size of the tendon guide portion 30).

As illustrated in FIG. 4, in the first tendon insertion port 22 and the second tendon insertion port 23, the slit portion 12 is continuously provided in the radial direction of the tendon guide portion 30. The slit portion 12 is formed across the overall length of the tendon guide portion 30 in the longitudinal direction. Therefore, as illustrated in FIG. 5A, in a state where the slit portion 12 encounters the artificial tendon 200, the tendon guide portion 30 can be installed from the side.

On the circumferential surface 10 of the tendon guide portion 30, an easily-tearable portion 16 for tearing the tendon guide portion 30 is formed along the longitudinal direction.

When the easily-tearable portion 16 is formed in the tendon guide portion 30, after the valve cusp 210 and the papillary muscle 212 are joined together with the artificial tendon 200, the tendon guide portion 30 is broken along the longitudinal direction so as to be divided into a plurality of pieces. Accordingly, the auxiliary instrument 100 can be easily detached from the artificial tendon 200. As illustrated in each diagram of FIG. 5, it is favorable to install the auxiliary instrument 100 in the artificial tendon 200 such that the instrument holding portions 40 approach the valve cusp 210 rather than the papillary muscle 212. Accordingly, when the pair of instrument holding portions 40 is held with an instrument such as tweezers so as to break the tendon guide portion 30, it is possible to easily have access to the instrument holding portions 40 from a left atrium 302 (refer to FIGS. 1A and 1B) of a test subject subjected to thoracotomy.

The easily-tearable portion 16 of the present embodiment is formed on a side facing the slit portion 12 in the circumferential surface 10 of the tendon guide portion 30 along the slit portion 12. The easily-tearable portion 16 is continuously or intermittently formed along the slit portion 12 across the overall length in the longitudinal direction.

In addition, the pair of instrument holding portions 40 is formed on both sides so as to interpose the easily-tearable portion 16 therebetween. Accordingly, when the pair of instrument holding portions 40 is pulled outward in directions opposite to each other with a force equal to or greater than predetermined strength, the tendon guide portion 30 is torn across the overall length. As illustrated in FIG. 5C, the auxiliary instrument 100 is completely separated into two portions. The easily-tearable portion 16 does not intersect the slit portion 12 and is formed across the overall length of the tendon guide portion 30 in the longitudinal direction. Therefore, unexpected small pieces are not generated when the tendon guide portion 30 is torn.

The easily-tearable portion 16 is a recessed groove which is cut from the circumferential surface 10 of the tendon guide portion 30 toward the central lumen 14 in a non-penetration manner. An opening width W2 of the easily-tearable portion 16 is smaller than the opening width W1 of the slit portion 12. By restraining the opening width W2 of the easily-tearable portion 16 to be smaller than the opening width W1 of the slit portion 12, a technician is prevented from being confused between the easily-tearable portion 16 and the slit portion 12.

In the shape of the recessed groove in the easily-tearable portion 16 of the present embodiment, as illustrated in FIG. 3, the bottom portion has a V-shape, and the opening width W2 is uniform in the vicinity of the circumferential surface 10. Accordingly, when the instrument holding portions 40 are pulled outward, stress is concentrated on the V-shaped bottom portion of the easily-tearable portion 16, and the tendon guide portion 30 is thereby easily broken.

In addition, the pair of instrument holding portions 40 is formed so as to respectively protrude outward from the circumferential surface 10 of the tendon guide portion 30 and extend toward a side facing the slit portion 12 (that is, a side on which the easily-tearable portion 16 is formed). Therefore, in a state where a technician pinches the instrument holding portions 40 with fingers or the like, the slit portion 12 corresponding to the side of receiving the artificial tendon 200 is naturally oriented to the distal side when viewed from the technician. Therefore, as illustrated in FIG. 5A, when the tendon guide portion 30 is installed in the artificial tendon 200, the artificial tendon 200 can be inserted into to the slit portion 12, not into the easily-tearable portion 16, through a natural procedure.

As illustrated in FIGS. 3 and 4, the easily-tearable portion 16 is the bottomed recessed groove, and a residual portion 31 of the tendon guide portion 30 is present between the bottom portion of the easily-tearable portion 16 and the central lumen 14. In addition, the tendon guide portion 30 is produced by using a soft resin material having low brittleness. Therefore, when the pair of instrument holding portions 40 is pinched and is caused to approach each other, the opening width W1 of the slit portion 12 is widened without tearing the easily-tearable portion 16 (residual portion 31). Accordingly, as illustrated in FIG. 5A, when the tendon guide portion 30 is installed in the artificial tendon 200, if a technician pinches the instrument holding portions 40 with two fingers, the opening width W1 of the slit portion 12 is widened. Therefore, a procedure of inserting the artificial tendon 200 into the slit portion 12 is easily performed.

The tendon guide portion 30 may be colorless or may be colored with a color. In the auxiliary instrument 100 of the present embodiment, a pigment is kneaded with a soft resin material configuring the tendon guide portion 30, and the auxiliary instrument 100 is colored. Accordingly, visibility of the auxiliary instrument 100 is improved.

In addition, a radio-opaque contrast agent such as barium sulfate may be kneaded with the soft resin material configuring the tendon guide portion 30. Accordingly, after the procedure ends, it is possible to check that the auxiliary instrument 100 is not left behind inside a body lumen of a test subject, through X-ray radiography.

In place of the present embodiment, without forming the easily-tearable portion 16 and dividing the auxiliary instrument 100 into a plurality of pieces, the auxiliary instrument 100 may be detached from the artificial tendon 200. That is, when the pair of instrument holding portions 40 is strongly pulled outward in directions opposite to each other from the state illustrated in FIG. 5B, the tendon guide portion 30 can be subjected to plastic deformation such that the slit portion 12 is open wide. Accordingly, the artificial tendon 200 accommodated in the central lumen 14 can easily pass through the narrow-width portion 12b, and the auxiliary instrument 100 can be thereby detached from the artificial tendon 200.

As illustrated in FIG. 4, chamfered portions 32 are respectively formed in the circumferences of both ends of the tendon guide portion 30 in the longitudinal direction. Forming of the chamfered portion 32 includes forming of the chamfered portion 32 through chamfering processing after the tendon guide portion 30 is molded, in addition to molding of the tendon guide portion 30 in a shape having the chamfered portion 32 at the time of injection molding of the tendon guide portion 30.

The chamfered portion 32 may be formed through round chamfering in which the circumferences of the end-portion support portion 20 and the end-portion support portion 21 are finished with curved surfaces, or the chamfered portion 32 may be formed through isosceles-right-triangular chamfering in which the circumferences thereof are finished with flat surfaces.

If the chamfered portions 32 are formed in the circumferences of the end-portion support portion 20 and the end-portion support portion 21 of the tendon guide portion 30, when the auxiliary instrument 100 is torn through the easily-tearable portion 16 from the interposed state illustrated in FIG. 5B, or when the torn auxiliary instrument 100 is detached from the artificial tendon 200, the end-portion support portion 20 and the end-portion support portion 21 are restrained from intruding on the valve cusp 210 or the papillary muscle 212.

Next, by using FIGS. 5A to 5C, an example of a method of using the auxiliary instrument 100 of the present embodiment (hereinafter, there may be cases of being referred to as "present method") will be described. First, as illustrated in FIG. 5A, after both the papillary muscle 212 and the valve cusp 210 are stitched with the artificial tendon 200, a first procedure in which the auxiliary instrument 100 is installed in the artificial tendon 200 is performed. However, as described below, in a state where one of the papillary muscle 212 and the valve cusp 210 is stitched with the artificial tendon 200, it is possible to perform a second procedure in which after the artificial tendon 200 is inserted through the auxiliary instrument 100, the other one of the papillary muscle 212 and the valve cusp 210 is punctured with the artificial tendon 200.

In the first procedure, as illustrated in FIG. 5A, with respect to one of the papillary muscle 212 and the valve cusp 210, two spots close to each other are stitched with the artificial tendon 200, and the artificial tendon 200 is caused to make a U-turn. Since the papillary muscle 212 is positioned in the left ventricle deeper than the valve cusp 210, it is favorable to stitch the papillary muscle 212 with the artificial tendon 200 in advance. It is favorable that a pad 204 is installed in a turn-around portion of the artificial tendon 200. In the present method, puncture needles 202 are respectively installed in both ends of the artificial tendon 200. Prior to puncturing the papillary muscle 212, the pad 204 is punctured with the two puncture needles 202, and the pad 204 is disposed in the intermediate portion of the artificial tendon 200.

The puncture needles 202 used in the present method are curved needles. Even in a case of having access to the papillary muscle 212 from the left ventricle through the mitral valve 310 (refer to FIGS. 1A and 1B), puncturing can be easily performed with the puncture needles 202 from the papillary muscle 212 toward the valve cusp 210, and a low invasive procedure can be thereby performed. In the auxiliary instrument 100 of the present embodiment, the slit portion 12 is formed along the tendon guide portion 30 across the overall length in the longitudinal direction, and the tendon guide portion 30 can be installed with respect to the artificial tendon 200 from the side. Therefore, there is no need to insert the curved puncture needles 202 through the central lumen 14 of the tendon guide portion 30. In other words, since there is no need to insert the puncture needles 202 through the central lumen 14 of the tendon guide portion 30, it is possible to use curved needles as the puncture needles 202.

Next, the papillary muscle 212 is punctured individually with the puncture needles 202. Accordingly, the pad 204 abuts on the papillary muscle 212. Subsequently, in the first procedure, puncturing is performed with the two puncture needles 202 from a lower surface (left ventricle side) of the valve cusp 210 toward an upper surface (left atrium side), and a pad 206 is penetrated.

The artificial tendon 200 can be produced by using a synthetic resin material. Specifically, for example, Gore-tex (registered trademark) obtained by performing stretching processing of polytetrafluoroethylene and compounding the result with a polyurethane resin can be used as the artificial tendon 200. Felt or fluororesin films can be used as the pad 204 and the pad 206. The same type materials or the different type materials can be used for the pad 204 and the pad 206.

In a state where the papillary muscle 212 and the valve cusp 210 are punctured with the puncture needles 202, and the artificial tendon 200 is laid with practically no tensile force between the papillary muscle 212 and the valve cusp 210, the tendon guide portion 30 of the auxiliary instrument 100 is installed with respect to the artificial tendon 200. Specifically, as illustrated in FIG. 5A, the instrument holding portions 40 are held with fingers or the like, and the artificial tendon 200 is introduced to the tendon guide portion 30 from the side through the slit portion 12.

In the first procedure, with respect to the two straight portions of the artificial tendon 200 which is turned around at the papillary muscle 212 and is in a loop state, two auxiliary instruments 100 can be individually installed. In this state, both ends of the artificial tendon 200 are tied together, thereby forming a knot 208 on the pad 206. The process of tying the artificial tendon 200 is performed in a state where the valve cusp 210 and the papillary muscle 212 are pressed to both ends of the tendon guide portion 30 of the auxiliary instrument 100. Accordingly, as illustrated in FIG. 5B, in a state where the tendon guide portion 30 of the auxiliary instrument 100 is interposed between the valve cusp 210 and the papillary muscle 212, the length of the artificial tendon 200 is determined. Since the artificial tendon 200 formed so as to be in a loop state is turned around on the pad 204 and the pad 206, the artificial tendon 200 is restrained from intruding on the papillary muscle 212 or the tendon 214.

Next, as illustrated in FIG. 5C, the instrument holding portions 40 of the auxiliary instrument 100 are pulled outward in directions opposite to each other such that the tendon guide portion 30 is torn. Since the instrument holding portions 40 protrude radially outward from the tendon guide portion 30, in a state where the auxiliary instrument 100 is interposed between the valve cusp 210 and the papillary muscle 212, it is possible to have access to the instrument holding portions 40 from the atrium side. Since the tearing process is performed in a state where the auxiliary instrument 100 is interposed between the valve cusp 210 and the papillary muscle 212, from the viewpoint of accessibility to the instrument holding portions 40, it is favorable hold the instrument holding portions 40 by using an instrument such as tweezers. When the instrument holding portions 40 of the auxiliary instrument 100 are pulled, the auxiliary instrument 100 is torn into two portions, and the auxiliary instrument 100 is detached from the valve cusp 210 and the papillary muscle 212 so as to be separated from the side of the artificial tendon 200.

As described above, the rough surface portions 42 such as the ridged patterns are formed on the surfaces of the instrument holding portions 40. Accordingly, as illustrated in FIG. 5A, when a technician holds the instrument holding portions 40 with a thumb and an index finger, the instrument holding portions 40 can be prevented from being failed to be pinched. In addition, as in FIG. 5B, in a state where the auxiliary instrument 100 is interposed between the valve cusp 210 and the papillary muscle 212, when the instrument holding portions 40 are pinched by using an instrument (not illustrated) such as tweezers such that the auxiliary instrument 100 is torn, the instrument does not slip. Thus, the instrument holding portions 40 are held and the auxiliary instrument 100 can be thereby torn.

Figure 1B:
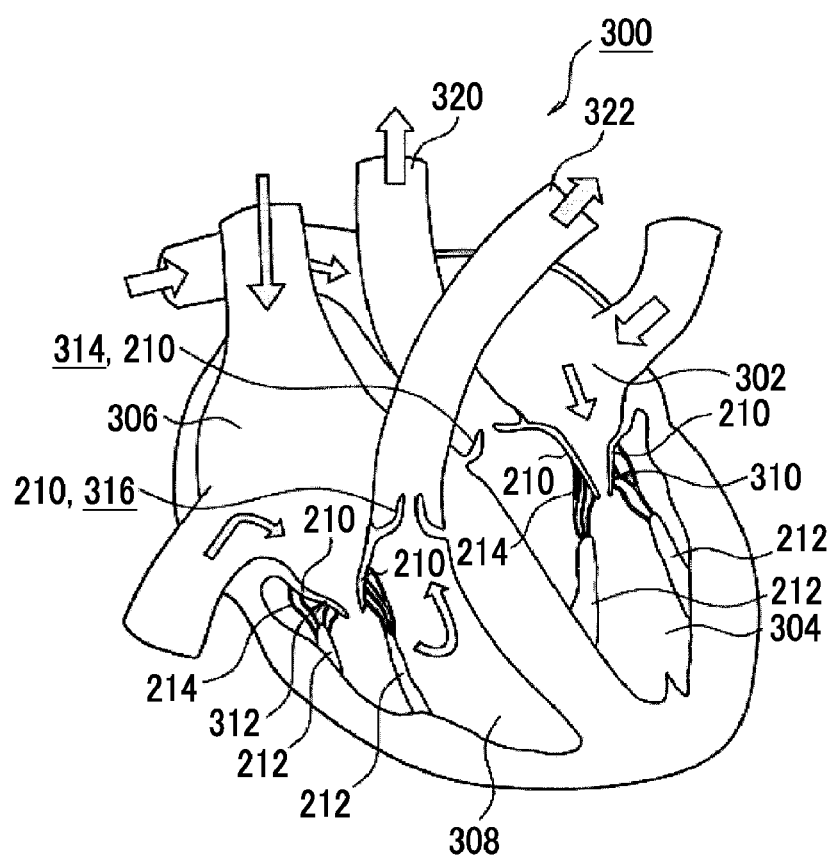
FIG. 1B is another schematic view of the heart of the human being.

As described above, the papillary muscle 212 and the valve cusp 210 are stitched with the artificial tendon 200 having a desired length substantially matching a normal tendon 214 (refer to FIGS. 1A and 1B).

Figure 6A:
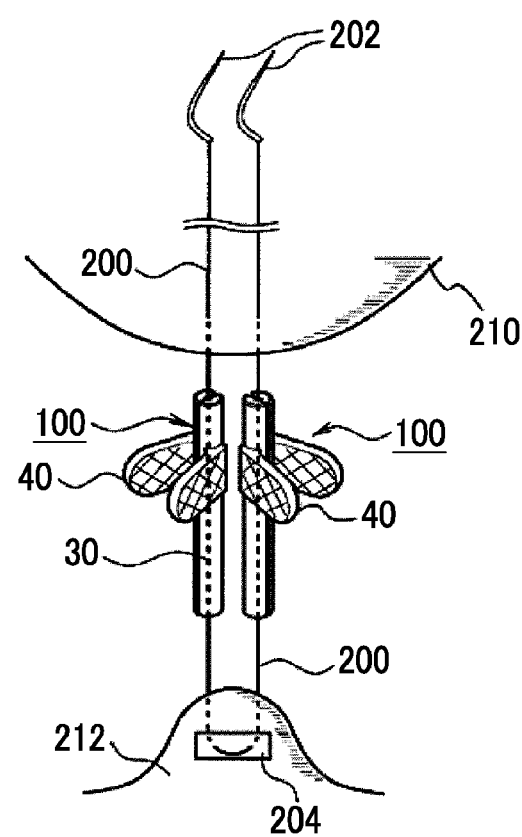
FIG. 6A is a view illustrating a modification example of a method of using the artificial tendon-forming auxiliary instrument and illustrating a state where the artificial tendon-forming auxiliary instruments are installed in the artificial tendon.
Figure 6B:
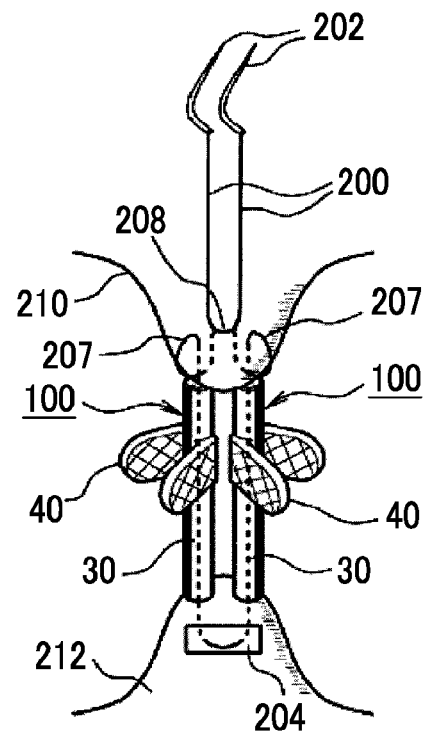
FIG. 6B is a view illustrating the modification example of the method of using the artificial tendon-forming auxiliary instrument and illustrating a state where the artificial tendon is temporarily ligated.
Figure 6C:
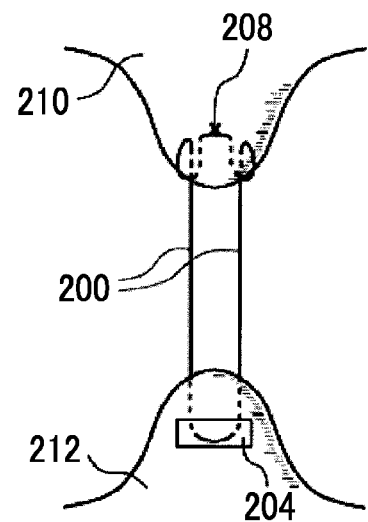
FIG. 6C is a view illustrating the modification example of the method of using the artificial tendon-forming auxiliary instrument and illustrating a state where the artificial tendon is finally ligated.

FIGS. 6A to 6C are views illustrating a modification example of the present method. FIG. 6A illustrates a state where the auxiliary instruments 100 are installed in the artificial tendon 200 with which stitching is performed across the papillary muscle 212 and the valve cusp 210. FIG. 6B illustrates a state where after the valve cusp 210 is punctured with two artificial tendons 200 a plurality of times each, the two artificial tendons 200 are tied together and the knot 208 is formed. FIG. 6C illustrates a state where the artificial tendon 200 is finally ligated.

As illustrated in FIG. 6B, the artificial tendon 200 is caused to pass through the valve cusp 210 a plurality of times (for example, twice, as illustrate) and a loop portion 207 is formed. In this case, the papillary muscle 212 and the valve cusp 210 are in a state of being pressed to both ends of the auxiliary instrument 100. Accordingly, the distance from the papillary muscle 212 to the valve cusp 210 substantially matches the length of the tendon guide portion 30. In addition, when the loop portion 207 is formed, the artificial tendon 200 is prevented from being misaligned with respect to the valve cusp 210. The knot 208 illustrated in FIG. 6B is a temporary tie in which the ends of the artificial tendon 200 are tied together only once. In other words, the artificial tendon 200 is in a temporarily ligated state with respect to the valve cusp 210. The knot 208 may be formed on the pad 206 (refer to each diagram of FIG. 5).

As illustrated in FIG. 6B, in a state where the auxiliary instrument 100 is installed in the artificial tendon 200, a backflow test for checking whether or not the artificial tendon 200 has an appropriate length is performed.

For example, the backflow test is performed by injecting a physiological saline solution into the ventricle such as the left ventricle 304 (refer to FIGS. 1A and 1B), and checking whether or not the physiological saline solution passes through a gap in the valve cusp 210 and leaks out to the atrium side.

In a case where a leak is checked, the tensile force of the artificial tendon 200 is adjusted, or the auxiliary instrument 100 is replaced. In a case of replacing the auxiliary instrument 100, as illustrated in FIG. 5C, the instrument holding portions 40 of the auxiliary instrument 100 are pulled, and the auxiliary instrument 100 is torn so as to be removed. Next, after the temporarily tied knot 208 is untied and the loop portion 207 is loosened, a new auxiliary instrument 100 is installed with respect to the artificial tendon 200 from the side (refer to FIG. 5A). Since the slit portion 12 is formed in the auxiliary instrument 100 of the present embodiment across the overall length of the tendon guide portion 30, the new auxiliary instrument 100 can be installed with respect to the artificial tendon 200 stitching the papillary muscle 212 and the valve cusp 210 (refer to FIG. 5A). It is favorable to select the new auxiliary instrument 100 having a length of the tendon guide portion 30 different from the length thereof in the previous auxiliary instrument 100 which has been torn and removed. Subsequently, the artificial tendon 200 is pulled with a predetermined tensile force, and as illustrated in FIG. 6B, the papillary muscle 212 and the valve cusp 210 are caused to be in a state of being pressed to both ends of the auxiliary instrument 100 again. Moreover, ends of the artificial tendon 200 are temporarily tied together, and the knot 208 is thereby formed. In this state, the backflow test is performed again.

In a case where no leak is checked through the backflow test, after the knot 208 is finally ligated, the auxiliary instrument 100 is torn and removed. The final ligation can be performed by making a reef knot (tight knot) or the like with the ends of the artificial tendon 200. Accordingly, as illustrated in FIG. 6C, the papillary muscle 212 and the valve cusp 210 are joined together with the artificial tendon 200 having a desired length.

As described above, the auxiliary instrument 100 of the present embodiment can be accommodated in the ventricle in a state of being installed in the artificial tendon 200. Therefore, before the auxiliary instrument 100 is torn and removed, the backflow test is performed by injecting a physiological saline solution or the like into the ventricle, and thus, a function of preventing a backflow in the valve cusp 210 can be conveniently checked. In a case where a leak is checked through the backflow test, while the papillary muscle 212 and the valve cusp 210 remain being stitched with the artificial tendon 200 without being untied therefrom, the length of the artificial tendon 200 can be appropriately adjusted by adjusting the tensile force of the artificial tendon 200 or tearing and removing the auxiliary instrument 100 so as to be replaced with the new auxiliary instrument 100. In this manner, in the auxiliary instrument 100 of the present embodiment, the instrument holding portions 40 are formed in the intermediate portion of the tendon guide portion 30, and thus, the valve cusp 210 and the papillary muscle 212 are restrained from interfering with the instrument holding portions 40 in an indwelling state. In addition, in the auxiliary instrument 100 of the present embodiment, the end-portion support portions are formed at both ends in the longitudinal direction, and there is no portion protruding to the atrium side beyond the valve cusp 210 when indwelling between the valve cusp 210 and the papillary muscle 212. Therefore, damage to the function of preventing a backflow in the valve cusp 210 while the auxiliary instrument 100 is in the indwelling state is prevented. Therefore, the backflow test can be performed while the auxiliary instrument 100 indwells inside the ventricle, and including the time for checking the function of preventing a backflow in the valve cusp 210 after an artificial tendon reconstructive operation, the entire time of the procedure can be shortened compared to that in the related art.

In addition, in the second procedure, one of the papillary muscle 212 and the valve cusp 210, preferably the papillary muscle 212 is punctured individually with the puncture needles 202 at both ends of the artificial tendon 200 and the auxiliary instrument 100 is installed with respect to the artificial tendon 200 which is turned around in a U-shaped manner. Accordingly, the artificial tendon 200 is in a state of being inserted through the tendon guide portion 30 of the auxiliary instrument 100. When the auxiliary instrument 100 is installed in the artificial tendon 200, similar to the first procedure, the instrument holding portions 40 are held with fingers or the like, and the artificial tendon 200 can be introduced to the tendon guide portion 30 from the side through the slit portion 12.

Thereafter, the papillary muscle 212 or the valve cusp 210 which is not punctured with the puncture needles 202 is punctured with the puncture needles 202 at both ends of the artificial tendon 200 in which the auxiliary instrument 100 is installed. Particularly, the valve cusp 210 is punctured from the left ventricle side to the left atrium side. Then, as illustrated in FIG. 5B, both ends of the artificial tendon 200 are tied together, and the knot 208 is formed on the pad 204 or 206. Thereafter, the procedure can be in common with the first procedure.

The second procedure can be favorably performed in a case where there is no slit portion formed from the circumferential surface 10 of the tendon guide portion 30 to the central lumen 14, as in an auxiliary instrument 105 (refer to FIGS. 10A and 10B) of a sixth embodiment (will be described later).

The auxiliary instrument 100 of the present embodiment may be provided one each as a single product or as a set having a plurality of instruments. That is, according to the present invention, there is provided an auxiliary instrument set 150 including a plurality of the artificial tendon-forming auxiliary instruments (auxiliary instruments) 100. The sizes of the tendon guide portions 30 in the longitudinal direction in the plurality of auxiliary instruments 100 included in the auxiliary instrument set 150 may be equal to each other or may be different from each other.

Figure 7:
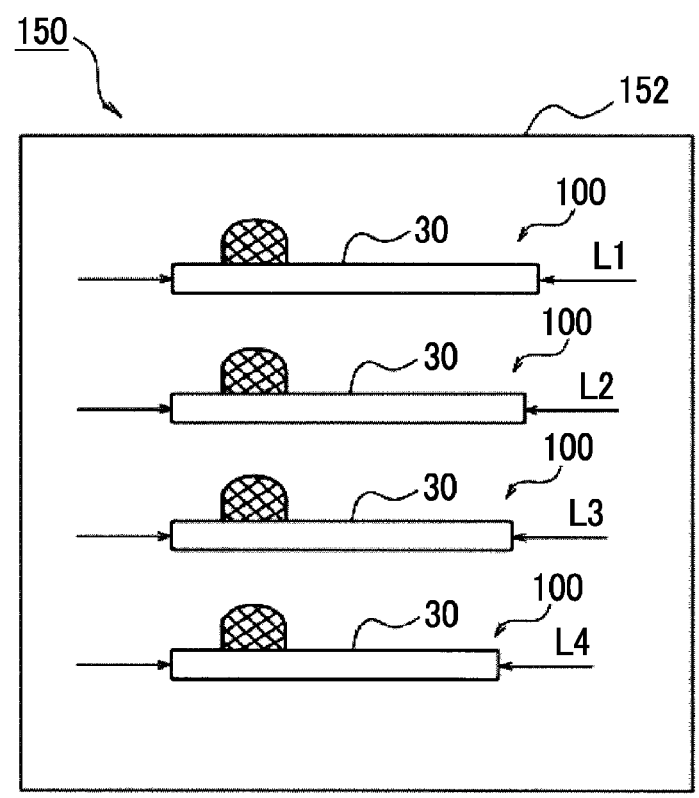
FIG. 7 is a view describing an aspect of an auxiliary instrument set.

FIG. 7 is a view describing the auxiliary instrument set 150 including the plurality of artificial tendon-forming auxiliary instruments (auxiliary instruments 100) of the present embodiment. The auxiliary instrument set 150 of the present embodiment is characterized in that sizes L1 to L4 of the tendon guide portions 30 in the longitudinal direction in the plurality of auxiliary instruments 100 are different from each other. The auxiliary instrument set 150 is provided with a sterilization container 152 which contains the plurality of auxiliary instruments 100 and is sealed.

The difference among the sizes L1 to L4 of the tendon guide portions 30 in the longitudinal direction in the plurality of auxiliary instruments 100 is N (where is an integer equal to or greater than 1) millimeters. Specifically, the sizes L1 to L4 are different from each other by one millimeter. For example, the sizes L1 to L4 can range from 13 millimeters to 16 millimeters. In this manner, when the plurality of auxiliary instruments 100 in which the sizes L1 to L4 of the tendon guide portions 30 in the longitudinal direction are different from each other are prepared, the auxiliary instrument 100 can be appropriately selected in accordance with the length of the mitral valve 310 (refer to FIGS. 1A and 1B) of a test subject. That is, prior to the procedure of the artificial tendon reconstructive operation in which the auxiliary instrument 100 of the present embodiment is used, a heart 300 of the test subject is examined through an echo examination or the like, and the length of the mitral valve 310 is estimated. It is favorable that the length of the artificial tendon 200 to be reconstructed is determined in accordance with the length of the mitral valve 310 and the auxiliary instrument 100 is selected. Therefore, it is preferable that the sizes L1 to L4 are consecutive numerical values differed from each other by one millimeter or the like.

FIG. 7 exemplifies an aspect in which the auxiliary instrument set 150 includes four auxiliary instruments 100. However, the number of auxiliary instruments 100 is not particularly limited. In addition, it is favorable that the auxiliary instrument set 150 includes the plurality of auxiliary instruments 100 in which the sizes L1 to L4 of the tendon guide portions 30 in the longitudinal direction are different from each other. That is, the auxiliary instrument set 150 may include the plurality of auxiliary instruments 100 in which the sizes of the tendon guide portions 30 in the longitudinal direction are equal to each other, for each of the sizes L1 to L4. Accordingly, when reconstruction is performed with the plurality of artificial tendons 200, it is possible to select the plurality of auxiliary instruments 100 including the tendon guide portions 30 having the same lengths as each other.

There may be provided a plurality of the auxiliary instrument sets 150. That is, a plurality of the auxiliary instrument sets 150 individually including the plurality of auxiliary instruments 100 in which the sizes L1 to L4 of the tendon guide portions 30 in the longitudinal direction are different from each other may be further prepared. It is favorable that the average values of the sizes L1 to L4 of the tendon guide portions 30 in the longitudinal direction in the plurality of auxiliary instruments 100 in the plurality of auxiliary instrument sets 150 are different from each other. Accordingly, since the sizes L1 to L4 of the tendon guide portions 30 in the longitudinal direction are prepared in a wide range, even in a case where the lengths of the mitral valves 310 are greatly different from each other in accordance with gender, age, physical build, and the like of the test subjects, it is possible to select a corresponding auxiliary instrument 100.

As an example, for example, in a first set in the plurality of auxiliary instrument sets 150, the sizes L1 to L4 range from 13 millimeters to 16 millimeters differing by one millimeter, thereby having the average value of 14.5 millimeters. In a second set, the sizes L1 to L4 range from 15 millimeters to 18 millimeters differing by one millimeter, thereby having the average value of 16.5 millimeters. In a third set, the sizes L1 to L4 range from 17 millimeters to 20 millimeters differing by one millimeter, thereby having the average value of 18.5 millimeters. In a fourth set, the sizes L1 to L4 range from 20 millimeters to 23 millimeters differing by one millimeter, thereby having the average value of 21.5 millimeters. As described above, through an echo examination or the like, with respect to a test subject whose estimated value of the length of the mitral valve 310 is comparatively short, the auxiliary instrument set 150 of the first set or the second set is selected, and the sterilization container 152 is opened. It is favorable that an auxiliary instrument 100 having optimal sizes L1 to L4 of the tendon guide portions 30 is selected from the plurality of auxiliary instruments 100 and the procedure of the artificial tendon reconstructive operation is performed. On the contrary, with respect to a test subject whose estimated value of the length of the mitral valve 310 is comparatively long, the auxiliary instrument set 150 of the third set or the fourth set is selected, and the sterilization container 152 is opened. Moreover, it is favorable that an auxiliary instrument 100 having appropriate sizes L1 to L4 is selected from the plurality of auxiliary instruments 100 included in the auxiliary instrument sets 150 and the procedure of the artificial tendon reconstructive operation is performed. In the plurality of auxiliary instruments 100 included in the opened sterilization container 152, the auxiliary instruments 100 which are not selected and are not used in the procedure are discarded. According to the auxiliary instrument set 150 of the present embodiment, with respect to many test subjects having lengths of the mitral valves 310 greatly different from each other, the auxiliary instrument 100 having appropriate sizes L1 to L4 can be prepared, and the quantity of the auxiliary instruments 100 which are not used in the procedure and are discarded can be reduced.

The present embodiment is allowed to have various types of modifications.

Figure 8A:
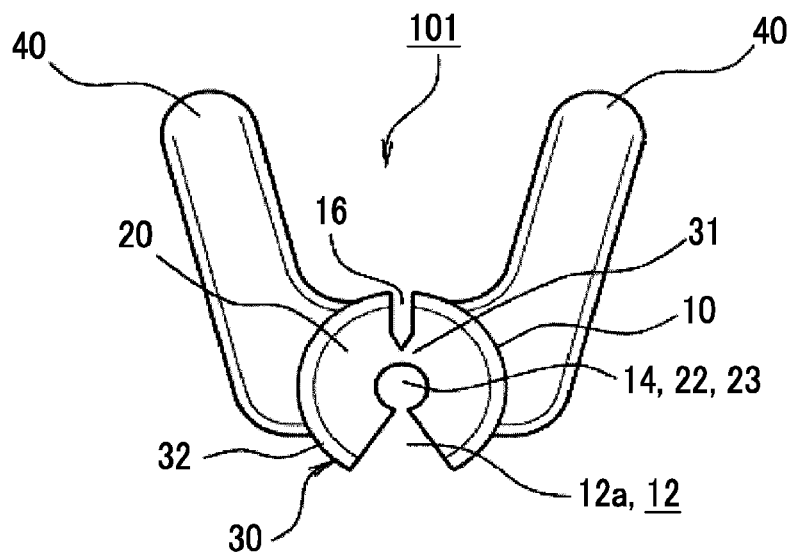
FIG. 8A is a front view of an artificial tendon-forming auxiliary instrument of a second embodiment.

FIG. 8A is a front view of an artificial tendon-forming auxiliary instrument (auxiliary instrument) 101 of a second embodiment of the present invention. The auxiliary instrument 101 of the present embodiment is different from the auxiliary instrument 100 (FIG. 3) of the first embodiment in that the wide-width portion 12a is configured and the narrow-width portion 12b is not provided. That is, in the slit portion 12 (wide-width portion 12a) of the present embodiment, the width size is monotonously reduced from the circumferential surface 10 of the tendon guide portion 30 to the central lumen 14. The wide-width portion 12a may have a linearly tapered shape in which the width size is linearly reduced toward the depth direction of the tendon guide portion 30. Otherwise, the wide-width portion 12a may have an exponentially tapered shape in which the width size is exponentially reduced in the depth direction of the tendon guide portion 30, or a radially tapered shape in which the width size is reduced in proportion to the square root of the depth from the circumferential surface 10.

Figure 8B:
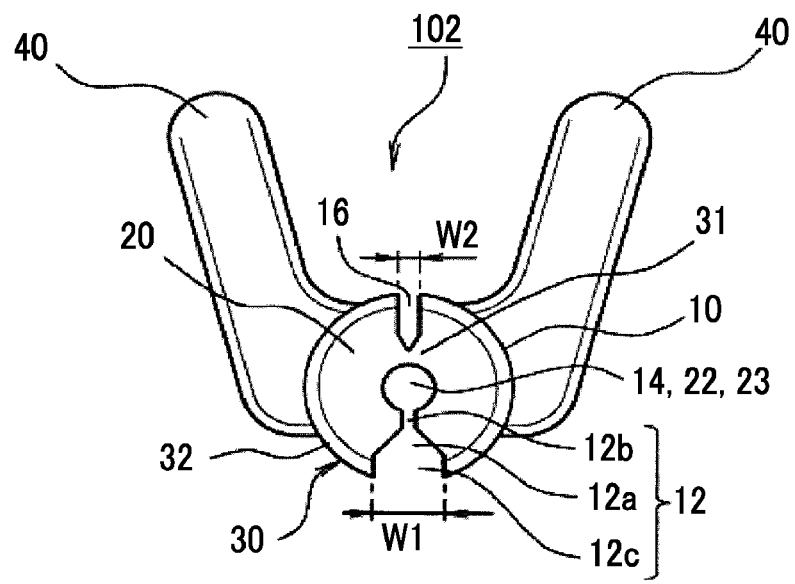
FIG. 8B is a front view of an artificial tendon-forming auxiliary instrument of a third embodiment.

FIG. 8B is a front view of an artificial tendon-forming auxiliary instrument (auxiliary instrument) 102 of a third embodiment of the present invention. The auxiliary instrument 102 of the present embodiment is different from the auxiliary instrument 100 (refer to FIG. 3) of the first embodiment in that an introduction portion 12c is continuously provided radially outward from the wide-width portion 12a. The introduction portion 12c is a portion which is open substantially at the equal width as the maximum opening width W1 of the wide-width portion 12a. The formed depth of the introduction portion 12c is smaller than the formed depth of the wide-width portion 12a. When the introduction portion 12c is formed in the circumferential surface 10 of the tendon guide portion 30, the artificial tendon 200 introduced to the slit portion 12 (introduction portion 12c) is restrained from being uncoupled from the slit portion 12. Accordingly, in the first procedure described above, the auxiliary instrument 102 can be easily installed in the artificial tendon 200 from the side.

Figure 9A:
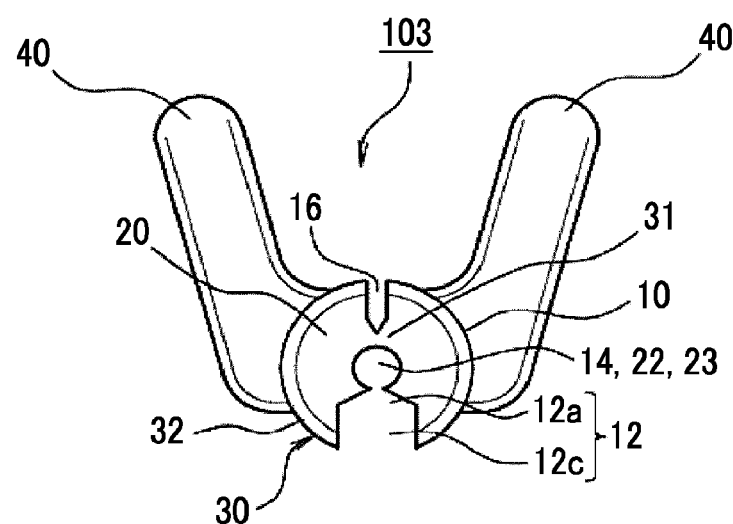
FIG. 9A is a front view of an artificial tendon-forming auxiliary instrument of a fourth embodiment.

FIG. 9A is a front view of an artificial tendon-forming auxiliary instrument (auxiliary instrument) 103 of a fourth embodiment of the present invention. The auxiliary instrument 103 of the present embodiment has a form in which the auxiliary instrument 101 (refer to FIG. 8A) of the second embodiment and the auxiliary instrument 102 (refer to FIG. 8B) of the third embodiment are combined together, and the slit portion 12 is configured with the wide-width portion 12a and the introduction portion 12c. The formed depth of the introduction portion 12c of the present embodiment is greater than the formed depth of the wide-width portion 12a. However, as the modification example of the present embodiment, the formed depth of the introduction portion 12c may be smaller than the formed depth of the wide-width portion 12a.

Figure 9B:
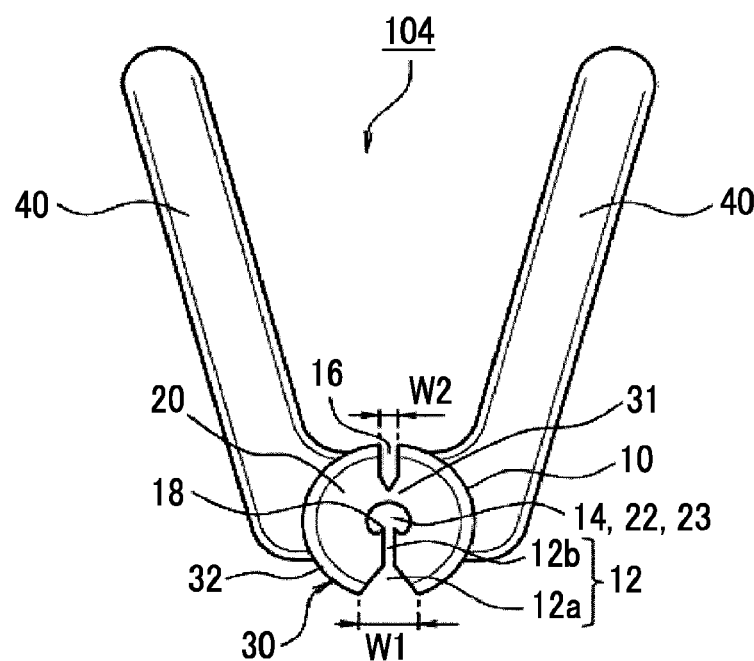
FIG. 9B is a front view of an artificial tendon-forming auxiliary instrument of a fifth embodiment.

FIG. 9B is a front view of an artificial tendon-forming auxiliary instrument (auxiliary instrument) 104 of a fifth embodiment of the present invention. The auxiliary instrument 104 of the present embodiment is different from the auxiliary instrument 100 (refer to FIG. 3) of the first embodiment in that return restriction portions 18 are included. The return restriction portions 18 are portions which restrict the artificial tendon 200 received in the central lumen 14 through the slit portion 12 such that the artificial tendon 200 is not separated from the tendon guide portion 30. When the return restriction portions 18 are formed, in a state where the artificial tendon 200 is inserted through the central lumen 14 of the auxiliary instrument 104 (refer to FIG. 5B), even if a technician releases fingers or the like from the instrument holding portions 40, the artificial tendon 200 is restrained from being separated again from the tendon guide portion 30 through the slit portion 12. Therefore, in the process in which the knot 208 is formed after the auxiliary instrument 104 is interposed between the valve cusp 210 and the papillary muscle 212, even if a technician releases fingers or the like from the instrument holding portions 40, the auxiliary instrument 104 is prevented from falling off from the artificial tendon 200.

The return restriction portions 18 are formed in any portions from the wide-width portion 12a of the slit portion 12 to the central lumen 14. In the present embodiment, as illustrated in FIG. 9B, the return restriction portions 18 are formed in a connection portion between the narrow-width portion 12b and the central lumen 14 so as to serve as acute projection-shaped reverting portions penetrating the tendon guide portion 30 toward the central lumen 14. Accordingly, the artificial tendon 200 received in the central lumen 14 is restricted such that the artificial tendon 200 does not return to the narrow-width portion 12b from the central lumen 14. Moreover, the return restriction portion 18 may be formed in the intermediate portion of the narrow-width portion 12b.

The slit portion 12 in the auxiliary instrument 104 of the present embodiment is in common with the auxiliary instrument 100 of the first embodiment in that the narrow-width portion 12b and the wide-width portion 12a are configured to be included and the introduction portion 12c (refer to FIG. 3) is not formed. However, as a modification example of the present embodiment, the introduction portion 12c may be continuously provided radially outward from the wide-width portion 12a as in the auxiliary instrument 102 of the third embodiment.

Figure 10A:
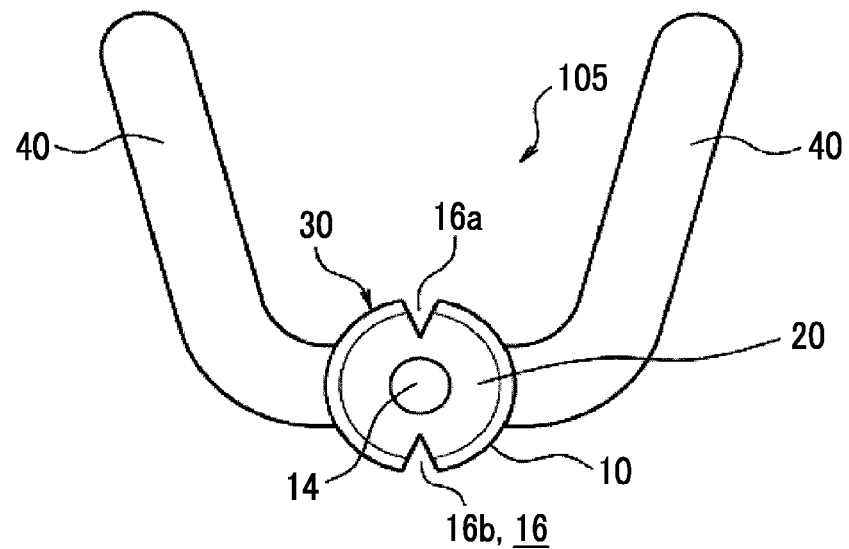
FIG. 10A is a front view of an artificial tendon-forming auxiliary instrument of a sixth embodiment.
Figure 10B:
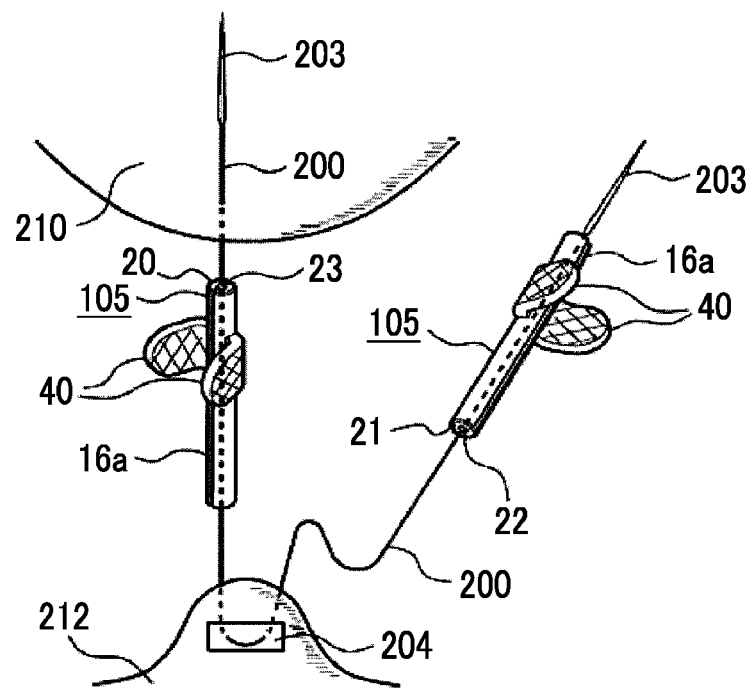
FIG. 10B is a schematic view illustrating a state where the artificial tendon-forming auxiliary instruments of the sixth embodiment are respectively installed in the artificial tendons.

FIG. 10A is a front view of an artificial tendon-forming auxiliary instrument (auxiliary instrument) 105 according to the sixth embodiment of the present invention. FIG. 10B is a schematic view illustrating a state where the artificial tendon-forming auxiliary instruments (auxiliary instruments) 105 are respectively installed in the artificial tendons 200. FIG. 10B is a view describing the second procedure mentioned above.

The auxiliary instrument 105 of the present embodiment is different from the auxiliary instrument 100 of the first embodiment in that in place of the slit portion 12 (refer to FIG. 3) formed from the circumferential surface 10 of the tendon guide portion 30 to the central lumen 14, the auxiliary instrument 105 includes a second easily-tearable portion 16b. That is, the auxiliary instrument 105 of the present embodiment includes a first easily-tearable portion 16a and the second easily-tearable portion 16b as the easily-tearable portion 16 for tearing the tendon guide portion 30, on the circumferential surface 10 of the tendon guide portion 30.

The auxiliary instrument 105 of the present embodiment is in common with the first embodiment in that the pair of instrument holding portions 40 is formed at positions biased to one end-portion support portion (in the present embodiment, the end-portion support portion 20) in the intermediate portion of the tendon guide portion 30. In addition, the auxiliary instrument 105 is in common with the first embodiment in that the pair of instrument holding portions 40 is formed on both sides so as to interpose the easily-tearable portion 16 therebetween.

When the auxiliary instrument 105 of the present embodiment is used in the procedure, as illustrated in FIG. 10B, a straight needle is used as a puncture needle 203. The diameter of the puncture needle 203 is smaller than the caliber of the opening of the central lumen 14, and the puncture needle 203 can be inserted through the central lumen 14. The second procedure is different from the first procedure (refer to FIGS. 5A to 5C) using the auxiliary instrument 100 of the first embodiment in that in a state where the puncture needle 203 penetrates the first tendon insertion port 22 of the end-portion support portion 20 and the artificial tendon 200 is inserted through the auxiliary instrument 105, the valve cusp 210 is punctured with the puncture needle 203. That is, in the auxiliary instrument 105 of the present embodiment, the artificial tendon 200 is inserted through from the end portion along the longitudinal direction. Thereafter, the valve cusp 210 is punctured with the puncture needle 203.

In a state where the auxiliary instrument 105 is interposed between the papillary muscle 212 and the valve cusp 210, both ends of the artificial tendon 200 are tied together. Thereafter, the pair of instrument holding portions 40 of the auxiliary instrument 105 is pulled outward in directions opposite to each other such that the auxiliary instrument 105 is broken. In this case, since both the first easily-tearable portion 16a and the second easily-tearable portion 16b are broken, similar to the aspect illustrated in FIG. 5C, the auxiliary instrument 105 is broken into two portions and can be detached from the artificial tendon 200.

As in the auxiliary instrument 105 of the present embodiment, when no slit portion 12 is formed and the puncture needle 203 is introduced in the longitudinal direction through the first tendon insertion port 22 of the end-portion support portion 20, before the auxiliary instrument 105 is broken, the artificial tendon 200 does not unexpectedly fall off from the auxiliary instrument 105.

Figure 11A:
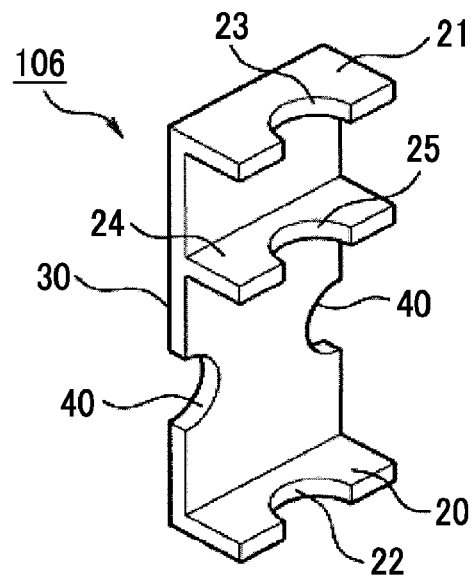
FIG. 11A is a perspective view of an artificial tendon-forming auxiliary instrument according to a seventh embodiment.
Figure 11B:
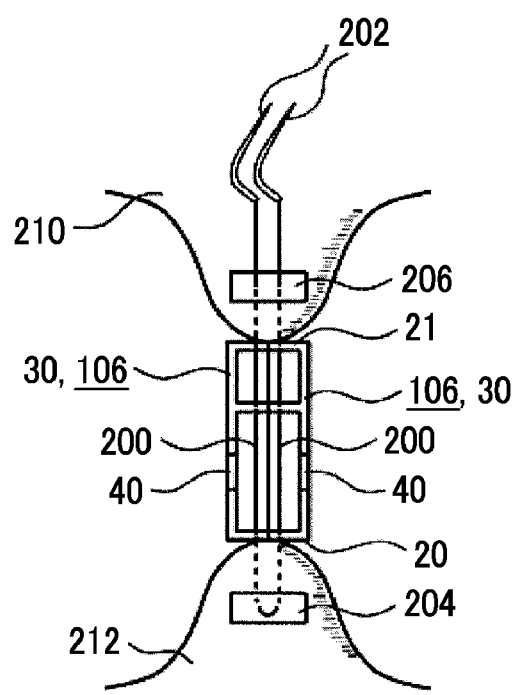
FIG. 11B is a schematic view illustrating a state where the artificial tendon-forming auxiliary instrument of the seventh embodiment is installed in the artificial tendon.

FIG. 11A is a perspective view of an artificial tendon-forming auxiliary instrument (auxiliary instrument) 106 according to the seventh embodiment of the present invention. FIG. 11B is a schematic view illustrating a state where the artificial tendon-forming auxiliary instrument (auxiliary instrument) 106 is installed in the artificial tendon 200.

The auxiliary instrument 106 of the present embodiment is different from the first embodiment in that the auxiliary instrument 106 has a half-split tubular shape. The first tendon insertion port 22 and the second tendon insertion port 23 have semicircular shapes. When a pair of the auxiliary instruments 106 faces each other and is combined, the first tendon insertion port 22 and the second tendon insertion port 23 having circular shapes are formed.

The tendon guide portion 30 of the auxiliary instrument 106 has a plate shape. The end-portion support portion 20 is formed at the lower end in the longitudinal direction (vertical direction in FIG. 11A), and the end-portion support portion 21 is formed at the upper end. The end-portion support portion 20 and the end-portion support portion 21 protrude in a direction orthogonal to the tendon guide portion 30. The first tendon insertion port 22 is formed at the tip of the end-portion support portion 20 and the second tendon insertion port 23 is formed at the tip of the end-portion support portion 21 so as to be individually cut and to have a semicircular shape.

The instrument holding portions 40 are provided in the intermediate portions of the tendon guide portion 30 in the longitudinal direction. The instrument holding portions 40 of the present embodiment are recessed portions respectively formed on both sides facing each other in the width direction of the plate-shaped tendon guide portion 30, and a technician can hold the tendon guide portion 30 by hooking fingers or the like.

An intermediate bumper plate 24 is formed in the intermediate portion of the tendon guide portion 30 in the longitudinal direction so as to protrude in the same direction as the end-portion support portion 20 and the end-portion support portion 21. An intermediate tendon insertion port 25 is formed at the tip of the intermediate bumper plate 24 so as to be cut and to have a semicircular shape. Accordingly, as illustrated in FIG. 11B, when the pair of auxiliary instruments 106 are disposed so as to face each other, at joint portions between the auxiliary instruments 106, three circular openings, that is, the first tendon insertion port 22, the intermediate tendon insertion port 25, and the second tendon insertion port 23 are coaxially arranged. The two straight portions of the artificial tendon 200 which stitches the papillary muscle 212 and is formed in a loop state are inserted through the three circular openings and are straightly guided inside the tendon guide portion 30.

Similar to the first embodiment, the auxiliary instrument 106 of the present embodiment can be installed from the side with respect to the artificial tendon 200 with which the papillary muscle 212 and the valve cusp 210 are stitched in advance. Therefore, as illustrated in FIG. 11B, curved needles can be used as the puncture needles 202. After both ends of the artificial tendon 200 are tied together, a pair of auxiliary instruments 106 is detached from the artificial tendon 200. Accordingly, the papillary muscle 212 and the valve cusp 210 are joined together with the artificial tendon 200 having a desired length. As illustrated in FIG. 11B, in a state where a pair of auxiliary instruments 106 faces each other, an interlock portion (not illustrated) for interlocking the auxiliary instruments 106 with each other may be provided in any one or more of the end-portion support portion 20, the intermediate tendon insertion port 25, and the end-portion support portion 21.

The present invention is not limited to the embodiments described above and includes aspects such as various types of modifications and improvements as long as the objects of the present invention are achieved.

In addition, various types of the configuration elements of the artificial tendon-forming auxiliary instrument of the present invention do not necessarily exist in an individually independent manner. It is allowed to form a plurality of the configuration elements with one member, to form one configuration element with a plurality of members, to have a certain configuration element so as to serve as a part of a different configuration element, to have a part of a configuration element so as to overlap a part of a different configuration element, and the like.

Figure 12A:
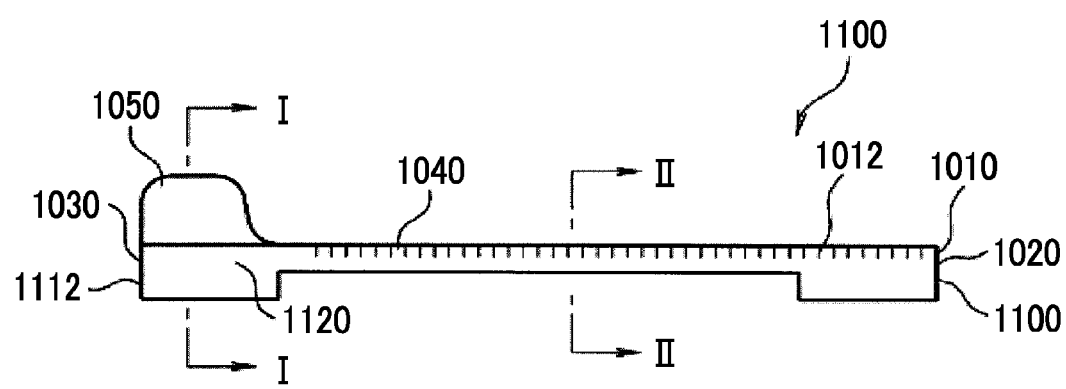
FIG. 12A is a side view of a somatometry instrument of an eighth embodiment of the present invention.
Figure 12B:
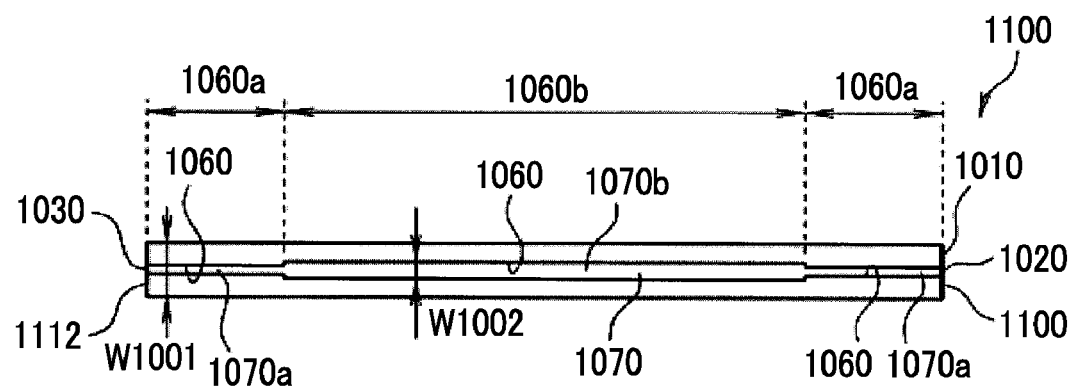
FIG. 12B is a rear view of the somatometry instrument.
Figure 12C:
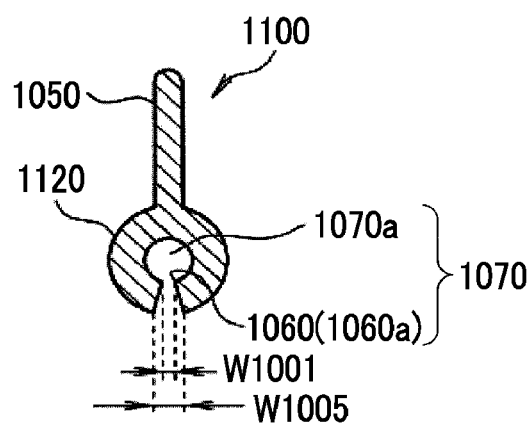
FIG. 12C is a cross-sectional view taken along line I-I in FIG. 12A.
Figure 12D:
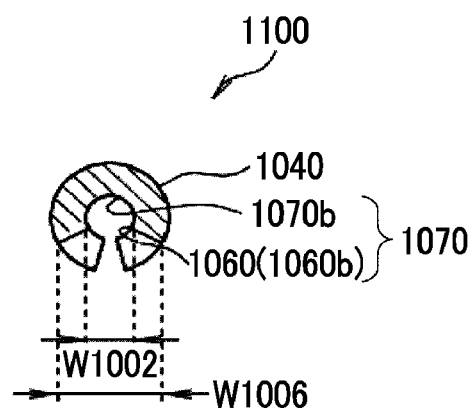
FIG. 12D is a cross-sectional view taken along line II-II in FIG. 12A.
Figure 13A:
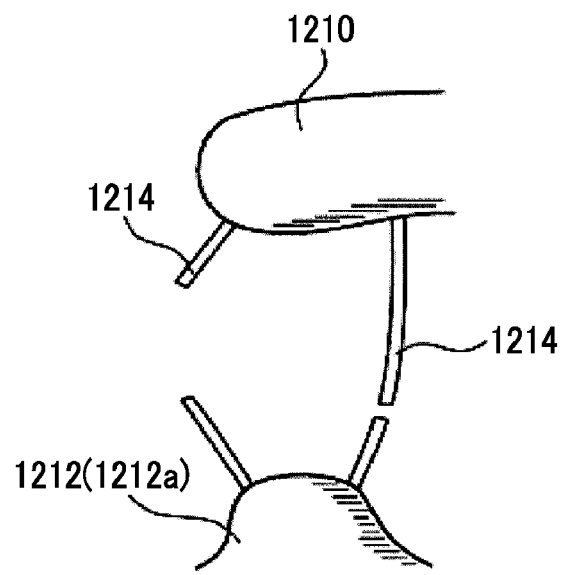
FIG. 13A is a schematic view illustrating a state where an abnormality occurs in a tendon which joins a valve cusp and a papillary muscle together.
Figure 13B:
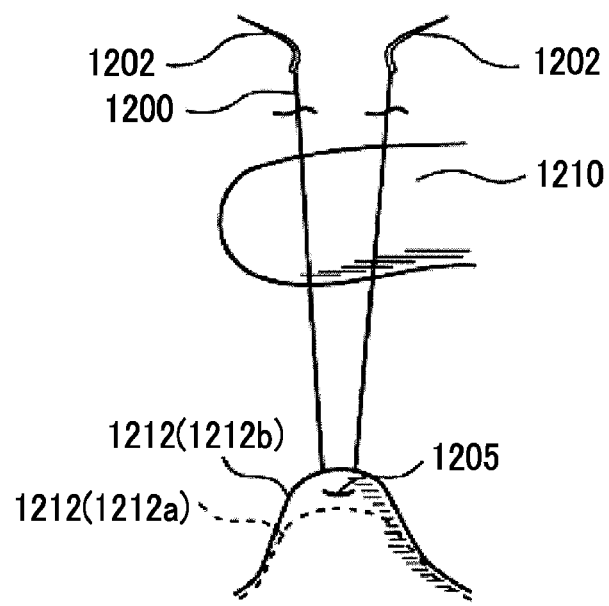
FIG. 13B is a schematic view illustrating a state where the papillary muscle is stitched with an artificial thread.
Figure 13C:
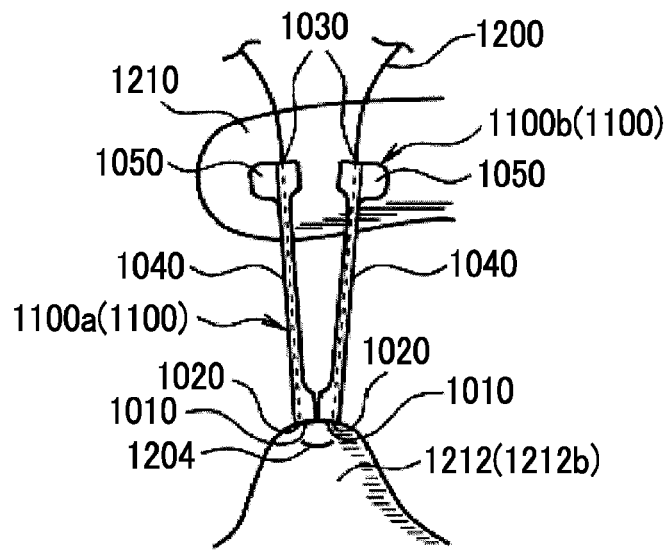
FIG. 13C is a schematic view illustrating a state where the somatometry instrument of the eighth embodiment is installed in the artificial thread stitching the papillary muscle.
Figure 13D:
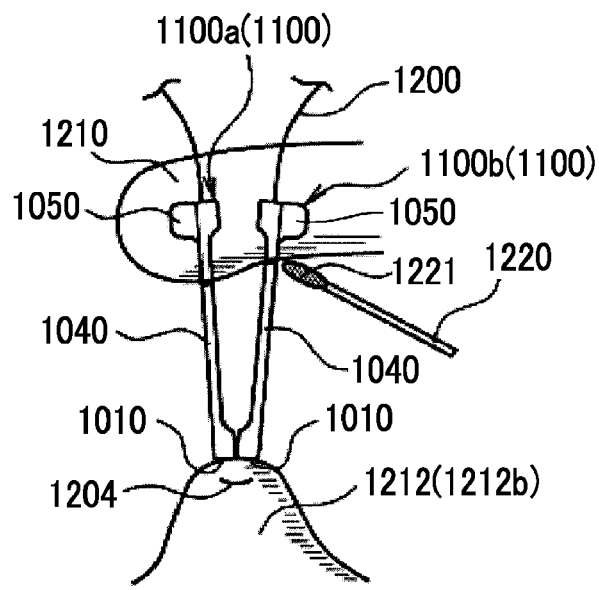
FIG. 13D is a schematic view illustrating a state where a distance between the papillary muscle and the valve cusp is measured with the somatometry instrument of the eighth embodiment.
Figure 14A:
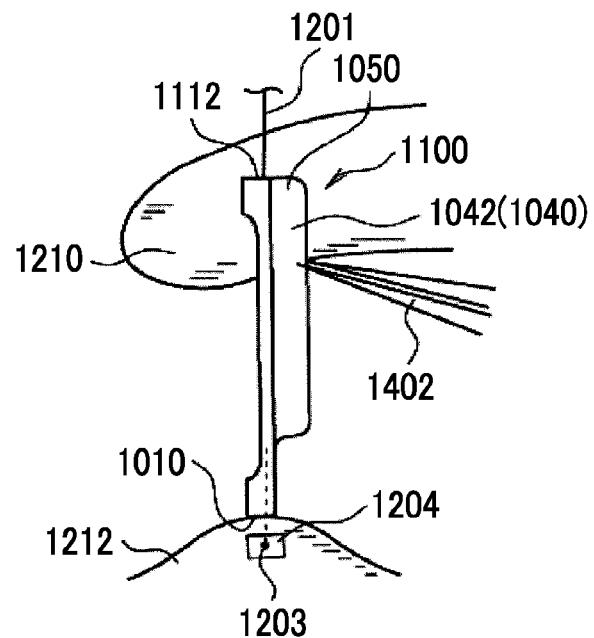
FIG. 14A is a side view illustrating a modification example of the somatometry instrument of the eighth embodiment.
Figure 14B:
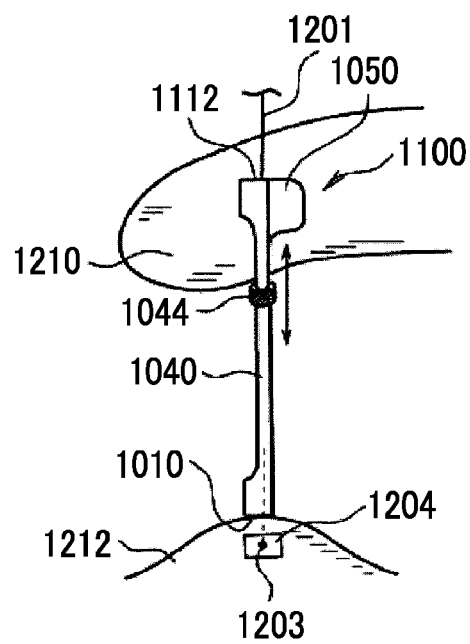
FIG. 14B is a side view illustrating the modification example of the somatometry instrument of the eighth embodiment.

FIG. 12A is a side view of a somatometry instrument 1100 of an eighth embodiment of the present invention. FIG. 12B is a rear view of the somatometry instrument 1100. FIG. 12C is a cross-sectional view taken along line I-I in FIG. 12A. FIG. 12D is a cross-sectional view taken along line II-II in FIG. 12A. FIG. 13A is a schematic view illustrating a state where an abnormality occurs in a tendon 1214 which joins a valve cusp 1210 and a papillary muscle 1212 together. FIG. 13B is a schematic view illustrating a state where the papillary muscle 1212 is stitched with an artificial thread (artificial tendon 1200). FIG. 13C is a schematic view illustrating a state where the somatometry instrument 1100 of the eighth embodiment is installed in the artificial thread (artificial tendon 1200) stitching the papillary muscle 1212. FIG. 13D is a schematic view illustrating a state where a distance between the papillary muscle 1212 and the valve cusp 1210 is measured with the somatometry instrument 1100 of the eighth embodiment. FIGS. 14A and 14B are side views illustrating a modification example of the somatometry instrument 1100 of the eighth embodiment.

First, the outline of the somatometry instrument 1100 of the present embodiment will be described.

The somatometry instrument 1100 is a somatometry instrument which measures a distance between a first site inside a living body, and a second site physically separated from the first site. In the somatometry instrument 1100, an end-portion abutment portion 1010 which is able to abut on the first site is provided at one end 1110 of the somatometry instrument 1100 in the longitudinal direction. In addition, the somatometry instrument 1100 includes a first insertion port 1020 which is provided in the end-portion abutment portion 1010 and through which the artificial thread stitching the first site is inserted; a draw-out portion (second insertion port 1030) which is provided at an opposite end 1112 facing the end-portion abutment portion 1010 in the longitudinal direction or at an intermediate portion that is an intermediate region between the end-portion abutment portion 1010 and the opposite end 1112, and through which the artificial thread inserted through the first insertion port 1020 is drawn out in an outward direction of the somatometry instrument; and a measurement portion 1040 which is provided in the intermediate portion and measures the distance between the first site and the second site.

As illustrated in FIG. 13C, in the somatometry instrument 1100, in a state where the artificial thread (artificial tendon 1200) is inserted through the first insertion port 1020 and the second insertion port 1030, the end-portion abutment portion 1010 can abut on the first site (papillary muscle 1212). In this state, the artificial thread (artificial tendon 1200) inserted through the first insertion port 1020 and the second insertion port 1030 is operated, or a holding portion 1050 is held. Then, the somatometry instrument 1100 is oriented in an appropriate direction, and the end-portion abutment portion 1010 is temporarily fixed to the first site (papillary muscle 1212). While the temporarily fixed state is maintained, the oriented direction of the somatometry instrument 1100 is adjusted such that the longitudinal direction of the somatometry instrument 1100 becomes substantially parallel to a straight direction connecting the first site (papillary muscle 1212) and the second site (valve cusp 1210) together. Then, the position of the second site (valve cusp 1210) is measured with the measurement portion 1040, and the distance between the first site (papillary muscle 1212) and the second site (valve cusp 1210) can be thereby accurately measured.

In the description below, there are cases where a process in which the end-portion abutment portion 1010 abuts on the first site (papillary muscle 1212), the somatometry instrument 1100 is oriented in an appropriate direction, and the position of the end-portion abutment portion 1010 is temporarily fixed is simply referred to as temporary fixing. Here, causing the somatometry instrument 1100 to be oriented in an appropriate direction denotes that the somatometry instrument 1100 is oriented such that the straight direction connecting the first site (arbitrary spot in the papillary muscle 1212) and the second site (arbitrary spot in the valve cusp 1210) together is substantially parallel to the longitudinal direction. The straight direction does not denote any particular direction which is particularly limited. The straight direction denotes a schematic direction connecting two points scheduled for a measurement of the distance.

In the present embodiment, a measurement broadly includes an aspect in which the distance between the first site and the second site can be directly or indirectly grasped. More specifically, the measurement includes an aspect in which the distance between the first site and the second site is directly measured inside a living body, and an aspect in which the position of the second site is recorded in the measurement portion in the temporarily fixed state as described above and a distance between the recorded spot and the end-portion abutment portion 1010 is measured afterward.

In the present invention, in a case of not being otherwise specified, the longitudinal direction denotes the longitudinal direction of the somatometry instrument 1100. In addition, in regard to the somatometry instrument 1100, the one end and the opposite end denote end portions in the longitudinal direction. End-portion regions denote predetermined regions including the end portions and extending in the longitudinal direction. The intermediate portion denotes a region between end-portion regions in the longitudinal direction.

Next, the present embodiment will be described in detail. In the description below, the present invention will be described by exemplifying a case where a distance between the valve cusp 1210 and the papillary muscle 1212 scheduled for treatment is measured in advance, in order to suitably determine the length of an artificial tendon-forming auxiliary instrument to be used in MVP. In addition, the artificial thread mentioned in regard to the present invention is a filamentous material which can suture a living body. Examples of the artificial thread include a suture thread and an artificial tendon. However, the artificial thread is not limited thereto.

In the description regarding the present embodiment below, the second site is the valve cusp 1210 of a cardiac valve, and the first site is the papillary muscle 1212 which is positioned on a downstream side in a normal blood flow direction with respect to the valve cusp 1210. In addition, the artificial thread is the artificial tendon 1200.

In this manner, according to the present embodiment, in a tunnel visioned spot inside a living body, for example, inside the heart, the distance between two places physically separated from can be accurately measured. However, the following description does not limit any of the first site, the second site, and the artificial thread in the present embodiment.

For example, the somatometry instrument 1100 can be produced by using a soft resin material such as a soft vinyl chloride resin, a polyurethane resin, and a silicone resin. Accordingly, in a case where the somatometry instrument 1100 is used inside a living body, biological tissue coming into contact with the somatometry instrument 1100 is not damaged. Only a predetermined spot in the somatometry instrument 1100, for example, the holding portion 1050 described below can be produced by using a different member. In the present embodiment, the somatometry instrument 1100 in its entirety including the holding portion 1050 is integrally molded by using one material. Accordingly, a particular portion such as the holding portion 1050 is not unexpectedly separated from the somatometry instrument 1100, and the manufacturing process and the number of components can be reduced. For example, the somatometry instrument 1100 can be produced through injection molding of a thermoplastic soft resin material.

The somatometry instrument 1100 has the first insertion port 1020 and the draw-out portion (second insertion port 1030). The artificial tendon 1200 having the somatometry instrument 1100 installed therein is inserted through the open-shaped first insertion port 1020 and is drawn out in the outward direction through the draw-out portion (second insertion port 1030). In the present embodiment, the draw-out portion is the open-shaped second insertion port 1030 provided at the opposite end 1112.

The draw-out portion is a portion for drawing out the artificial thread in the outward direction of the somatometry instrument in a state where the somatometry instrument is installed with respect to the artificial thread. In the present embodiment, the draw-out portion is the second insertion port which is provided at the opposite end 1112 and allows the artificial thread (artificial tendon 1200) to be inserted therethrough, thereby drawing out the artificial thread in the outward direction of the somatometry instrument 1100.

As illustrated in FIG. 12A, the somatometry instrument 1100 has the holding portion 1050 for holding the somatometry instrument 1100. The holding portion 1050 is provided at a position biased to the opposite end 112 in the longitudinal direction.

The holding portion 1050 is a portion for holding the somatometry instrument 1100 with fingers of a technician, tweezers, or the like (hereinafter, will be also simply referred to as fingers or the like). When the holding portion 1050 is included, the somatometry instrument 1100 can be easily supported within a limited space inside a living body, and operability of the somatometry instrument 1100 is improved.

The holding portion 1050 in the present embodiment is formed so as to have a one-plate shape protruding outward from the outer circumference of the somatometry instrument 1100. However, the shape of the holding portion 1050 is not limited thereto. For example, the holding portion 1050 may be a groove which is formed in the circumferential direction at a predetermined position in the outer circumference of the somatometry instrument 1100, that is, a recessed portion (illustration omitted) in which pointed ends of tweezers can be fitted.

If the holding portion 1050 is provided at a position biased to the opposite end 1112, when the distance between the papillary muscle 1212 and the valve cusp 1210 is measured by causing the end-portion abutment portion 1010 to abut on the papillary muscle 1212 and checking the position of the valve cusp 1210, the holding portion 1050 is restrained from interfering with the measuring work (refer to FIG. 13D). From such a viewpoint, as illustrated in FIG. 12A, it is more preferable that the holding portion 1050 is provided in the end-portion region of the somatometry instrument 1100.

The end-portion abutment portion 1010 in the present embodiment is formed so as to have a plane shape, and it is considered that the papillary muscle 1212 is not damaged when the end-portion abutment portion 1010 abuts on the papillary muscle 1212. The end-portion abutment portion 1010 may have a flat plane shape or a curved plane shape.

As illustrated in FIGS. 12A to 12D, the somatometry instrument 1100 of the present embodiment is provided with an artificial thread guidance portion 1070 extending in the longitudinal direction across the first insertion port 1020 and the draw-out portion (second insertion port 1030). Accordingly, the insertion state of the artificial tendon 1200 (refer to FIG. 13C) which is inserted through the first insertion port 1020 and the second insertion port 1030 can be stabilized. FIG. 13C illustrates a state where the artificial thread guidance portion 1070 is inserted through the first insertion port 1020 and the second insertion port 1030 and is guided to the artificial thread guidance portion 1070 (illustration omitted).

Here, the term "guided" denotes that movement of the artificial tendon 1200 in at least a part of a direction orthogonal to the longitudinal direction of the somatometry instrument 1100 is restricted.

As an example of the somatometry instrument 1100 including the artificial thread guidance portion 1070, it is possible to exemplify an aspect (illustration omitted) provided with a central lumen which is in a hollow tubular shape, in which an end-portion opening on one side is the first insertion port 1020 and an end-portion opening on the other side is the second insertion port 1030, and which connects both the end-portion openings together. The aspect is not limited to a case where the somatometry instrument 1100 in its entirety has the hollow tubular shape. The somatometry instrument 1100 can partially have a hollow tubular shape including a central lumen which communicates with the outside in the longitudinal direction such that the central lumen functions as the artificial thread guidance portion 1070.

As illustrated in FIG. 12B, the second insertion port 1030 in the present embodiment is provided at the opposite end 1112. That is, the somatometry instrument 1100 of the present embodiment has an elongated shape, and the first insertion port 1020 and the second insertion port 1030 are respectively provided at the one end 1110 and the opposite end 1112. Accordingly, when the artificial tendon 1200 inserted through the first insertion port 1020 and the second insertion port 1030 is operated, the longitudinal direction of the somatometry instrument 1100 in its entirety is easily oriented in a desired direction. However, this is an example of the present invention, and an aspect in which the second insertion port 1030 is provided in a spot other than the opposite end 1112 is not excluded. For example, the second insertion port 1030 can be provided in an arbitrary spot in the intermediate portion of the somatometry instrument 1100 (illustration omitted).

Incidentally, as illustrated in FIG. 13B, there are cases where the artificial thread such as the artificial tendon 1200 used with respect to the somatometry instrument 1100 is provided with curved puncture needles 1202 in both end portions. In such a case, there are cases where it is physically difficult to cause the puncture needles 1202 to pass through the first insertion port 1020, the second insertion port 1030, and the artificial thread guidance portion 1070.

In such a case, it is favorable that the artificial thread guidance portion 1070 is provided with an opening portion 1060 (refer to FIG. 12B) which is continuously open across the longitudinal direction with an opening width capable of receiving the artificial thread (artificial tendon 1200). Accordingly, the opening portion 1060 can be installed with respect to the artificial thread guidance portion 1070 along the opening portion 1060 and can be uncoupled from the artificial thread guidance portion 1070 along the opening portion 1060.

Specifically, as illustrated in FIG. 13B, the opening portion 1060 encounters the artificial thread (artificial tendon 1200) stitching the papillary muscle 1212, that is, the first site inside a living body, and the artificial thread guidance portion 1070 can be thereby installed.

Even with the artificial thread (artificial tendon 1200) having no curved puncture needle 1202, threading work of causing a thread to pass through a cavity having a small diameter is troublesome. On the contrary, when the opening portion 1060 is provided, the threading work can be omitted. As illustrated in FIG. 12B, the opening portion 1060 in the present embodiment substantially and straightly extends between the first insertion port 1020 and the second insertion port 1030. As a modification example (illustration omitted), at least a part of the opening portion 1060 may extend in a direction intersecting the longitudinal direction. Accordingly, the artificial tendon 1200 which is inserted through the first insertion port 1020 and the second insertion port 1030 and is disposed in the artificial thread guidance portion 1070 can pass through the opening portion 1060 and can be unlikely to be separated from the somatometry instrument 1100. More specifically, for example, the opening portion 1060 can be spirally formed across the first insertion port 1020 and the second insertion port 1030. In addition, the opening portion 1060 may have a straight portion with respect to the longitudinal direction and a spiral portion or a curved portion, between the first insertion port 1020 and the second insertion port 1030.

As illustrated in FIG. 12B, in the somatometry instrument 1100 of the present embodiment, the draw-out portion (second insertion port 1030) is provided at the opposite end 1112. As referred to in FIG. 12C, the opening portion 1060 is configured such that a minimum opening width observed in a cut surface which is cut in a direction orthogonal to the longitudinal direction becomes greater in the intermediate portion than in both the end-portion regions in the longitudinal direction. Here, the minimum opening width denotes the minimum width size of the opening portion 1060 observed in the cut surface.

More specifically, as illustrated in FIG. 12C, the minimum opening width of the opening portion 1060 in the end-portion region of the somatometry instrument 1100 is W1001, and as illustrated in FIG. 12D, the minimum opening width of the opening portion 1060 in the intermediate portion of the somatometry instrument 1100 is W1002. Here, the somatometry instrument 1100 in the present embodiment has a relationship of the minimum opening width W1001<the minimum opening width W1002. The end-portion region forms a narrow width region 1060a having the minimum opening width W1001, and the intermediate portion forms a wide width region 1060b having a relatively great width size, that is, the minimum opening width W1002. As illustrated in FIGS. 12C and 12D, the narrow width region 1060a and the wide width region 1060b are easily observed through a cross section. For example, the minimum opening width W1002 is sufficiently greater than the diameter (wire diameter) of the artificial tendon 1200. In addition, for example, the minimum opening width W1001 has a size approximately the same as the diameter (wire diameter) of the artificial tendon 1200 or a size equal to or smaller than that of the artificial tendon 1200.

In this manner, when the opening portion 1060 has the narrow width region 1060a, a state where the artificial tendon 1200 is installed in the somatometry instrument 1100 can be favorably maintained, and the artificial tendon 1200 is prevented from being imprudently separated from the somatometry instrument 1100 during the procedure.

In addition, since the artificial tendon 1200 is smoothly separated from the wide width region 1060b by passing through the narrow width region 1060a radially outward, work of detaching the artificial tendon 1200 from the somatometry instrument 1100 is easily performed, and the load applied to the artificial tendon 1200 at the time of detaching is small.

The present embodiment exemplifies a case where the opening width of the opening portion 1060 observed in a cross section is not uniform. However, the embodiment does not exclude an exemplary aspect in which the opening width of the opening portion 1060 is uniform. The somatometry instrument 1100 includes a case where the opening width of the opening portion 1060 is uniform in any cross section in the longitudinal direction, and a case where the opening width of any one of the end-portion region or the intermediate portion in the longitudinal direction is the equal width.

In a case where the opening width of the opening portion 1060 observed in a cross section is the equal width, the opening width having the equal width (that is, a uniform opening width observed in a cross section) is recognized as the minimum opening width in the cross section thereof, and a size relationship between the minimum opening width W1001 and the minimum opening width W1002 described above is determined.

In addition, FIG. 12D illustrates an example in which the opening width continuously increases from the minimum opening width W1002 toward the outer circumferential opening width W1006. However, for example, an aspect in which the opening width discontinuously increases from the minimum opening width W1002 toward the outer circumferential opening width W1006 (illustration omitted) may be adopted. More specifically, a recessed portion 1070b may be a recessed portion which is open 180 degrees, has a discontinuous step from the opening end portion of the recessed portion in the lateral direction on the sheet (that is, a direction perpendicular to the opening side on the sheet), and is open with the equal width from the step toward the outer circumference (illustration omitted). In this case, the opening width of the opening of the recessed portion becomes the minimum opening width W1002, and the opening width having the equal width open from the step toward the outer circumference becomes the outer circumferential opening width W1006.

As described above, in the somatometry instrument 1100, the draw-out portion (second insertion port 1030) is provided at the opposite end, and as illustrated in FIGS. 12C and 12D, the outer circumferential opening width of the opening portion 1060 (outer circumferential opening width W1005 and outer circumferential opening width W1006) observed from the outer circumference side of the somatometry instrument 1100 is configured to be greater in the intermediate portion than in both the end-portion regions in the longitudinal direction. That is, the outer circumferential opening width W1006 in the intermediate portion is greater than the outer circumferential opening width W1005 in the end-portion region. Therefore, when the artificial tendon 1200 passes through the outer circumferential opening width W1005, the artificial tendon 1200 can easily pass through the outer circumferential opening width W1006, and the somatometry instrument 1100 can be thereby smoothly installed with respect to the artificial tendon 1200.

As a modification example (illustration omitted), the artificial thread guidance portion 1070 may have a half-split cylindrical intermediate portion which continues in the longitudinal direction.

In the end-portion region in the longitudinal direction, the artificial thread guidance portion 1070 in the present embodiment has a through hole 1070a which penetrates the somatometry instrument 1100 longer than the diameter (outer diameter) of the one end 1110 or the opposite end 1112 in the longitudinal direction and is open through the opening portion 1060 which allows the artificial thread (artificial tendon 1200) to pass through toward the side of the somatometry instrument 1100 so as to be attachable and detachable. For example, the through hole 1070a in the present embodiment is formed to have a substantially circular shape in a front view.

In addition, the artificial thread guidance portion 1070 continues in the longitudinal direction in the intermediate portion and forms the arc-shaped recessed portion 1070b in a cross section. The recessed portion 1070b is open on the side through the opening portion 1060b.

The through hole 1070a restricts movement of the artificial tendon 1200 substantially in four directions excluding the opening portion 1060. In addition, the recessed portion 1070b allows movement of the artificial tendon 1200 in a direction of the opening portion 1060 and restricts movement of the artificial tendon 1200 in directions other than the direction of the opening portion 1060.

As modification examples of the artificial thread guidance portion 1070 (illustration omitted), it is possible to exemplify a plate-shaped artificial thread guidance portion 1070 which has a predetermined width size and extends in the longitudinal direction, and a half-split cylindrical artificial thread guidance portion 1070 which continues in the longitudinal direction. When the artificial tendon 1200 is disposed along the plate-shaped artificial thread guidance portion 1070, movement of the artificial tendon 1200 toward the plate-shaped member side can be restricted. In addition, when the artificial tendon 1200 is disposed along the half-split cylindrical inner circumferential surface, movement of the artificial tendon 1200 can be similarly restricted.

As understood in FIGS. 12B and 12C, an outer circumferential surface 1120 in the narrow width region 1060a of the somatometry instrument 1100 forms a substantially cylindrical surface excluding the holding portion 1050. The slit-shaped opening portion 1060 is formed along the central axis (axis in the longitudinal direction) so as to be cut in the radial direction of the somatometry instrument 1100 at a depth from the outer circumferential surface 1120 to the through hole 1070a.

The wide width region 1060b of the somatometry instrument 1100 has the recessed portion 1070b which is open wider than the narrow width region 1060a (refer to FIG. 12D). The through hole 1070a in the narrow width region 1060a, and the recessed portion 1070b in the wide width region 1060b are connected to each other in the longitudinal direction, thereby configuring the artificial thread guidance portion 1070. As illustrated in FIGS. 12C and 12D, specifically in the somatometry instrument 1100 of the present embodiment, relationships of the minimum opening width W1001<the minimum opening width W1002 and the outer circumferential opening width W1005<the outer circumferential opening width W1006 are established. In the minimum opening width W1001 and the minimum opening width W1002, and the outer circumferential opening width W1005 and the outer circumferential opening width W1006, the sizes intermittently vary in the longitudinal direction.

In a modification example of the present embodiment (illustration omitted), a width varying region in which the width size varies may be provided between the narrow width region 1060a and the wide width region 1060b. For example, in the width varying region, the width size increases from the narrow width region 1060a toward the wide width region 1060b.

An opening portion 1060a through which the through hole 1070a is open toward the side has a slit shape which is cut with a narrow width from the outer circumference of the somatometry instrument 1100 toward the through hole 1070a. The sizes of the narrow width region 1060a and the through hole 1070a in the longitudinal direction are substantially equal to each other.

For example, the opening portion 1060 can be formed as follows. First, a slit having a narrow width is formed across the longitudinal direction of a cylinder body. Subsequently, the slit having a narrow width remains in the end-portion regions, and a slit having a relatively wide width size with respect to the slit having a narrow width is continuously formed across the longitudinal direction in the intermediate portion. Accordingly, the opening portion 1060 having the narrow width region 1060a and the wide width region 1060b can be easily formed.

Next, the measurement portion 1040 of the somatometry instrument 1100 will be described.

The measurement portion 1040 in the present embodiment is provided on the outer circumferential surface of the somatometry instrument 1100. That is, the measurement portion 1040 is configured in an arbitrary region on the outer circumferential surface of the somatometry instrument 1100.

As illustrated in FIG. 12A, the somatometry instrument 1100 of the present embodiment is an elongated body which is straightly lengthened from the one end 1110 to the opposite end 1112, and the measurement portion 1040 is provided on the outer circumferential surface of the elongated body.

Here, the outer circumferential surface is a circumferential surface observed when the somatometry instrument 1100 is viewed from the outer side. In regard to the measurement portion 1040 which is the outer circumferential surface, for example, as illustrated in FIG. 13D, in a state where the end-portion abutment portion 1010 is temporarily fixed, in the measurement portion 1040, a spot corresponding to a position of the valve cusp 1210 (here, an arbitrary edge portion of the valve cusp 1210 near the papillary muscle 1212) is recorded with a marker 1220 or the like. Thereafter, the distance from the end-portion abutment portion 1010 to the recorded spot is measured with a size measuring tool such as a ruler, and the distance between the papillary muscle 1212 and the valve cusp 1210 can be thereby measured. When the outer circumferential surface is utilized as the measurement portion 1040, the configuration of the somatometry instrument 1100 can be simplified, thereby being advantageous in manufacturing. Moreover, there is no possibility of damaging the inside of a living body, thereby being preferable.

For example, examples of the marker 1220 include a marker which forms a rod-shaped body provided with an ink absorption portion 1221 at the end portion and in which a sterilized coloring matter (for example, gentian violet) that can be used inside a living body is absorbed into the ink absorption portion 1221. However, the marker 1220 is not limited thereto. In addition, the recording may be performed through means other than recording performed with the marker 1220 or the like. For example, the position of the valve cusp 1210 may be recorded on the outer circumferential surface by scratching the outer circumferential surface.

For example, as illustrated in FIG. 12A, the measurement portion 1040 may be provided with a measuring scale 1012 such that a predetermined distance from the end-portion abutment portion 1010 in the longitudinal direction can be measured. Accordingly, in a state where the end-portion abutment portion 1010 is temporarily fixed, when the position of the valve cusp 1210 is checked on the measuring scale 1012, the distance between the papillary muscle 1212 and the valve cusp 1210 can be measured. As a specific example of the measuring method, in a state where the end-portion abutment portion 1010 is temporarily fixed, the position of the valve cusp 1210 with respect to the measuring scale 1012 is checked with the naked eye, an endoscope, or the like, and the distance between the valve cusp 1210 and the papillary muscle 1212 can be directly measured. In addition, as another example, as described above, the position of the valve cusp 1210 is recorded. Thereafter, the recorded position with respect to the measuring scale 1012 is checked. In this manner, without separately using the size measuring tool, a distance can also be promptly measured after recording.

In the measuring scale 1012, numbers indicating the distances from the end-portion abutment portion 1010 may be suitably applied. In addition, the measuring scale 1012 may be a colored portion in which color changes at a predetermined interval, or may have a configuration in which the distance from the end-portion abutment portion 1010 can be checked by checking the colors. The lines, the numbers, the characters, and arbitrary marks indicating the measuring scale 1012 may be formed by being printed on the outer circumferential surface of the somatometry instrument 1100, may be formed by raising or depressing the outer circumferential surface so as to have a predetermined shape, or may be formed through a combination thereof.

As illustrated in FIG. 14A, as a modification example of the measurement portion 1040, it is possible to exemplify an aspect provided with a protrusion portion 1042 which protrudes from the outer circumferential surface of the somatometry instrument 1100 in the outward direction and extends in the longitudinal direction. The protrusion portion 1042 is a pleated or plate-shaped portion having a comparatively small thickness and having a sufficiently great size in the longitudinal direction. For example, the protrusion portion 1042 continuously extends from the opposite end 1112 exceeding half in the longitudinal direction near the end-portion abutment portion 1010. It is preferable that the protrusion portion 1042 has a size a direction orthogonal to the longitudinal direction to the extent that the protrusion portion 1042 can be pinched with fingers or the like. In FIG. 14A, the region of the protrusion portion 1042 near the opposite end 1112 also serves as the holding portion 1050. However, the protrusion portion 1042 and the holding portion 1050 may be independent from each other so as to be discontinuous in the longitudinal direction.

For example, in a state where the end-portion abutment portion 1010 is temporarily fixed, the spot of the protrusion portion 1042 corresponding to the position of the valve cusp 1210 (illustration omitted) is pinched with tweezers 1402, and the position of the valve cusp 1210 is thereby recorded. Thereafter, the distance between the position pinched with the tweezers 1402 and the end-portion abutment portion 1010 is measured, and the distance between the valve cusp 1210 and the papillary muscle 1212 can be thereby measured. The position pinched with the tweezers 1402 may be checked through pointed-end positions of the tweezers 1402 in a state of pinching the protrusion portion 1042, or may be checked through a scratched position by pinching the protrusion portion 1042 with the tweezers 1402 and scratching a part of the protrusion portion 1042. In addition, the protrusion portion 1042 may be provided with the measuring scale 1012.

In addition, as illustrated in FIG. 14B, as another modification example of the measurement portion 1040, it is possible to exemplify an aspect provided with a movable portion 1044 which can move the measurement portion 1040 in the longitudinal direction.

The movable portion 1044 illustrated in FIG. 14B has a ring shape or a C-shape and has an inner diameter substantially equal to the outer diameter of the cylindrically configured intermediate portion of the somatometry instrument 1100. The inner circumferential surface of the ring-shaped movable portion 1044 is in tight contact with the outer circumferential surface of the somatometry instrument 1100 to the extent that the movable portion 1044 does not move in the longitudinal direction due to its own weight and can move in the longitudinal direction when a force is artificially applied with fingers or the like (illustration omitted). In a state where the end-portion abutment portion 1010 is temporarily fixed, the movable portion 1044 is allowed to move to the position of the valve cusp 1210. Then, the distance between the papillary muscle 1212 and the valve cusp 1210 can be measured by measuring the distance between the end-portion abutment portion 1010 and the movable portion 1044. In the somatometry instrument 1100, the measuring scale 1012 may be provided in a region in which the movable portion 1044 is movable.

In two aspects illustrated in FIGS. 14A and 14B, it is possible to omit the operation in which the position of the valve cusp 1210 is recorded in the measurement portion 1040 with the marker 1220. The position of the valve cusp 1210 can be checked and operated by only the sense of fingers or the like of a technician. Therefore, even in a spot having a narrower space for an operation, the distance between the first site and the second site can be measured. However, the aspects described above do not exclude that the position of the valve cusp 1210 is recorded in the protrusion portion 1042 with the marker 1220.

FIGS. 14A and 14B illustrate the aspects of using an artificial thread 1201 in which a French knot portion 1203 is formed at the end portion. FIGS. 14A and 14B illustrate the aspects in which the somatometry instrument 1100 is installed with respect to the artificial thread 1201 in a state where the papillary muscle 1212 is stitched with the artificial thread 1201 via a pad 1204 and thread cast-off is prevented by the French knot portion 1203. The French knot portion 1203 has a diameter greater than outer diameter of the artificial thread 1201 (illustration omitted) provided at the end portion of the artificial thread 1201. The French knot portion 1203 may be formed by binding the end portions of the artificial thread 1201 itself, or may be formed by providing a different member such as a rod-shaped body at the end portion of the artificial thread 1201.

As described above, the somatometry instrument 1100 can more accurately measure the distance between the papillary muscle 1212 and the valve cusp 1210 than those in the related art.

Therefore, the somatometry instrument 1100 can be used for selecting the size of an artificial tendon-forming auxiliary instrument 1400 (hereinafter, will be also simply referred to as auxiliary instrument 1400, refer to FIGS. 16A and 16B) which is used for joining the valve cusp 1210 and the papillary muscle 1212 together with the artificial tendon 1200.

That is, in a state where the artificial tendon 1200 stitching the papillary muscle 1212 is guided to the artificial thread guidance portion 1070 and the end-portion abutment portion 1010 abuts on the papillary muscle 1212, the measurement portion 1040 included in the somatometry instrument 1100 can measure the distance between the papillary muscle 1212 and the valve cusp 1210. The distance which is measured as described above can be an index for selecting the size of the auxiliary instrument 1400.

When the distance between the valve cusp 1210 and the papillary muscle 1212 is accurately measured with the somatometry instrument 1100, the auxiliary instrument 1400 having an appropriate size can be selected. When the auxiliary instrument 1400 selected as described above is used in the MVP, the papillary muscle 1212 and the valve cusp 1210 can be joined together with the artificial tendon 1200 having a desirable length.

The auxiliary instrument 1400 which is selected by using the somatometry instrument 1100 may adopt any type as long as the auxiliary instrument is used in the MVP and is used for joining the papillary muscle 1212 and the valve cusp 1210 together with the artificial tendon 1200 having an appropriate length. For example, the auxiliary instrument 1400 can be used for selecting the size of the auxiliary device disclosed in PTL 1 described above. As the auxiliary instrument 1400 recommended in the present embodiment, for example, the following aspect can be exemplified.

Figure 16A:
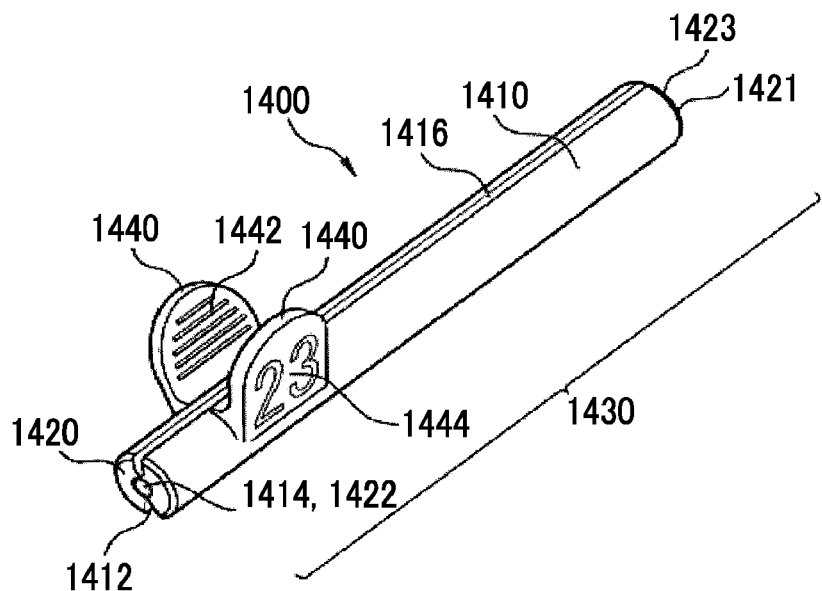
FIG. 16A is a perspective view of an artificial tendon-forming auxiliary instrument which is an example used in the auxiliary instrument set of the aspect of the present invention.
Figure 16B:
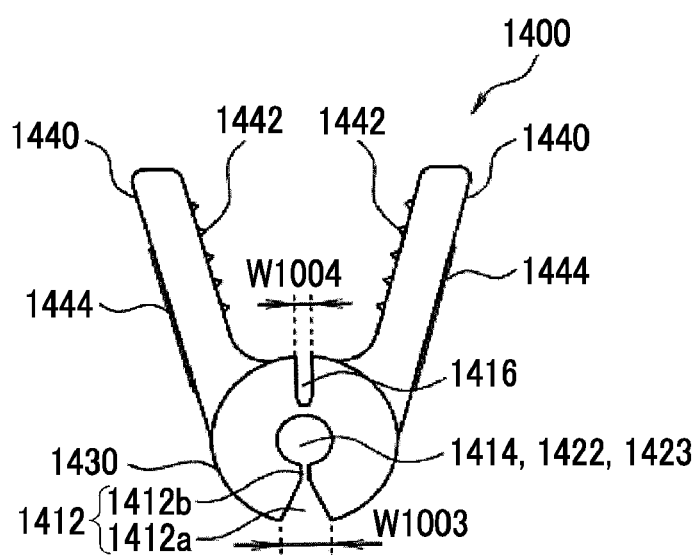
FIG. 16B is a front view of the artificial tendon-forming auxiliary instrument.

That is, as illustrated in FIGS. 16A and 16B, in the auxiliary instrument 1400 recommended in the present embodiment, a pair of end-portion support portions 1420 and 1421 respectively supporting a valve cusp and a papillary muscle is provided at both ends in the longitudinal direction. The auxiliary instrument 1400 includes first and second tendon insertion ports 1422 and 1423 which are respectively formed in the pair of end-portion support portions 1420 and 1421 and have diameters greater than the diameter of the artificial tendon so that the artificial tendon is inserted, a tendon guide portion 1430 which is formed so as to extend in the longitudinal direction across the first and second tendon insertion ports 1422 and 1423, and instrument holding portions 1440 which are formed in the intermediate portion of the tendon guide portion 1430 in the longitudinal direction.

Incidentally, as described above, the auxiliary device disclosed in PTL 1 requires that while the artificial tendon stitching the papillary muscle is pressed by the papillary muscle contact portion, both ends of the artificial tendon are tied together on the hook portion formed in the rod-shaped holding portion. However, such work is not easy to perform, thereby leading to a problem in that a technician is required to be highly skilled.

That is, the rod-shaped holding portion extends to the proximal side of the technician beyond the hook portion. Therefore, when both ends of the artificial tendon are tied together in a state where the valve cusp is mounted on the hook portion, the holding portion unavoidably interferes with the valve cusp. In a case where the MVP is performed by using the auxiliary device in PTL 1, there is a need to tie the artificial tendon in a state where the valve cusp is turned up along the rod-shaped holding portion. Accordingly, it is difficult to perform the procedure of forming a knot on the obliquely tilted valve cusp. In addition, when the auxiliary device is detached after the artificial tendon is fixed, the holding portion interferes with the valve cusp or the knot, thereby disrupting the detaching work.

Figure 17A:
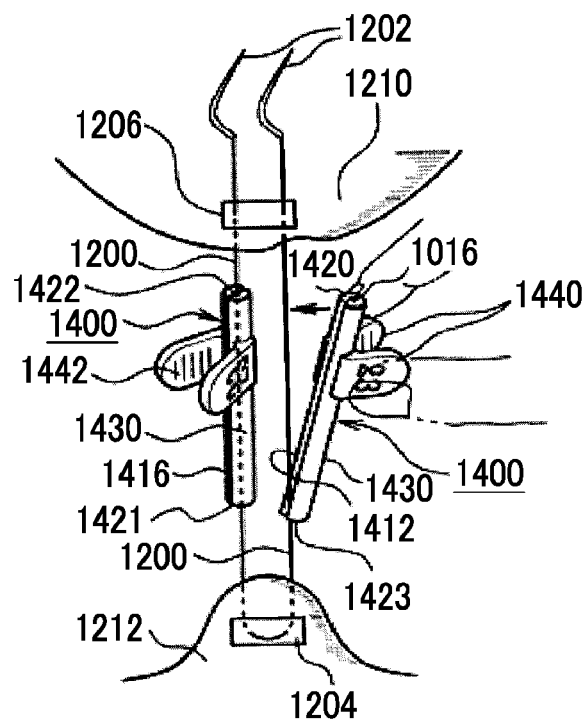
FIG. 17A is a schematic view illustrating a state of a pair of the artificial tendon-forming auxiliary instruments which are respectively installed in the artificial tendons.
Figure 17B:
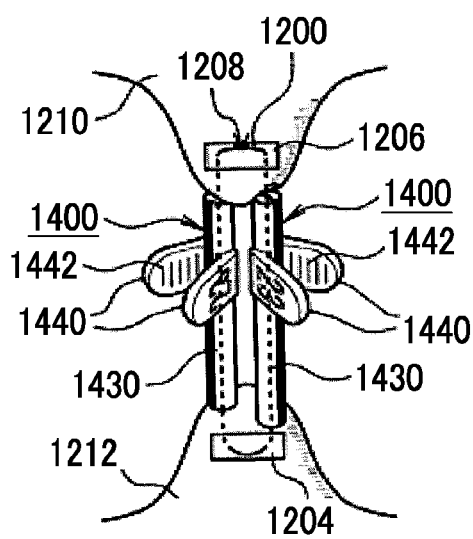
FIG. 17B is a schematic view illustrating a state of a pair of the artificial tendons in which the artificial tendon-forming auxiliary instruments are respectively installed and which are tied together.

In contrast, according to the auxiliary instrument 1400 recommended in the present embodiment, as illustrated in FIG. 17B, a technician holding the instrument holding portions 1440 can install the tendon guide portion 1430 in the artificial tendon 1200 by causing the artificial tendon 1200 stitching at least one side of the papillary muscle 1212 and the valve cusp 1210 to be inserted through the first and second tendon insertion ports 1422 and 1423 (refer to each diagram of FIG. 16). Accordingly, in a state where a gap between the valve cusp 1210 and the papillary muscle 1212 supported by the pair of end-portion support portions 1420 and 1421 maintains a predetermined length, that is, a length of the auxiliary instrument 1400 in the longitudinal direction, the artificial tendon 1200 can be fixed to the valve cusp 1210 or the papillary muscle 1212. Since the instrument holding portions 1440 are formed in the intermediate portion of the auxiliary instrument 1400 in the longitudinal direction, the instrument holding portions 1440 do not interfere with the valve cusp 1210 when the artificial tendon 1200 is fixed, and the valve cusp is not turned up as the auxiliary device in PTL 1.

Therefore, the auxiliary instrument 1400 having an appropriate size is selected by using the somatometry instrument 1100. Moreover, when the MVP is performed by using the selected auxiliary instrument 1400, without depending on the skill of a technician, the valve cusp 1210 and the papillary muscle 1212 can be joined together with the artificial tendon, and the operation of the valve cusp 1210 can thereby be normalized.

The somatometry instrument 1100 of the present embodiment may be provided one each as a single product or as a set having a plurality of instruments. In addition, the somatometry instrument 1100 of the present embodiment may be configured to be a set with the artificial tendon-forming auxiliary instrument used in the MVP.

That is, according to the present invention, there is provided an auxiliary instrument set including the somatometry instrument 1100, and the artificial tendon-forming auxiliary instrument (for example, the auxiliary instrument 1400) used for joining the valve cusp 1210 of the cardiac valve and the papillary muscle 1212 positioned on the downstream side in the normal blood flow direction with respect to the valve cusp 1210 together with the artificial tendon 1200. Accordingly, in the MVP, before the artificial tendon-forming auxiliary instrument is used, the distance between the papillary muscle 1212 and the valve cusp 1210 is measured by using the somatometry instrument 1100, and the distances are grasped. Thus, it is possible to select an appropriate artificial tendon-forming auxiliary instrument based on the distances.

Figure 15:
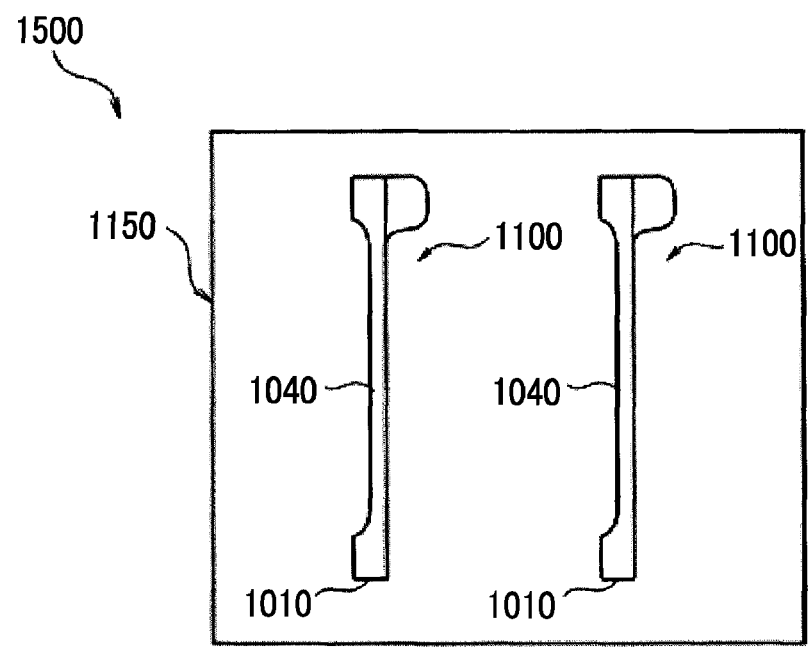
FIG. 15 is a view describing an auxiliary instrument set of an aspect of the present invention.
Figure 15:
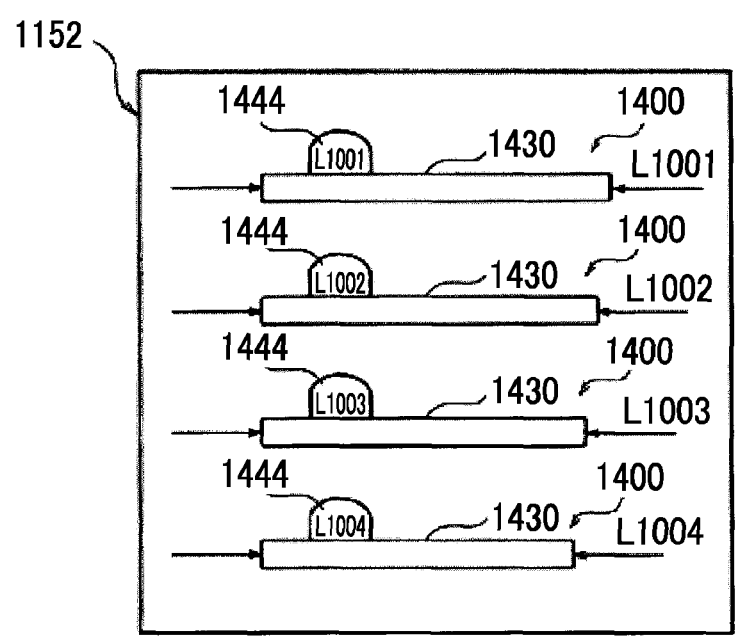

In the description below, as the auxiliary instrument set of the present invention, an aspect of an auxiliary instrument set 1500 including the auxiliary instrument 1400 recommended in the present embodiment as illustrated in FIG. 15 will be described. However, the description does not limit the artificial tendon-forming auxiliary instrument included in the auxiliary instrument set of the present invention. The artificial tendon-forming auxiliary instrument included in the auxiliary instrument set of the present invention can be suitably selected from the auxiliary instruments which are disposed between the valve cusp 1210 and the papillary muscle 1212 and are used for joining the valve cusp 1210 and the papillary muscle 1212 together with the artificial tendon 1200.

The auxiliary instrument set 1500 of the present embodiment will be described by using FIG. 15. FIG. 15 is a view describing the auxiliary instrument set 1500.

As described above, the auxiliary instrument set 1500 includes the somatometry instrument 1100 and the auxiliary instrument 1400. The number of somatometry instruments 1100 and auxiliary instruments 1400 included in the auxiliary instrument set 1500 is not particularly limited. From the intent of selecting the auxiliary instrument 1400 having an appropriate length based on the distances measured with the somatometry instrument 1100, it is preferable that the auxiliary instrument set 1500 includes one or more somatometry instruments 1100 and a plurality of the auxiliary instruments 1400 having lengths different from each other.

For example, as illustrated in FIG. 15, the auxiliary instrument set 1500 has a plurality of the somatometry instruments 1100 and the plurality of artificial tendon-forming auxiliary instruments. The plurality of auxiliary instruments 1400 include the auxiliary instruments 1400 of which the sizes in the longitudinal direction are different from each other, and all of the sizes of the plurality of auxiliary instruments 1400 in the longitudinal direction are below the size of the somatometry instrument 1100 in the longitudinal direction.

In the auxiliary instrument set 1500 having such a combination, the auxiliary instrument 1400 having a length which can correspond to the distance between the valve cusp 1210 and the papillary muscle 1212 measured with the somatometry instrument 1100 can be suitably selected from the plurality of auxiliary instruments 1400 included in the auxiliary instrument set 1500.

FIG. 15 illustrates two somatometry instruments 1100 and four auxiliary instruments 1400 having lengths different from each other. However, the number of somatometry instruments 1100, the number of auxiliary instruments 1400, and the lengths thereof are not limited thereto. The auxiliary instruments 1400 included in the illustrated auxiliary instrument set 1500 includes four types of auxiliary instruments having lengths of L1001 to L1004 one each. However, the variation of the lengths and the number of auxiliary instruments 1400 for each length can be suitably changed.

FIG. 15 is a view describing the plurality of auxiliary instruments 1400 included in the auxiliary instrument set 1500 of the present embodiment. For example, in the auxiliary instrument set 1500, the plurality of somatometry instruments 1100 and the plurality of auxiliary instruments 1400 are collectively and respectively contained in containers as packs 1150 and 1152. One or the plurality of somatometry instruments 1100, and the plurality of auxiliary instruments 1400 may be collectively contained in one container (illustration omitted). It is preferable that the container is a sterilization container such that the sterilization state of contents is maintained. It is because before the auxiliary instrument set 1500 is used, there is no need to perform sterilization treatment for the contents thereof so that the auxiliary instrument set 1500 can be immediately used after being opened.

The pack 1150 includes the plurality of somatometry instruments 1100 having the same lengths and is sealed.

The pack 1152 includes the plurality of auxiliary instruments 1400 having the sizes of the tendon guide portions 1430 in the longitudinal direction are different from each other and is sealed.

As illustrated in FIG. 15, the auxiliary instrument 1400 has a record portion 1444 in which the size (L1001 to L1004) of the auxiliary instrument 1400 in the longitudinal direction is recorded and is able to be viewed from the outside.

When the record portion 1444 is visually recognized, the auxiliary instrument 1400 which can correspond to the distance between the valve cusp 1210 and the papillary muscle 1212 measured with the somatometry instrument 1100 included in the auxiliary instrument set 1500 can be promptly selected from the plurality of auxiliary instruments 1400. In the present embodiment, the record portion 1444 is provided in the instrument holding portion 1440. In the instrument holding portions 1440 in four auxiliary instruments 1400, the sizes such as L1001, L1002, L1003, and L1004 of the tendon guide portions 1430 in the longitudinal direction are recorded.

The difference among the sizes L1001 to L1004 of the tendon guide portions 1430 in the longitudinal direction in the plurality of auxiliary instruments 1400 is N (where is an integer equal to or greater than 1) millimeters. The sizes L1001 to L1004 of the plurality of auxiliary instruments 1400 are different from each other by one millimeter. For example, the sizes L1001 to L1004 can range from 13 millimeters to 16 millimeters. In this manner, when the plurality of auxiliary instruments 1400 in which the sizes L1001 to L1004 of the tendon guide portions 1430 in the longitudinal direction are different from each other are prepared, the appropriate auxiliary instrument 1400 corresponding to the distance measured with the somatometry instrument 1100 can be selected. It is preferable that the sizes L1001 to L1004 are consecutive numerical values differed from each other by one millimeter or the like.

FIG. 15 exemplifies an aspect in which the pack 1152 includes four auxiliary instruments 1400. However, the number of auxiliary instruments 1400 is not particularly limited. In addition, it is favorable that the pack 1152 includes the plurality of auxiliary instruments 1400 in which the sizes L1001 to L1004 of the tendon guide portions 1430 in the longitudinal direction are different from each other, for each of the lengths. That is, the pack 1152 may include the plurality of auxiliary instruments 1400 in which the sizes of the tendon guide portions 1430 in the longitudinal direction are equal to each other, for each of the sizes L1001 to L1004.

For example, it is favorable to include the auxiliary instruments 1400 as many as the number of somatometry instruments 1100 included in the auxiliary instrument set 1500, for each of the sizes. Accordingly, when reconstruction is performed with the plurality of artificial tendons 1200, the distance between the valve cusp 1210 and the papillary muscle 1212 is measured with the somatometry instrument 1100 for each of the spots scheduled for reconstruction of the artificial tendon 1200, and the auxiliary instrument 1400 corresponding thereto can be selected from the auxiliary instrument set 1500 with no shortage.

The somatometry instrument 1100 or the auxiliary instrument 1400 in its entirety may be colorless, or may be colored with a color in its entirety or partially. In the somatometry instrument 1100 of the present embodiment, pigments are kneaded with soft resin materials respectively configuring the somatometry instrument 1100 and the auxiliary instrument 1400. Accordingly, visibility thereof is favorable. In the auxiliary instrument set 1500, the somatometry instrument 1100 and the auxiliary instrument 1400 may be colored with colors different from each other. Accordingly, during the procedure, the somatometry instrument 1100 and the auxiliary instrument 1400 can be smoothly distinguished from each other.

In addition, a radio-opaque contrast agent such as barium sulfate may be kneaded with the soft resin material configuring the somatometry instrument 1100 or the auxiliary instrument 1400. Accordingly, after the procedure ends, it is possible to check that the somatometry instrument 1100 or the auxiliary instrument 1400 is not left behind inside a body lumen of the test subject, through X-ray radiography.

Hereinafter, the auxiliary instrument 1400 will be described in detail by using FIGS. 16A, 16B, 17A, 17B, and 17C.

Figure 17C:
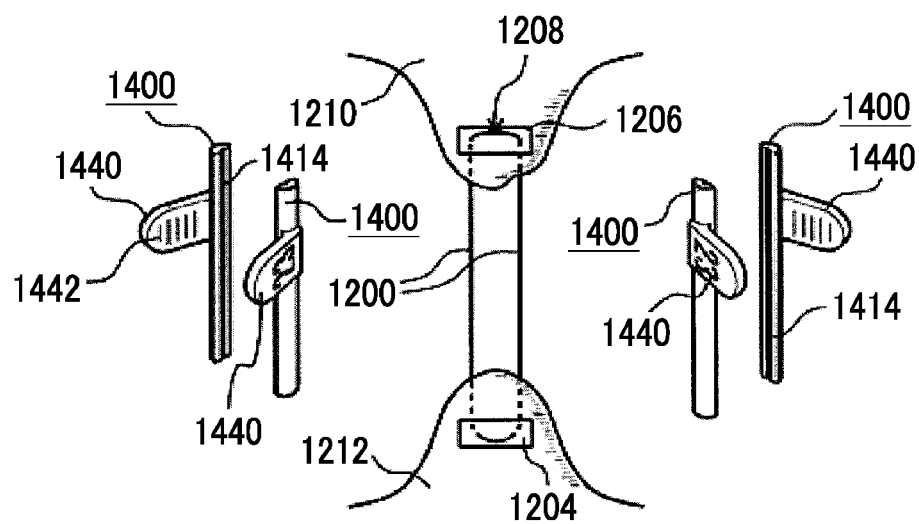
FIG. 17C is a schematic view illustrating a state of the artificial tendon-forming auxiliary instruments which are detached from the artificial tendons.

FIG. 16A is a perspective view of the auxiliary instrument 1400 which is an example used in the auxiliary instrument set 1500 of the present embodiment. FIG. 16B is a front view of the auxiliary instrument 1400. FIG. 17A is a schematic view illustrating a state of a pair of the auxiliary instruments 1400 which are respectively installed in the artificial tendon 1200. FIG. 17B is a schematic view illustrating a state of a pair of the artificial tendons 1200 in which the auxiliary instruments 1400 are respectively installed and which are tied together. FIG. 17C is a schematic view illustrating a state of the auxiliary instruments 1400 which are detached from the artificial tendons 1200.

The auxiliary instrument 1400 of the present embodiment is broadly configured with the tendon guide portion 1430 configuring the main body portion, the first tendon insertion port 1422 and the second tendon insertion port 1423 which are respectively formed at both ends of the tendon guide portion 1430 in the longitudinal direction, and the pair of instrument holding portions 440 for holding the tendon guide portion 1430 with fingers or the like of a technician.

As illustrated in FIG. 17B, the tendon guide portion 1430 is a portion which is interposed between the valve cusp 1210 and the papillary muscle 1212 and guides the artificial tendon 1200 to a space between the valve cusp 1210 and the papillary muscle 1212 in a state of being lengthened practically straight. The tendon guide portion 1430 of the present embodiment is in a hollow tubular shape and includes a central lumen 1414. However, the present invention is not limited thereto.

As illustrated in FIG. 16B, the tendon guide portion 1430 has the hollow tubular shape including a slit portion 1412 which is open with the opening width W1003 (refer to FIG. 16B) capable of receiving the artificial tendon 1200 (refer to FIG. 17A), and the central lumen 1414 which penetrates the tendon guide portion 1430 in the longitudinal direction. The slit portion 1412 is formed on a side of the tendon guide portion 1430 across the overall length in the longitudinal direction and communicates with the central lumen 1414 through the side.

A circumferential surface 1410 of the tendon guide portion 1430 is a substantially cylindrical surface, and the slit portion 1412 is formed along the central axis (axis in the longitudinal direction) thereof so as to be cut in the radial direction of the tendon guide portion 1430 at a depth from the circumferential surface 1410 to the central lumen 1414. As illustrated in FIG. 16B, the slit portion 1412 is configured with a narrow-width portion 1412b and a wide-width portion 1412a. The narrow-width portion 1412b is a portion having a diameter smaller than the diameter of the central lumen 1414 and is connected to the central lumen 1414. The wide-width portion 1412a is a portion which is smoothly and continuously provided radially outward beyond the narrow-width portion 1412b and of which the width size is gradually widened toward the circumferential surface 1410. The maximum width size of the wide-width portion 1412a is the opening width W1003, and the minimum width size of the wide-width portion 1412a is substantially equal to the width size of the narrow-width portion 1412b. The opening width W1003 of the slit portion 1412 is sufficiently greater than the diameter (wire diameter) of the artificial tendon 1200. However, the slit portion 1412 is not limited to that described above, and various forms can be employed.

The central lumen 1414 is a penetration hole which is formed substantially at the center of the tendon guide portion 1430. The central lumen 1414 of the present embodiment is formed so as to have a substantially circular shape in a front view as illustrated in FIG. 16B.

The instrument holding portions 1440 are portions for holding the auxiliary instrument 1400 with fingers or the like of a technician. The instrument holding portions 1440 of the present embodiment form a pair and have one-plate shapes protruding radially outward from the circumferential surface 1410 of the tendon guide portion 1430. Accordingly, as illustrated in FIG. 17A, for example, a technician can hold the auxiliary instrument 1400 such that the pair of instrument holding portions 1440 is interposed with a thumb and an index finger. Forming regions of the instrument holding portions 1440 are on an inner side of both ends of the tendon guide portion 1430 in the longitudinal direction. Accordingly, as illustrated in FIG. 17B, when the auxiliary instrument 1400 is interposed between the valve cusp 1210 and the papillary muscle 1212, the instrument holding portions 1440 do not interfere with any of the valve cusp 1210 and the papillary muscle 1212. Accordingly, when work of tying both ends of the artificial tendon 1200 together is performed, the instrument holding portions 1440 are not disrupted.

The instrument holding portions 1440 are formed at positions biased to the end-portion support portion on one side (in the present embodiment, the end-portion support portion 1420) in the intermediate portion of the tendon guide portion 1430. Accordingly, as illustrated in FIG. 17A, it is possible to acquire excellent workability when the artificial tendon 1200 is inserted through the tendon guide portion 1430 through the slit portion 1412, in other words, when the tendon guide portion 1430 is installed with respect to the artificial tendon 1200.

The end-portion support portions 1420 and 1421 are portions which are respectively supporting the valve cusp 1210 and the papillary muscle 1212 and are provided at both ends of the tendon guide portion 1430 of the auxiliary instrument 1400 in the longitudinal direction. The end-portion support portions 1420 and 1421 are formed so as to have plane shapes. The end-portion support portions 1420 and 1421 may have flat plane shapes or curved plane shapes. If the end-portion support portion 1420 and the end-portion support portion 1421 are formed so as to have the plane shapes, as illustrated in FIG. 17B, when the artificial tendon 1200 is tied with a predetermined tensile force, the end-portion support portion 1420 and the end-portion support portion 1421 do not excessively intrude on the valve cusp 1210 or the papillary muscle 1212. Accordingly, the tendon guide portion 1430 of the auxiliary instrument 1400 serves as a spacer, and the longitudinal size thereof becomes the separation distance between the valve cusp 1210 and the papillary muscle 1212. When the artificial tendon 1200 is fixed to the valve cusp 1210 in such a state, after the mitral valve plasty, the valve cusp 1210 and the papillary muscle 1212 are thereby joined together with the artificial tendon 1200 having a desired length.

The tendon guide portion 1430 can be produced by using a material similar to that of the somatometry instrument 1100 described above. Accordingly, when the tendon guide portion 1430 is tied while having the artificial tendon 1200 as the spacer, even if the valve cusp 1210 or the papillary muscle 1212 is pressed with respect to the tendon guide portion 1430 with a predetermined force, the valve cusp 1210 or the papillary muscle 1212 is not damaged by the tendon guide portion 1430.

The instrument holding portions 1440 may be integrally molded with the tendon guide portion 1430 by using one material. Otherwise, after the instrument holding portions 1440 are produced as different members, the instrument holding portions 1440 may be may be integrated with the tendon guide portion 1430 by being bonded to the circumferential surface 1410. The present embodiment exemplifies a case where the instrument holding portions 1440 are integrally molded with the tendon guide portion 1430 by using one material.

The first tendon insertion port 1422 is formed in the end-portion support portion 1420, and the second tendon insertion port 1423 is formed in the end-portion support portion 1421. The first tendon insertion port 1422 of the present embodiment is an open end of the central lumen 1414 on one side, and the second tendon insertion port 1423 is an open end of the central lumen 1414 on the other side.

As illustrated in FIGS. 16A and 16B, in the first tendon insertion port 1422 and the second tendon insertion port 1423, the slit portion 1412 is continuously provided in the radial direction of the tendon guide portion 1430. The slit portion 1412 is formed across the overall length of the tendon guide portion 1430 in the longitudinal direction.

Therefore, as illustrated in FIG. 17A, in a state where the slit portion 1412 encounters the artificial tendon 1200, the tendon guide portion 1430 can be installed from the side.

As illustrated in FIGS. 16A and 16B, a rough surface portion 1442 is provided in at least a part on the surface of the instrument holding portion 1440. The rough surface portion 1442 of the present embodiment is configured with a plurality of recessed grooves parallel to each other. The rough surface portion 1442 can be formed by transcribing projections which are formed on the inner surface of a mold (not illustrated) used in injection molding of the instrument holding portions 1440. Moreover, the rough surface portion 1442 may be the plurality of recessed grooves intersecting each other, the rough surface portion 1442 may be an uneven portion in which many points are randomly formed or arranged in an array or may be the projections. In addition, the rough surface portion 1442 may be formed by performing roughening treatment of the surface of the instrument holding portions 1440 after injection molding.

The surface of the instrument holding portion 1440 on one side in the present exemplary aspect serves as the rough surface portion 1442, and the surface on the other side serves as the record portion 1444. For example, in two instrument holding portions 1440 facing each other, it is favorable that the rough surface portion 1442 is provided on a surface on the facing side, and the record portion 1444 is provided on a surface on a side opposite to the facing side.

The instrument holding portion 1440 of the auxiliary instrument 1400 illustrated in FIGS. 16A and 16B is provided with the record portion 1444 in which "23" is recorded. This denotes that the size of the tendon guide portion 1430 in the longitudinal direction is "23 mm". When the distance measured through the somatometry instrument 1100 is 23 mm or a value close thereto, it is possible to smoothly select the auxiliary instrument 1400 illustrated in FIGS. 16A and 16B.

On the circumferential surface 1410 of the tendon guide portion 1430, an easily-tearable portion 1416 for tearing the tendon guide portion 1430 is formed along the longitudinal direction.

When the easily-tearable portion 1416 is formed in the tendon guide portion 1430, after the valve cusp 1210 and the papillary muscle 1212 are joined together with the artificial tendon 1200, the tendon guide portion 1430 is broken along the longitudinal direction so as to be divided into a plurality of pieces. Accordingly, the auxiliary instrument 1400 can be easily detached from the artificial tendon 1200. As illustrated in each diagram of FIG. 17, it is favorable to install the auxiliary instrument 1400 in the artificial tendon 1200 such that the instrument holding portions 1440 approach the valve cusp 1210 rather than the papillary muscle 1212. Accordingly, when the pair of instrument holding portions 1440 is held with fingers or the like so as to break the tendon guide portion 1430, it is possible to easily have access to the instrument holding portions 1440 from the left atrium 302 (refer to FIG. 1B) of a test subject subjected to thoracotomy.

The easily-tearable portion 1416 of the present embodiment is formed on a side facing the slit portion 1412 in the circumferential surface 1410 of the tendon guide portion 1430 along the slit portion 1412. The easily-tearable portion 1416 is continuously or intermittently formed along the slit portion 1412 across the overall length in the longitudinal direction.

In addition, the pair of instrument holding portions 1440 is formed on both sides so as to interpose the easily-tearable portion 1416 therebetween. Accordingly, when the pair of instrument holding portions 1440 is pulled outward in directions opposite to each other with a force equal to or greater than predetermined strength, the tendon guide portion 1430 is torn across the overall length. As illustrated in FIG. 17C, the auxiliary instrument 1400 is completely separated into two portions. The easily-tearable portion 1416 does not intersect the slit portion 1412 and is formed across the overall length of the tendon guide portion 1430 in the longitudinal direction. Therefore, unexpected small pieces are not generated when the tendon guide portion 1430 is torn.

The easily-tearable portion 1416 is a bottomed recessed groove which is cut from the circumferential surface 1410 of the tendon guide portion 1430 toward the central lumen 1414 in a non-penetration manner. The opening width W1004 of the easily-tearable portion 1416 is smaller than the opening width W1003 of the slit portion 1412. By restraining the opening width W1004 of the easily-tearable portion 1416 to be smaller than the opening width W1003 of the slit portion 1412, a technician is prevented from being confused between the easily-tearable portion 1416 and the slit portion 1412.

In place of the present embodiment, without forming the easily-tearable portion 1416 and dividing the auxiliary instrument 1400 into a plurality of pieces, the auxiliary instrument 1400 can be detached from the artificial tendon 1200. That is, when the pair of instrument holding portions 1440 is strongly pulled outward in directions opposite to each other from the state illustrated in FIG. 17B, the tendon guide portion 1430 can be subjected to plastic deformation such that the slit portion 1412 is open wide. Accordingly, the artificial tendon 1200 accommodated in the central lumen 1414 can easily pass through the narrow-width portion 1412b, and the auxiliary instrument 1400 can be thereby detached from the artificial tendon 1200.

Hereinafter, a usage example of the somatometry instrument 1100 and the auxiliary instrument 1400 will be described by using FIGS. 13A to 13D, 15, and 17A to 17C. In this usage example, in order to select the auxiliary instrument 1400 having an appropriate length used in the MVP, first, by using FIGS. 13A to 13D, a method of measuring the distance between the papillary muscle 1212 and the valve cusp 1210 in a spot scheduled for reconstruction of the artificial tendon 1200, with the somatometry instrument 1100 (hereinafter, will be also referred to as this measuring method) will be described. Then, the method of selecting the auxiliary instrument 1400 having an appropriate length based on the distances measured through this measuring method and reconstructing the artificial tendon 1200 (hereinafter, will be also referred to as this reconstruction method) will be described by using FIGS. 17A to 17C. FIG. 15 illustrates the auxiliary instrument set 1500 used in this usage example. However, in this usage example, the somatometry instruments 1100 and the auxiliary instruments 1400 which are individually handled (that is, not being in a set) can also be suitably used.

The cardiac valve in which the valve cusp 210 and the papillary muscle 212 are joined together with the artificial tendon 200 by using the auxiliary instrument 1400 includes the mitral valve 310; and the tricuspid valve 312, the aortic valve 314, and the pulmonary arterial valve 316 as well (refer to FIG. 1B). Among these, in this usage example, description will be given regarding the mitral valve plasty in which the tendons 1214 in one or both of two valve cusps 1210 of a mitral valve 1310 are reconstructed with the artificial tendon 1200. In a normal mitral valve 1310, the valve cusps 1210 are respectively joined to the papillary muscles 1212 via a plurality of tendons 1214. In FIGS. 13A to 13D and 17A to 17C used in this usage example, illustration of the normal tendon 1214 is suitably omitted. In FIG. 13A, broken tendons 1214 are illustrated, and in FIGS. 13B to 13D, illustration of the broken tendons 1214 is omitted.

As illustrated in FIG. 13A, in a case where a part of the tendon 214 joining the papillary muscle 1212 and the valve cusp 1210 together is broken or the like, this usage example is applied.

First, as illustrated in FIG. 13B, in accordance with the spot scheduled for reconstruction of the artificial tendon 1200, the papillary muscle 1212 is stitched with the artificial tendon 1200 as the artificial thread. In regard to the artificial tendon 1200, with respect to the papillary muscle 1212, two spots close to each other are stitched with the artificial tendon 1200, and the artificial tendon 1200 is caused to make a U-turn. Since the papillary muscle 1212 is positioned in the left ventricle deeper than the valve cusp 1210, it is favorable to stitch the papillary muscle 1212 with the artificial tendon 1200 in advance. However, the valve cusp 1210 is stitched with the artificial tendon 1200, and the distance between the papillary muscle 1212 and the valve cusp 1210 is measured, or the artificial tendon 1200 can be reconstructed by using the auxiliary instrument 1400. Although illustration is omitted in FIGS. 13B to 13D, in a stitch portion 1205 (turn-around portion of the artificial tendon 1200 in the papillary muscle 1212) of the artificial tendon 1200 provided in the papillary muscle 1212, the pad 1204 may be suitably applied as illustrated in each diagram of FIG. 17 so as to achieve protection of the papillary muscle 1212.

In the artificial tendon 1200 used in this usage example, the puncture needles 1202 are provided at both end portions. The puncture needles 1202 are curved needles. Even in a case of having access to the papillary muscle 212 from the left ventricle through the mitral valve 310 (refer to FIG. 1B), puncturing can be easily performed with the puncture needles 1202 from the papillary muscle 212 toward the valve cusp 210, and a low invasive procedure can be thereby performed. For example, the artificial tendon 1200 can be produced by using a synthetic resin material. Specifically, for example, Gore-tex (registered trademark) obtained by performing stretching processing of polytetrafluoroethylene and compounding the result with a polyurethane resin can be used as the artificial tendon 1200. Felt or fluororesin films can be used as the pad 1204 and a pad 1206. The same type materials or the different type materials can be used for the pad 1204 and the pad 1206.

As illustrated in FIG. 13C, the somatometry instrument 1100 is installed with respect to the artificial tendon 1200. With respect to two straight portions of the artificial tendon 1200 which is turned around the papillary muscle 1212 and has a V-shape, two somatometry instruments 1100 are individually installed. In the somatometry instrument 1100, the opening portion 1060 is formed along the longitudinal direction from the first insertion port 1020 to the second insertion port 1030. Therefore, the somatometry instrument 1100 can be installed with respect to the artificial tendon 1200 from the side. Accordingly the artificial tendon 1200 is in a state of being guided to the artificial thread guidance portion 1070 which communicates with the opening portion 1060. In this manner, when the opening portion 1060 is included, threading work in which the artificial tendon 1200 is inserted through can be allocated with respect to the first insertion port 1020 and the second insertion port 1030. The somatometry instrument 1100 can be easily installed with respect to the artificial tendon 1200 in which the puncture needles 1202, that is, the curved needles are provided at the end portions.

The installing orientation of the somatometry instrument 1100 is adjusted such that the end-portion abutment portion 1010 abuts on the papillary muscle 1212. The end-portion abutment portion 1010 is provided with the first insertion port 20, and in a state where the artificial tendon 1200 is inserted through the first insertion port 1020, the end-portion abutment portion 1010 abuts on the papillary muscle 1212. Accordingly, the end-portion abutment portion 1010 can be temporarily fixed to the papillary muscle 1212 which is the first site. Accordingly, the base end of the artificial tendon 1200 on one side to be reconstructed can match the measurement end of which the distance is measured with the somatometry instrument 1100. Therefore, according to the somatometry instrument 1100, a measurement of the distance between the spots scheduled for reconstruction of the artificial tendon 1200 can be accurately executed compared to the measuring methods in the related art using echoes and the like.

The somatometry instrument 1100 installed in the artificial tendon 1200 is oriented so as to be substantially parallel to a direction in which the artificial tendon 1200 is reconstructed (hereinafter, will be also referred to as reconstruction direction) from the papillary muscle 1212 with respect to the valve cusp 1210 by operating the artificial tendon 1200 or operating the somatometry instrument 1100 itself, as in FIG. 13C. The size of the somatometry instrument 1100 in the longitudinal direction used in this usage example is designed so as to be sufficiently longer than a normal distance (that is, the length of a normal tendon 1214) between the papillary muscle 1212 and the valve cusp 1210 of a general adult. Therefore, in a case where the somatometry instrument 1100 is oriented in the reconstruction direction, the opposite end 1112 arrives at the intermediate portion of the valve cusp 1210 which is the second site, or in front (technician side) of the valve cusp 1210. In this state, when the somatometry instrument 1100 is viewed from the side, the attachment position of the artificial tendon 1200 in the valve cusp 1210 can be checked in the intermediate portion of the somatometry instrument 1100. In this usage example illustrated in FIG. 13C, the opposite end 1112 of the artificial tendon 1200 is positioned on the front side in the sheet of the valve cusp 1210 and in the middle of the valve cusp 1210 in the thickness direction. Therefore, the outer edge (position at which the artificial tendon is attached) of the valve cusp 1210 facing the papillary muscle 1212 is checked in the measurement portion 1040 of the somatometry instrument 1100. Even in a case of measuring the distance inside a living body other than the distance between the papillary muscle 1212 and the valve cusp 1210, it is preferable that the somatometry instrument 1100 has a size in the longitudinal direction sufficiently greater than a schematic distance between the first site and the second site scheduled for a measurement.

As described above, when the outer edge (position at which the artificial tendon is attached) of the valve cusp 1210 is checked with respect to the measurement portion 1040, as illustrated in FIG. 13D, the position is recorded in the measurement portion 1040 with the marker 1220. The position of the outer edge of the valve cusp 1210 can be checked with the naked eye or an endoscope, or can be checked by the sense of a fingertip, an abutment condition, or the like of the marker 1220.

In a case where the plurality of tendons 1214 is broken or the like and is no longer in a normal state, as illustrated as a papillary muscle 1212a, there are cases where the papillary muscle 1212 is loosened compared to a normal shape. In this manner, in a case where the papillary muscle 1212a in a loosened state is observed through echoes or viewing, there are cases where it is difficult to appropriately grasp the distance between the papillary muscle 1212 and the valve cusp 1210. In contrast, as in FIG. 13B, when the papillary muscle 1212 is stitched with the artificial tendon 1200 and the artificial tendon 1200 is appropriately strained, a papillary muscle 1212b in a normal state (or in a state close thereto) can be reproduced. Therefore, when the somatometry instrument 1100 is used, as illustrated in FIG. 13B, it is possible to measure the distance between the papillary muscle 1212b and the valve cusp 1210 in which the artificial tendon 1200 is appropriately strained and a normal distance is reproduced. Accordingly, the distance between the papillary muscle 1212 and the valve cusp 1210 can be accurately measured. In addition, based on the distances which are accurately measured, the auxiliary instrument 1400 having an appropriate length can be selected.

As described above, the somatometry instrument 1100 in which recording is performed in the measurement portion 1040 is uncoupled from the artificial tendon 1200 (illustration omitted). The uncoupling method is not particularly limited. However, for example, it is favorable that the position of the somatometry instrument 1100 is moved to a side opposite to the stitch portion 1205 of the artificial tendon 1200 and the artificial tendon 1200 is separated from the somatometry instrument 1100 via the opening portion 1060 in front of the puncture needle 1202.

Based on the distance between the papillary muscle 1212 and the valve cusp 1210 measured as described above, it is possible to select the auxiliary instrument 1400 having an appropriate size used in this reconstruction method described below. For example, as illustrated in FIG. 13D, when the distance between the papillary muscle 1212 and the valve cusp 1210 is measured at two different places, there are cases where the distance measured with a somatometry instrument 1100b on the right side in the sheet is greater than the distance measured with a somatometry instrument 1100a on the left side in the sheet. In such a case, as illustrated in FIG. 15, it is possible to select the artificial tendon-forming auxiliary instrument 1400 having a length same as or closest to the individually measured distance, from the plurality of artificial tendon-forming auxiliary instruments 1400 having lengths different from each other.

This reconstruction method in which the artificial tendon 1200 is reconstructed by using the auxiliary instrument 1400 selected as described above will be described below.

The artificial tendon 1200 is used in both this measuring method described above and this reconstruction method described below. Since there is no need to separately perform stitching with the artificial thread for a measurement, a series of steps of work of this measuring method and this reconstruction method can be smoothly performed within a short period of time. In order to use the artificial tendon 1200 in both methods as described above, for example, it is favorable to employ the following aspect.

That is, as described above, the artificial tendon-forming auxiliary instrument 1400 includes the pair of end-portion support portions 1420 and 1421 which respectively support the valve cusp 1210 and the papillary muscle 1212 and are provided at both ends of the auxiliary instrument 1400 in the longitudinal direction, and the first and second tendon insertion ports 1422 and 1423 which are respectively formed in the pair of end-portion support portions 1420 and 1421 and have diameters greater than the diameter of the artificial tendon 1200 and through which the artificial tendon 1200 is inserted. Here, it is preferable that the calibers of the first and second tendon insertion ports 1422 and 1423 of the artificial tendon-forming auxiliary instrument 1400 and the caliber of the first insertion port 1020 of the somatometry instrument 1100 are substantially the same as each other. Accordingly, the artificial tendon 1200 used in the artificial tendon-forming auxiliary instrument 1400 can also be used as the artificial thread used in the somatometry instrument 1100. In addition, the installing sense when being installed with respect to the artificial tendon 1200 can be favorably stabilized to the same extent in any of the somatometry instrument 1100 and the auxiliary instrument 1400. In the present embodiment, it is more preferable that the caliber of the second insertion port 1030 which is the draw-out portion is substantially the same as the calibers of the first and second tendon insertion ports 1422 and 1423.

In regard to the present invention, a state where a plurality of calibers are substantially the same as each other denotes that any one caliber ranges from one to two times the other caliber. For example, the size may range from one to 1.5 times.

In addition, it is preferable that the minimum opening width W1001 (refer to FIG. 12C) of the somatometry instrument 1100 and the width size of the narrow-width portion 1412b (refer to FIG. 16B) of the auxiliary instrument 1400 are substantially the same as each other. Since approximately the same magnitude of a force can be applied when the artificial tendon 1200 passes through the minimum opening width W1001 or the narrow-width portion 1412b from the somatometry instrument 1100 or the auxiliary instrument 1400 and is uncoupled, the sense of use is favorable.

In addition, preferably, it is preferable that the opening width (outer circumferential opening width W1005) the outer circumferential surface in the narrow width region 1060a (refer to FIG. 12C) of the somatometry instrument 1100 and the opening width W1003 (refer to FIG. 16B) of the auxiliary instrument 1400 are substantially the same as each other. Since approximately the same magnitude of a force can be applied when the somatometry instrument 1100 or the auxiliary instrument 1400 is installed with respect to the artificial tendon 1200, the sense of use is favorable.

In regard to the present invention, a state where a plurality of width sizes are substantially the same as each other denotes that any one caliber ranges from one to 1.2 times the other caliber.

In regard to execution of this reconstruction example, first, as illustrated in FIG. 17A, the auxiliary instrument 1400 is installed with respect to the papillary muscle 1212 stitched with the artificial tendon 1200. In this usage example, with respect to two straight portions of the artificial tendon 1200 which is turned around the papillary muscle 1212 and has a V-shape, two auxiliary instruments 1400 are individually installed. In the auxiliary instrument 1400, the slit portion 1412 is formed along the tendon guide portion 1430 across the overall length in the longitudinal direction, and the tendon guide portion 1430 can be installed with respect to the artificial tendon 1200 from the side. Therefore, there is no need to insert the curved puncture needle 1202 through the central lumen 1414 of the tendon guide portion 1430. In other words, since there is no need to insert the puncture needle 1202 through the central lumen 1414 of the tendon guide portion 1430, a curved needle can be used as the puncture needle 1202.

More specifically, in a state where the papillary muscle 1212 and the valve cusp 1210 are punctured with the puncture needle 1202, and the artificial tendon 1200 is laid with practically no tensile force between the papillary muscle 1212 and the valve cusp 1210, the tendon guide portion 1430 of the auxiliary instrument 1400 is installed with respect to the artificial tendon 1200. For example, as illustrated in FIG. 17A, the instrument holding portions 1440 are held with fingers or the like, and the artificial tendon 1200 is introduced to the tendon guide portion 1430 from the side through the slit portion 1412. Accordingly, the artificial tendon 1200 is in a state of being guided to the central lumen 1414.

Subsequently, when the valve cusp 1210 is stitched with the artificial tendon 1200 in which the auxiliary instrument 1400 is installed, the valve cusp 1210 and the papillary muscle 1212 are joined together with the artificial tendon 1200 matching the length of the central lumen 1414 (longitudinal size of the tendon guide portion 1430).

In this state, both ends of the artificial tendon 1200 are tied together and a knot 1208 is formed on the pad 1206 (refer to FIG. 17B). Accordingly, the artificial tendon 1200 is in a loop state. The process of tying the artificial tendon 1200 is performed in a state where the valve cusp 1210 and the papillary muscle 1212 are pressed to both ends of the tendon guide portion 1430 of the auxiliary instrument 1400. Accordingly, as illustrated in FIG. 17B, in a state where the tendon guide portion 1430 of the auxiliary instrument 1400 is interposed between the valve cusp 1210 and the papillary muscle 1212, the length of the artificial tendon 1200 is determined. Since the artificial tendon 1200 formed so as to be in a loop state is turned around on the pad 1204 and the pad 1206, the artificial tendon 1200 is restrained from intruding on the papillary muscle 1212 or the tendon 1214.

Next, as illustrated in FIG. 17C, the instrument holding portions 1440 of the auxiliary instrument 1400 are pulled outward in directions opposite to each other such that the tendon guide portion 1430 is torn. Since the process is performed in a state where the auxiliary instrument 1400 is interposed between the valve cusp 1210 and the papillary muscle 1212, from the viewpoint of accessibility to the instrument holding portions 1440, it is favorable hold the instrument holding portions 1440 by using an instrument such as tweezers. When the instrument holding portions 1440 of the auxiliary instrument 1400 are pulled, the auxiliary instrument 1400 is torn into two portions, and the auxiliary instrument 1400 is detached from the valve cusp 1210 and the papillary muscle 1212 so as to be separated from the side of the artificial tendon 1200.

As described above, in this usage example, the distance between the papillary muscle 1212 and the valve cusp 1210 is accurately measured in advance with the somatometry instrument 1100, and the artificial tendon 1200 is reconstructed by using the auxiliary instrument 1400 selected based thereon. Accordingly, the papillary muscle 212 and the valve cusp 210 are stitched with the artificial tendon 1200 having a desired length substantially matching the normal tendon 214 (refer to FIG. 1B).

In this measuring method described above, an example in which the somatometry instrument 1100 is installed in the artificial tendon 1200 stitching the papillary muscle 1212 is illustrated. However, the aspect of using the somatometry instrument 1100 is not limited thereto. The somatometry instrument 1100 may be installed in the artificial tendon 1200 first, and thereafter, the papillary muscle 1212 may be stitched with the artificial tendon 1200. For example, in the aspect in which no opening portion 1060 is provided in the somatometry instrument 1100, as described above, it is favorable that the somatometry instrument 1100 is installed with respect to the artificial tendon 1200 in advance, and the papillary muscle 1212 is stitched with the artificial tendon 1200.

In addition, in this measuring method described above, as the artificial thread, the artificial tendon 1200 used in this reconstruction method is also used. However, this measuring method is not limited thereto. An artificial thread other than the artificial tendon 1200 may be used. After this measuring method ends, the artificial thread may be removed from the inside of a living body, and a spot substantially equal to the spot stitched with the artificial thread may be stitched with the artificial tendon 1200 again, thereby executing this reconstruction method.

In addition, in this measuring method and this reconstruction method, the aspect in which the papillary muscle 1212 is stitched with the artificial tendon 1200 so as to have a V-shape, and two somatometry instruments 1100 or two auxiliary instruments 1400 are installed in two straight lines configuring the V-shape is described. As a modification example, the artificial tendon 1200 in which the French knot portion 1203 illustrated in FIGS. 14A and 14B is produced in one end portion may be used, the nipple may be stitched in one direction with the artificial tendon 1200 so as to have an I-shape, and one somatometry instrument 1100 or one auxiliary instrument 1400 may be installed. In this case, one artificial tendon is reconstructed.

Hereinbefore, the embodiments of the present invention are described. The present invention is not limited to the embodiments described above and includes aspects such as various types of modifications and improvements as long as the objects of the present invention are achieved.

The embodiments include the following technical ideas.

(1) An artificial tendon-forming auxiliary instrument is used for joining a valve cusp of a cardiac valve and a papillary muscle with an artificial tendon. The instrument includes a pair of end-portion support portions which respectively support the valve cusp and the papillary muscle and are provided at both ends of the instrument in a longitudinal direction, first and second tendon insertion ports which are respectively formed in the pair of end-portion support portions and have diameters greater than a diameter of the artificial tendon and through which the artificial tendon is inserted, a tendon guide portion which is formed so as to extend in the longitudinal direction across the first and second tendon insertion ports, and an instrument holding portion which is formed in an intermediate portion of the tendon guide portion in the longitudinal direction.

(2) The artificial tendon-forming auxiliary instrument according to (1), in which the instrument holding portion is formed at a position biased to the end-portion support portion on one side in the intermediate portion of the tendon guide portion.

(3) The artificial tendon-forming auxiliary instrument according to (1) or (2), in which the tendon guide portion is in a hollow tubular shape and includes a slit portion which is open with an opening width capable of receiving the artificial tendon, and a central lumen which penetrates the tendon guide portion in the longitudinal direction. The slit portion is formed on a side of the tendon guide portion across an overall length in the longitudinal direction and communicates with the central lumen through the side.

(4) The artificial tendon-forming auxiliary instrument according to (3), in which chamfered portions are respectively formed in circumferences of both ends of the tendon guide portion in the longitudinal direction.

(5) The artificial tendon-forming auxiliary instrument according to (3) or (4), in which an easily-tearable portion for tearing the tendon guide portion is formed on a circumferential surface of the tendon guide portion along the longitudinal direction.

(6) The artificial tendon-forming auxiliary instrument according to (5), in which the easily-tearable portion is formed on a side facing the slit portion in the circumferential surface of the tendon guide portion along the slit portion across the overall length in the longitudinal direction.

(7) The artificial tendon-forming auxiliary instrument according to (6), in which the easily-tearable portion is a recessed groove which is formed by cutting toward the central lumen in a non-penetration manner from the circumferential surface of the tendon guide portion, and an opening width of the easily-tearable portion is smaller than the opening width of the slit portion.

(8) The artificial tendon forming auxiliary instrument according to any one of (5) to (7), in which a pair of the instrument holding portions is formed on both sides so as to interpose the easily-tearable portion therebetween.

(9) The artificial tendon-forming auxiliary instrument according to any one of (5) to (8), in which the pair of instrument holding portions is formed so as to respectively protrude outward from the circumferential surface of the tendon guide portion and extend toward the side facing the slit portion.

(10) The artificial tendon-forming auxiliary instrument according to (8) or (9), in which when the pair of instrument holding portions is pinched and is caused to approach each other, the opening width of the slit portion is widened without tearing the easily-tearable portion.

(11) The artificial tendon-forming auxiliary instrument according to any one of (1) to (10), in which a rough surface portion is provided in at least a part on a surface of the instrument holding portion.

(12) An auxiliary instrument set includes a plurality of the artificial tendon-forming auxiliary instruments according to any one of (1) to (11).

(13) The auxiliary instrument set according to (12), in which sizes of the tendon guide portions in a longitudinal direction in the plurality of artificial tendon-forming auxiliary instruments are equal to each other.

(14) The auxiliary instrument set according to (12), in which sizes of the tendon guide portions in the longitudinal direction in the plurality of artificial tendon-forming auxiliary instruments are different from each other.

(15) The auxiliary instrument set according to (14), in which a difference in the sizes of the tendon guide portions in the longitudinal direction in the plurality of artificial tendon-forming auxiliary instruments is N (where N is an integer equal to or greater than 1) millimeters.

(16) An auxiliary instrument set includes a plurality of the auxiliary instrument sets according to any one of (12) to (15). Average values of the sizes of the tendon guide portions in a longitudinal direction in the plurality of artificial tendon-forming auxiliary instruments respectively provided in the plurality of auxiliary instrument sets are different from each other.

(17) A somatometry instrument measures a distance between a first site inside a living body and a second site physically separated from the first site. The instrument includes an end-portion abutment portion which is able to abut on the first site and is provided at one end of the somatometry instrument in a longitudinal direction; a first insertion port which is provided in the end-portion abutment portion and through which an artificial thread stitching the first site is inserted; a draw-out portion which is provided at an opposite end facing the end-portion abutment portion in the longitudinal direction or at an intermediate portion that is an intermediate region between the end-portion abutment portion and the opposite end, and through which the artificial thread inserted through the first insertion port is drawn out in an outward direction of the somatometry instrument; and a measurement portion which is provided in the intermediate portion and measures the distance between the first site and the second site.

(18) The somatometry instrument according to (17) further includes a holding portion which is provided at a position biased to the opposite end in the longitudinal direction so as to hold the somatometry instrument.

(19) The somatometry instrument according to (17) or (18) further includes an artificial thread guidance portion which extends in the longitudinal direction across the first insertion port and the draw-out portion.

(20) The somatometry instrument according to (19), in which the artificial thread guidance portion has opening portions which are continuously open with opening widths capable of receiving the artificial thread across the longitudinal direction.

(21) The somatometry instrument according to (20), in which the draw-out portion is provided at the opposite end. The intermediate portion has a minimum opening width of the opening portion observed on a cut surface cut in a direction orthogonal to the longitudinal direction greater than minimum opening widths of both end-portion regions in the longitudinal direction.

(22) The somatometry instrument according to (20) or (21), in which the draw-out portion is provided at the opposite end. The intermediate portion has an outer circumferential opening width of the opening portion observed from an outer circumference side of the somatometry instrument greater than outer circumferential opening widths of both the end-portion regions in the longitudinal direction.

(23) The somatometry instrument according to any one of (17) to (22), in which the measurement portion is an outer circumferential surface of the somatometry instrument.

(24) The somatometry instrument according to any one of (17) to (23), in which the measurement portion includes a protrusion portion which protrudes from the outer circumferential surface of the somatometry instrument in the outward direction and extends in the longitudinal direction.

(25) The somatometry instrument according to any one of (17) to (24), in which the measurement portion has a measuring scale which is able to measure a predetermined distance from the end-portion abutment portion in the longitudinal direction.

(26) The somatometry instrument according to any one of (17) to (25) further includes a movable portion which is able to move the measurement portion in the longitudinal direction.

(27) The somatometry instrument according to any one of (17) to (26), in which the second site is a valve cusp of a cardiac valve. The first site is a papillary muscle positioned on a downstream side in a normal blood flow direction with respect to the valve cusp.

(28) The somatometry instrument according to (27), in which the somatometry instrument is used for selecting a size of an artificial tendon-forming auxiliary instrument which is used for joining the valve cusp and the papillary muscle with an artificial tendon. The somatometry instrument further includes the artificial thread guidance portion which extends in the longitudinal direction across the first insertion port and the draw-out portion. In a state where the artificial tendon stitching the papillary muscle is guided to the artificial thread guidance portion and the end-portion abutment portion abuts on the papillary muscle, the measurement portion measures the distance between the papillary muscle and the valve cusp.

(29) The somatometry instrument according to (28), in which the artificial tendon-forming auxiliary instrument includes a pair of end-portion support portions which respectively support the valve cusp and the papillary muscle and are provided at both ends of the instrument in the longitudinal direction, first and second tendon insertion ports which are respectively formed in the pair of end-portion support portions and have diameters greater than a diameter of the artificial tendon and through which the artificial tendon is inserted, a tendon guide portion which is formed so as to extend in the longitudinal direction across the first and second tendon insertion ports, and an instrument holding portion which is formed in the intermediate portion of the tendon guide portion in the longitudinal direction.

(30) An auxiliary instrument set includes the somatometry instrument according to any one of (17) to (29), and an artificial tendon-forming auxiliary instrument used for joining a valve cusp of a cardiac valve and a papillary muscle positioned on a downstream side in a normal blood flow direction with respect to the valve cusp, with an artificial tendon.

(31) The auxiliary instrument set according to (30), in which the artificial tendon-forming auxiliary instrument includes a pair of end-portion support portions which respectively support the valve cusp and the papillary muscle and are provided at both ends of the instrument in a longitudinal direction, and first and second tendon insertion ports which are respectively formed in the pair of end-portion support portions and have diameters greater than a diameter of the artificial tendon and through which the artificial tendon is inserted. Calibers of the first and second tendon insertion ports of the artificial tendon-forming auxiliary instrument and a caliber of a first insertion port of the somatometry instrument are substantially the same as each other.

(32) The auxiliary instrument set according to (30) or (31) further includes a plurality of the somatometry instruments and a plurality of the artificial tendon-forming auxiliary instruments. The plurality of artificial tendon-forming auxiliary instruments include the artificial tendon-forming auxiliary instruments having sizes in the longitudinal direction different from each other. All of the sizes of the plurality of artificial tendon-forming auxiliary instruments in the longitudinal direction fall below a size of the somatometry instrument in the longitudinal direction.

(33) The auxiliary instrument set according to any one of (30) to (32), in which the artificial tendon-forming auxiliary instrument has a record portion in which the size of the artificial tendon-forming auxiliary instrument in the longitudinal direction is recorded and is able to be viewed from the outside.

REFERENCE SIGNS LIST

10 CIRCUMFERENTIAL SURFACE
12 SLIT PORTION
12a WIDE-WIDTH PORTION
12b NARROW-WIDTH PORTION
12c INTRODUCTION PORTION
14 CENTRAL LUMEN
16 EASILY-TEARABLE PORTION
16a FIRST EASILY-TEARABLE PORTION
16b SECOND EASILY-TEARABLE PORTION
18 RETURN RESTRICTION PORTION
20, 21 END-PORTION SUPPORT PORTION
22 FIRST TENDON INSERTION PORT
23 SECOND TENDON INSERTION PORT
24 INTERMEDIATE BUMPER PLATE
25 INTERMEDIATE TENDON INSERTION PORT
30 TENDON GUIDE PORTION
32 CHAMFERED PORTION
40 INSTRUMENT HOLDING PORTION
42 ROUGH SURFACE PORTION
100 AUXILIARY INSTRUMENT (FIRST EMBODIMENT)
101 AUXILIARY INSTRUMENT (SECOND EMBODIMENT)
102 AUXILIARY INSTRUMENT (THIRD EMBODIMENT)
103 AUXILIARY INSTRUMENT (FOURTH EMBODIMENT)
104 AUXILIARY INSTRUMENT (FIFTH EMBODIMENT)
105 AUXILIARY INSTRUMENT (SIXTH EMBODIMENT)
106 AUXILIARY INSTRUMENT (SEVENTH EMBODIMENT)
150 AUXILIARY INSTRUMENT SET
152 STERILIZATION CONTAINER
200 ARTIFICIAL TENDON
202, 203 PUNCTURE NEEDLE
204, 206 PAD
207 LOOP PORTION
208 KNOT
210 VALVE CUSP
212 PAPILLARY MUSCLE
214 TENDON
300 HEART
302 LEFT ATRIUM
304 LEFT VENTRICLE
306 RIGHT ATRIUM
308 RIGHT VENTRICLE
310 MITRAL VALVE
312 TRICUSPID VALVE
314 AORTIC VALVE
316 PULMONARY ARTERIAL VALVE
320 AORTA
322 PULMONARY VEIN
W1, W2 OPENING WIDTH
1010 . . . END-PORTION ABUTMENT PORTION
1012 . . . MEASURING SCALE
1020 . . . FIRST INSERTION PORT
1030 . . . SECOND INSERTION PORT
1040 . . . MEASUREMENT PORTION
1042 . . . PROTRUSION PORTION
1044 . . . MOVABLE PORTION
1050 . . . HOLDING PORTION
1060 . . . OPENING PORTION
1060a . . . NARROW WIDTH REGION
1060b . . . WIDE WIDTH REGION
1070 . . . ARTIFICIAL THREAD GUIDANCE PORTION
1070a . . . THROUGH HOLE
1070b . . . RECESSED PORTION
1100, 1100a, 1100b . . . SOMATOMETRY INSTRUMENT
1110 . . . ONE END
1112 . . . OPPOSITE END
1120 . . . OUTER CIRCUMFERENTIAL SURFACE
1150, 1152 . . . PACK
1200 . . . ARTIFICIAL TENDON

1201 ... ARTIFICIAL THREAD
1202 ... PUNCTURE NEEDLE
1203 ... FRENCH KNOT PORTION
1204 ... PAD
1205 ... STITCH PORTION
1206 ... PAD
1208 ... KNOT
1210 ... VALVE CUSP
1212 ... PAPILLARY MUSCLE
1212a ... PAPILLARY MUSCLE
1212b ... PAPILLARY MUSCLE
1214 ... TENDON
1220 ... MARKER
1221 ... INK ABSORPTION PORTION
1300 ... HEART
1302 ... LEFT ATRIUM
1304 ... LEFT VENTRICLE
1306 ... RIGHT ATRIUM
1308 ... RIGHT VENTRICLE
1310 ... MITRAL VALVE
1312 ... TRICUSPID VALVE
1314 ... AORTIC VALVE
1316 ... PULMONARY ARTERIAL VALVE
1320 ... AORTA
1322 ... PULMONARY VEIN
1400 ... ARTIFICIAL TENDON-FORMING AUXILIARY INSTRUMENT
1402 ... TWEEZERS
1410 ... CIRCUMFERENTIAL SURFACE
1412 ... SLIT PORTION
1412a ... WIDE-WIDTH PORTION
1412b ... NARROW-WIDTH PORTION
1414 ... CENTRAL LUMEN
1416 ... EASILY-TEARABLE PORTION
1420, 1421 ... END-PORTION SUPPORT PORTION
1422, 1423 ... FIRST AND SECOND TENDON INSERTION PORTS
1430 ... TENDON GUIDE PORTION
1440 ... INSTRUMENT HOLDING PORTION
1444 ... RECORD PORTION
1500 ... AUXILIARY INSTRUMENT SET
L1001 TO L1004 ... SIZE
W1001, W1002 ... MINIMUM OPENING WIDTH
W1003, W1004 ... OPENING WIDTH
W1005, W1006 ... OUTER CIRCUMFERENTIAL OPENING WIDTH

The invention claimed is:

1. An artificial tendon-forming auxiliary instrument for joining a valve cusp of a cardiac valve and a papillary muscle with an artificial tendon, comprising:
a main body having a tendon guide portion extending in a longitudinal direction of the main body, a pair of end-portion support portions which support the valve cusp and the papillary muscle respectively and are formed at ends of the main body in the longitudinal direction, a first tendon insertion port formed in one of the pair of end-portion support portions, and a second tendon insertion port formed in the other one of the pair of end-portion support portions; and
an instrument holding portion formed in an intermediate portion of the tendon guide portion in the longitudinal direction at a position that biases one of the end-portion support portions on one side in the intermediate portion of the tendon guide portion,
wherein the first and second tendon insertion ports have diameters greater than a diameter of the artificial tendon such that the artificial tendon is inserted, the tendon guide portion is formed to extend in the longitudinal direction across the first and second tendon insertion ports, the pair of end-portion support portions have chamfered portions formed in circumferences of the end-portion support portions, respectively, and the main body has a tearable portion which is a recessed groove formed on a circumferential surface of the tendon guide portion along the longitudinal direction such that the tearable portion tears the tendon guide portion in the longitudinal direction.

2. The artificial tendon-forming auxiliary instrument according to claim 1, wherein the main body is in a hollow tubular shape and includes a slit portion which is open with an opening width configured to receive the artificial tendon, and a central lumen which penetrates the tendon guide portion in the longitudinal direction, and the slit portion is formed on a side of the tendon guide portion across an overall length in the longitudinal direction and communicates with the central lumen through the side.

3. The artificial tendon-forming auxiliary instrument according to claim 2, wherein the tearable portion is formed on a side facing the slit portion in the circumferential surface of the tendon guide portion along the slit portion across the overall length in the longitudinal direction.

4. The artificial tendon-forming auxiliary instrument according to claim 3, wherein the recessed groove is formed by cutting toward the central lumen in a non-penetration manner from the circumferential surface of the tendon guide portion, and an opening width of the tearable portion is smaller than the opening width of the slit portion.

5. The artificial tendon-forming auxiliary instrument according to claim 4, wherein a rough surface portion is formed in at least a part of a surface of the instrument holding portion.

6. The artificial tendon-forming auxiliary instrument according to claim 3, wherein the instrument holding portion is formed in a pair on both sides such that the pair of instrument holding portions interpose the tearable portion therebetween.

7. The artificial tendon-forming auxiliary instrument according to claim 6, wherein the pair of instrument holding portions is formed such that the pair of instrument holding portions protrude outward from the circumferential surface of the tendon guide portion and extend toward the side facing the slit portion, respectively.

8. The artificial tendon-forming auxiliary instrument according to claim 6, wherein when the pair of instrument holding portions is pinched and is caused to approach each other, the opening width of the slit portion is widened without tearing the tearable portion.

9. The artificial tendon-forming auxiliary instrument according to claim 3, wherein a rough surface portion is formed in at least a part of a surface of the instrument holding portion.

10. An auxiliary instrument set, comprising:
a plurality of artificial tendon-forming auxiliary instruments each comprising the artificial tendon-forming auxiliary instrument of claim 3.

11. The auxiliary instrument set according to claim 10, wherein the plurality of artificial tendon-forming auxiliary instruments has a plurality of tendon guide portions in the longitudinal direction such that the plurality of tendon guide portions has sizes that are equal to each other.

12. The auxiliary instrument set according to claim 10, wherein the plurality of artificial tendon-forming auxiliary instruments has a plurality of tendon guide portions in the longitudinal direction such that the plurality of tendon guide portions has sizes that are different from each other.

13. The auxiliary instrument set according to claim 12, wherein a difference in the the tendon guide portions in the longitudinal direction in the plurality of artificial tendon-forming auxiliary instruments is N where N is an integer equal to or greater than 1 millimeter.

14. An auxiliary instrument set, comprising:
a plurality of auxiliary instrument sets each comprising the auxiliary instrument set of claim 10, wherein average values of sizes of tendon guide portions in the longitudinal direction in the plurality of artificial tendon-forming auxiliary instruments in the plurality of auxiliary instrument sets are different from each other.

15. The artificial tendon-forming auxiliary instrument according to claim 2, wherein the instrument holding portion is formed in a pair on both sides such that the pair of instrument holding portions interpose the tearable portion therebetween.

16. The artificial tendon-forming auxiliary instrument according to claim 15, wherein the pair of instrument holding portions is formed such that the pair of instrument holding portions protrude outward from the circumferential surface of the tendon guide portion and extend toward the side facing the slit portion, respectively.

17. The artificial tendon-forming auxiliary instrument according to claim 15, wherein when the pair of instrument holding portions is pinched and is caused to approach each other, the opening width of the slit portion is widened without tearing the tearable portion.

18. The artificial tendon-forming auxiliary instrument according to claim 2, wherein the recessed groove is formed by cutting toward the central lumen in a non-penetration manner from the circumferential surface of the tendon guide portion, and an opening width of the tearable portion is smaller than the opening width of the slit portion.

19. The artificial tendon-forming auxiliary instrument according to claim 1, wherein the instrument holding portion is formed in a pair on both sides such that the pair of instrument holding portions interpose the tearable portion therebetween.

20. The artificial tendon-forming auxiliary instrument according to claim 19, wherein the pair of instrument holding portions is formed such that the pair of instrument holding portions protrude outward from the circumferential surface of the tendon guide portion and extend toward the side facing the slit portion, respectively.

21. The artificial tendon-forming auxiliary instrument according to claim 19, wherein when the pair of instrument holding portions is pinched and is caused to approach each other, the opening width of the slit portion is widened without tearing the tearable portion.

22. The artificial tendon-forming auxiliary instrument according to claim 2, wherein a rough surface portion is formed in at least a part of a surface of the instrument holding portion.

23. An auxiliary instrument set, comprising:
a plurality of artificial tendon-forming auxiliary instruments each comprising the artificial tendon-forming auxiliary instrument of claim 2.

24. The auxiliary instrument set according to claim 23, wherein the plurality of artificial tendon-forming auxiliary instruments has a plurality of tendon guide portions in the longitudinal direction such that the plurality of tendon guide portions has sizes that are equal to each other.

25. The auxiliary instrument set according to claim 23, wherein the plurality of artificial tendon-forming auxiliary instruments has a plurality of tendon guide portions in the longitudinal direction such that the plurality of tendon guide portions has sizes that are different from each other.

26. The auxiliary instrument set according to claim 25, wherein a difference in the sizes of the tendon guide portions in the longitudinal direction in the plurality of artificial tendon-forming auxiliary instruments is N where N is an integer equal to or greater than 1 millimeter.

27. An auxiliary instrument set, comprising:
a plurality of auxiliary instrument sets each comprising the auxiliary instrument set of claim 23, wherein average values of sizes of tendon guide portions in the longitudinal direction in the plurality of artificial tendon-forming auxiliary instruments in the plurality of auxiliary instrument sets are different from each other.

28. The artificial tendon-forming auxiliary instrument according to claim 1, wherein a rough surface portion is formed in at least a part of a surface of the instrument holding portion.

29. An auxiliary instrument set, comprising:
a plurality of artificial tendon-forming auxiliary instruments each comprising the artificial tendon-forming auxiliary instrument of claim 1.

30. The auxiliary instrument set according to claim 29, wherein the plurality of artificial tendon-forming auxiliary instruments has a plurality of tendon guide portions in the longitudinal direction such that the plurality of tendon guide portions has sizes that are equal to each other.

31. The auxiliary instrument set according to claim 29, wherein the plurality of artificial tendon-forming auxiliary instruments has a plurality of tendon guide portions in the longitudinal direction such that the plurality of tendon guide portions has sizes that are different from each other.

32. The auxiliary instrument set according to claim 31, wherein a difference in the sizes of the tendon guide portions in the longitudinal direction in the plurality of artificial tendon-forming auxiliary instruments is N where N is an integer equal to or greater than 1 millimeter.

33. An auxiliary instrument set, comprising:
a plurality of auxiliary instrument sets each comprising the auxiliary instrument set of claim 29, wherein average values of sizes of tendon guide portions in the longitudinal direction in the plurality of artificial tendon-forming auxiliary instruments in the plurality of auxiliary instrument sets are different from each other.

\* \* \* \* \*